United States Patent [19]
Tal et al.

[11] Patent Number: 5,759,828
[45] Date of Patent: Jun. 2, 1998

[54] CYCLIC DI-GUANYLATE METABOLIC ENZYMES

[75] Inventors: Rony Tal, Richmond; David H. Gelfand, Oakland; Roger D. Calhoon, San Diego, all of Calif.; Arie Ben-Bassat, Gainesville, Fla.; Moshe Benziman, Jerusalem, Israel; Hing Cheung Wong, San Ramon, Calif.

[73] Assignee: Weyerhaeuser, Federal Way, Wash.

[21] Appl. No.: 309,512

[22] Filed: Sep. 20, 1994

Related U.S. Application Data

[63] Continuation of Ser. No. 800,218, Nov. 29, 1991, abandoned.

[51] Int. Cl.$^6$ .............. C12N 15/63; C12N 15/70; C12N 15/74; C12P 1/04
[52] U.S. Cl. .............. 435/172.3; 435/69.1; 435/71.1; 435/170; 435/199; 435/232; 435/320.1; 935/9; 935/11; 935/66; 935/72; 935/73; 536/23.1; 536/23.2; 536/23.7
[58] Field of Search .............. 435/172.3, 69.1, 435/71.1, 170, 320.1, 199, 232; 935/6, 9, 11, 66, 72, 73; 536/23.1, 23.2, 23.7

[56] References Cited

U.S. PATENT DOCUMENTS 5,001,230  3/1991  Brown et al. .............. 536/23.5

FOREIGN PATENT DOCUMENTS

WO 90/12098  10/1990  WIPO .

OTHER PUBLICATIONS

Ross, et al., *Nature*, 325:279–281 (1987).
Ross, et al., *Microbiological Reviews* 55(1):35–58 (1991).
Ross, et al., *The Journal of Biological Chemistry* 265:18933–18943 (1990).
Ross, et al., *FEBS Letters* 186:191–196 (1985).
Benziman and Palgi, *Journal of Bacteriology* 104:211–218 (1970).
Ross, et al., *Carbohydrate Research* 149:101–117 (1986).
Abstract of Papers: American Chemical Society A. Ben-Bassat, et al., "Genetic Engineering Methods to Increase Cellulose Volumetric Productivity and Yield in *ACETOBACTER xylinum*", vol. 203, No. 1–3, Apr. 1992.
Bailey, J. E. (1991) Toward A Science of Metabolic Engineering, Science, vol. 252, pp. 1668–1675.
Walsh, K.A. et al. (1981) Advances in Protein Sequencing in "Annual Review of Biochemistry," vol. 50, pp. 261–284. (Annual Reviews, Inc., Palo Alto, CA).
Lathe, R. (1985) Journal of Molecular Biology, vol. 183, pp. 1–12.
Shatzman, A. R. et al. (1987) in "Methods in Enzymology", vol. 152, pp. 661–673, (Academic Press, San Diego, CA).

*Primary Examiner*—Mindy Fleisher
*Assistant Examiner*—Nancy J. Degen
*Attorney, Agent, or Firm*—Albert P. Halluin; Pennie & Edmonds

[57] ABSTRACT

The present invention provides the nucleotide sequences of Acetobacter operons, cdg operons encoding genes for the biosynthesis and degradation of cyclic diguanosine monophosphate (c-di-GMP). Specifically, the nucleotide sequences and deduced amino acid sequences of 3 phosphodiesterases isozymes, 3 diguanylate cyclase isozymes, and 2 polypeptides of unidentified function are provided. Also provided for are various strains of microorganisms, including Acetobacter cells genetically manipulated so as to produce elevated and/or reduced levels of one or more cdg operon encoded proteins.

14 Claims, 20 Drawing Sheets

FIG. 1A

```
cdg1        1  ..gggggaagcgaagtcccggtccataacggacgcttacatcatatgctctgatatcctgt
cdg2        1
cdg3        1
consensus      ..gggggaagcgaagtcccggtccataacggacgcttacatcatatgctctgatatcctgt cdg1       62  taaccattaactgaaagtataaactgtcaggaatgggccaaaatccggggcggatattctg
cdg2        1
cdg3        1
consensus      taaccattaactgaaagtataaactgtcaggaatgggccaaaatccggggcggatattctg cdg1      123  tatctattttacaaattaacttatggcgaaaatatgtcattaatgagatcattcgtaatcg
cdg2        1
cdg3        1
consensus      tatctattttacaaattaacttatggcgaaaatatgtcattaatgagatcattcgtaatcg cdg1      184  tcgttgagaacagaaaaaaattaacatgtctcttgtgcagcctctcttgtcttctgatgga
cdg2        1
cdg3        1
consensus      tcgttgagaacagaaaaaaattaacatgtctcttgtgcagccttctctgtcttctgatgga cdg1      245  acgaaacggacattttccgaacgtcaggaattcatgacggaagatatgcCcgCCagcAtGC
                                                                  |  ||    | |
cdg2        1                                           ccccgcactCgaCCccgAcGa
cdg3        1
consensus      acgaaacggacattttccgaacgtcaggaattcatgacgg---------c--cc---a-g- cdg1      306  aTTTCCatGtgGtgtccgGagGcgcgcGcGttttcaaatccCtGcctgacgGGcgGCGGCA
               |||||  |   |      |   |    |            | |     ||  ||||||
cdg2       22  cTTTCCcaGccGcaaggcGctGgcgcaGgCggcctggcgtgCgGtggcggcGGgtGCGGCA
cdg3        1
consensus      -tttcc--g--g------g--g-----g-c-----------c-g-------gg--gcggca
```

FIG. 1B

```
cdg1        367 GAttatcGgTtttgCccAtaaAGGCgatgtgCtcCCCGcctatccctgcacccgctAcCAt
                  ||    |  |    |   ||||    |  ||||                      |  ||
cdg2         83 GA     GtTgcgcCagAaccAGGC    cCagCCCG                      AgCAg
cdg3          1
consensus       gattatcg-t----c---a---aggcgatgt-c--cccgcctatccctgcacccgcta-cacdg1        428 tACAGCGCCgaagccatgcgcaGCCTGcaggtggtgtgcgtgcccgcgccctatctgagcc
                ||||||||             |||||
cdg2        116 gACAGCGCC            tatGCCTG
cdg3          1                                                    gnaaanccncccccnccc
consensus       -acagcgccgaagccatgc---gcctgcaggtggtgtgcgtgc------cc---c----cc cdg1        489 acctgcatgaaacctcgcccggtgcttgcgcggcttcgctgaattCCGCCCGCcagttGct
                                                             ||||||||       |
cdg2        133                                              CCGCCCGC ttgCGgg
                                                                       |  ||  |
cdg3         19 cccaaggggggggatgtggcggcctggttcgggcttgcgcgggcaaggGattGCggccCccc
consensus       -cc-----g-------g-c-g-----t-cg-g---t-cgc-g----ccGcccGC----cgccdg1        550 ggTcagcCtGCAtGccCggctgCtCatgcttgGccgccagaCcgCGCgcGaGcgccTGgca
                  |     | ||| ||  ||  | |      | |        | |||  | | ||  ||
cdg2        148 cATgCtgCcGCAgGatCttgAaCgCcacggcaGataaGgcGCgaCGCtgGcGgCttTGtgt
                  |         |  | |    |         |   |   |  | |  |       |
cdg3         80 aAaaCcttgaCAtatgtggaAtatgncaattttgcgtGcgGgatgtgatGgatCaaccgcc
consensus       -at-c--c-gCAtg--cgg-a-ctc----tt-g-cg-g-ggc--cgc--G-g-c--tggccdg1        611 accttcctgctCggtcaggGcacgCGCATGGGgccgggtgaactctggcccgttgatccgt
                           |        |     ||||||||
cdg2        209 caaGAtTGaggCATGtcatGtTtCCGCATGGG
                   || ||   |||   |||   |     |
cdg3        141 tgcGAaTGctatATGgacgcaTcCattccaGacggaaattattaaagacgaccttaattca
consensus       --cga-tg---catg-a-gg-tcccgcatgGg------t-a-----g-c----t-a----- cdg1        672 ccatttcacgtgcggacatggCcgAttTCcTtGgcctgacCaccgagactGTcagCCgccT
                    | | ||  |||       | ||| ||                   ||  || ||  |
cdg2        241                      CatAaaTCaTAGtatgAtgCctgcgccgAGTggtCCcgaT
                                        |  |                    |       |
cdg3        202 tatcaatgtggtataatgattatcttgaataAtatgtAatatgcttatcAtcatcCtatga
consensus       ---------g-----a-----c--at-tc-tag---taa-c--c----cagt---Cc---t
```

FIG. 1C

```
cdg1       733  GCtcagTgCCttccatCgggagcaGcTTaTctgCcgggaAcGgCGCGCCAtccatattctc
                ||   |  ||   |    |  |||| |   |       |  | |||||||
cdg2       281  GCcTgtTtCCGCatggCcatgaTcGaTTCTgaCCGcTtgAtGaCGCGCCA    ggCGGa
                | |  ||       |      |  |||  |     ||            |||
cdg3       263  tatTccTgCgGCcgccatgcacTgtcccCgccCgGgTgatgGcgcgcCCtgcatttcCGGt
consensus       gctt--TgCcgcc---c-g-a-t-gcttctc-ccggtgaa-G-cgcgCCa-c---t--cggcdg1       794  gatCctgaCcGcTtgcGggcgatcgtggcCcaccCagaaTgacagcgaagaAaGacagcac
                    |||    |  |  |                |    |                   | |
cdg2       337  tGCCTgccCaGgTCagGaaaatGatcttaCatGGCGcggTtgggcgtgCCgATGTtCtgGa
                ||||    |   |        |         ||              ||    |   |
cdg3       324  cGCCTtatataccCctGctgcaGccgcctgccGGtGgctgccccttgtCCctTtTgCgaGg
consensus       -gcCtt--c-gctc--G----agc-----cc-ggcgg--t--c---g-cc-atgt-cg-g- cdg1       855  GacgAtGcccGAcatcaCagcccTcAcCaCaGAaaTCCTtCttcCcGCccTtGAGCAGGCC
                    |   |  ||     |        |   |  ||  |||| |    |  |  ||||||||
cdg2       398  GtttACGgTGGAtcAGCCgAAgaTtAGCGCcGAtGTCCTGCTTTCtGCtaTGGAGCAGGCC
                    | ||   |||||| ||  | ||||| || ||||||| |||| || | ||||||||||
cdg3       385  taactCaaTGtcaaAGCCtAAccTgAGCGCtGAaGTCCTGaTTTCgGCacTGGAGCAGGCC
consensus       ga--acg-tgga-aagcC-aaccT-AgCgC-GAagTCCTgcTTtC-GC-cTgGAGCAGGCC cdg1       916  ATTGATgCaActGTCaTcATcGggcAGgAaAACgagATCATCTTCTatAACcaGGCGGCgG
                ||||||  | |   |||  |  | |  ||  |||    ||||||||||  |||  |||||||  |
cdg2       459  ATTGATcCcAtgGTCgTgATTGATGAGcAtAACctcATCATCTTCTTCAACgcGGCGGCcG
                || |||  | |  ||   |   | |||||||||  |  |  ||||||||||||||  |||||
cdg3       446  ATaGAcgCaAccGTgaTtATTGATGAcaAgAACgaagTCATCTTCTTCAAtcaGGCGGgat
consensus       ATtGAtgCaAc-GTcaT-ATtGatgAg-A-AACga-aTCATCTTCTtcAAccaGGCGGc-g cdg1       977  AatcccTgTGGGGCattcCcCGCGccGAcGTgATcGGcCGCAATGTcgaCTGCCTgGTGCC
                |      | |||||| |  |  ||||   | | |||  |  ||  ||||||||  ||||||  |||||
cdg2       520  AGAAgaTaTGGGGCtgCtCgCGCGAAGAgGTcATGGGtCGCAATGTGAgCTGCCTcGTGCC
                |||   |  ||||||  |  ||||||   | |||||   || ||||| |   ||  ||||||
cdg3       507  cGAAccTgTGGGGCctCgacaagaAAGAtGTgcTGGGcaagAAcGTGAaCgtgCTgGTGCC
consensus       agaaccTgTGGGGC-tc-cccgcgaaGA-GTgaTgGGccgcAAtGTgaaCtgcCTgGTGCC cdg1      1038  CaccCgCctGCGCcATgagCATGAccgCTACATCgACCGCAAcCGCGAGACCGGGcataaC
                    |  | |  ||||| ||  ||||||| |||||||| ||||||||  ||||||||||  ||||||     |
cdg2       581  CgaaCcCgAGCGCGAtCgCcATGAtGaCTACATCaACCGCAAtCGCGAGACCGGGgtcggC
                    |   |  ||||||| | ||||||| ||  | ||||  | |||||  || |||||  ||  |  |     |
cdg3       568  CacgCtgcAtCagGccgGgCAcGAcGcCTttgTCgAgCGCAgcCGgGgcAgCtGcataaC
consensus       Cac-C-ccagCgcgatgggCATGAcg-CTacaTCgAcCGCAacCGcGagAcCgGgcataaC
```

FIG. 1D

```
cdg1       1099  CGcATTGTCGGCACaTCGCGCGAGGTgGAgTTCaccCGCGCCgATGGgGAaTAcaTCTGTG
                 || |||||||||||| |||||||||||| || |||    |||||| |||| || ||  |||||||
cdg2        642  CGgATTGTCGGCACCTCGCGCGAGGTcGAaTTCcgtCGCGCCaATGGcGAgTATgTCTGTG
                 || ||||||||||||||||||||||||||| || |||   ||| |  |||| || ||| |||| |
cdg3        629  CGcATTGTCGGCACCTCGCGCGAGGTgGAgTTCaccCGCtCggATGGgGAaTATaTCTGcG
consensus        CGcATTGTCGGCACcTCGCGCGAGGTgGAgTTCaccCGCgCcgATGGgGAaTAtaTCTGtG cdg1       1160  GCGAGCTtTCgcTCTCCaagGTGCAGaTcggccAggGCGaCAAGcggctcAcCTACTACAT
                 |||||||| |  ||||  ||||||||  |   |||||| ||||         |  ||||||||
cdg2        703  GCGAGCTGTCcaTCTCGcgCGTGCAGGTGAAtGATtGCGgCAAG       ATCTACTACAT
                 ||||||||| |    |  |   |||||| |||  |   |   ||||       | || | |||
cdg3        690  GCGAGCTGTC    gctGtcCaaGgtcGTGAAcGATgaC      aagcgcATCTttTtCAT
consensus        GCGAGCTgTC--tctcg--cgtGcaggTgaacgATggCg-caag--gc-cAtCTacTaCAT cdg1       1221  gGgcGTgATGAAGaACGTcACgGAGgAgAGCCagCgcCGCAAGATcCTGaTcCTGCAgAAc
                 |  || ||||||| |||| || ||| |  |||| |  |||||||||  | | || |||| ||
cdg2        758  cGcgGTcATGAAGgACGTgACCGAGcAAAGCCgcCAGCGCAAGATaCTGgTgCTGCAaAAt
                 |  || ||||||| |  || || || |  ||||| |||||||||||| ||  | || |||| ||
cdg3        742  gGgcGTgATGAAGaATGTcACCAacgAAAGCCagCAGCGCAAGATcCTGaTcCTGCAgAAc
consensus        gGgcGTgATGAAGaAcGTcACcgAggAaAGCCagCagCGCAAGATcCTGaTcCTGCAgAAc cdg1       1282  GAcGTGCTgCAGGCgCTgGCcagCGACATGctgATcCAGGAtaTtGGCGAgCTGaTcTGCC
                 || |||||| ||||| || ||   |||||||   ||  ||  |  ||||| |||| | ||||
cdg2        819  GAtGTGCTcCAGGCcCTCGCatcCGACATGAgcATaCAGGAaGTGGGCGACCTGCTGTGCC
                 || |||||| ||||| ||||| |||||||| || ||||| |||| |||||| |||||| ||||||
cdg3        803  GAcGTGCTgCAGGCaCTCGCcagCGACATGAtgATcCAGGAcGTGGcCGACCTtCTGTGCC
consensus        GAcGTGCTgCAGGC-CTcGCcagCGACATGatgATcCAGGA-gTgGgCGAcCTgcTgTGCC cdg1       1343  GCaaGGttGAagccTTCGTGCCCaaCtCGGTcGcgGCctTGcTGgTGcTCGATgatgCGCa
                 ||  || ||    ||||||||||  | || |||  ||  || ||| || ||||       |||
cdg2        880  GCCGGGcGGAcAGtTTCGTGCCCGGCgCGGTtGgCGCGCTGATGCTGATCGAcCgctCGCG
                 |||||| ||| ||  ||||||||||||| |||| | || ||| |||||||| |    |
cdg3        864  GCCGGGtGGAaAGcTTCGTGCCCGGCaCGGTgGcCGtGCTcATGCTGATtacgCcagacgG
consensus        GCcgGGtgGAaagcTTCGTGCCCggC-CGGT-GccGcgcTgaTGcTGaTcga-c--gcgcg cdg1       1404  gccttggcgGGTgAtctgCaCctCCgCCcTGCCgccGCGCatCCGCaatGCgCTtGAaAcC
                 |||  |     | ||    || || ||  |||||||   |||||| |    ||  || || ||
cdg2        941  cagGcTttcGGTcAgtgCCTCgCCCtCCaTGCCCAAGCGCTACCGCGCgGCaCTCGAcAGC
                 || ||     ||  |  ||  || || ||  |||||||||||||||||||||| | ||||| |||
cdg3        925  gcaGtTgcgcGTtctgtCCagcCCCaCacTGCCCAAGCGCTACCGCGCctCgCTCGAgAGC
consensus        gc-gttgcggGT-at-tcCaccCC-CccTGCCcaaGCGCtaCCGCgc-gCgCTcGA-Agc
```

FIG. 1E

```
cdg1       1465  AccgtGCcgtCaCCttcGgAtgTgGAAAaGCTcaagGCCAAtgCCtCCtatAcCggCcaCc
                  |  ||  |  || || ||||  |  |  |||| ||||   |  ||  |  | | |
cdg2       1002  ATGcAGCTtaCcCCcgaGcAgCTtGAAAtGCTGCGCGCCAAcCCCgCCggCAgCAaCacCg
                  ||  |     |  ||  |   || ||| |||||||| | |||     | |||  |
cdg3        986  cTGtAtgTctCgtCatccgAaCTcGAgAaGCTGCGCGtCgAtCCCaagcaCgcCAcCcgCa
consensus        atg-agct-tC-cC-tcggA-cT-GAaAaGCTgcgcGcCaAtcCC-cc-acacCa-Cc-c- cdg1       1526  TaGTGTGGaAcaaCTACcagTCcaTGtgCCGCTCGCTGGGGcTGcAGtcGTGCTaTgCGgC
                  | ||||||  |    ||||     ||| ||  ||||||||||||| || ||  |  | | |
cdg2       1063  TGGTGTGGGAtgGCTACgcCTCGCTGGCCCGCTCGCTGGGGtTGgAGCgGTGCTgTTCGtc
                  |||||||||   ||||||  ||||||   | |||||| |  || ||  |||||  |
cdg3       1047  TGGTGTGGGAcaGCTACcgCTCGCTcGgCatCTCGCTtGGccTGcAGCaGTGCTtcTgcaC
consensus        TgGTGTGGgAcagCTACc-cTCgcTgggCcgCTCGCTgGGgcTGcAGc-GTGCT-ttcg-C cdg1       1587  gcCggTCATggCtgGtgacGGGCgGGTaAcGGGCaTcTTCGCaCTGTACCTGCGcGagccC
                  |  |||| | |  |    |||| ||| |  |||  |  |||||  || ||||||||||||||  |  |
cdg2       1124  caCCaTCATCtCGCGcaCgGGGCAGGTcAtGGGCgTgTTCGCgCTGTACCTGCGTGgcGAC
                  || ||| | ||||  | |||||||||  | |||||| ||| |||||||||| |||||   |||||  |||
cdg3       1108  gcCCgTCAgCaCGCGttCaGGGCAGGTgAaGGGCaTtTTCGCcCTcTAttcGCGTGaaGAC
consensus        gcCcgTCAtc-CgcGt-c-GGGC-GGT-A-GGGCaT-TTCGC-CTgTAcctGCGtGa-gaC cdg1       1648  aAccagctTggcGCgTGGcCGCAGCGCcTtGTgggGgCgtGCcTGCCcTTCTGCGCGCTGG
                  |            |   | ||| ||||||||| | ||       |  |   |||||  ||||||||||||
cdg2       1185  gAGGcCgaTctgGCcTGGgCGCAGCGCgTgGTctcGaCcaGCATGCCgTTCTGCGCGCTGG
                  |||   |      |   ||| ||||||||| | ||        |||| || |||||||||||||
cdg3       1169  cAGGgCcgcaacaCgTGGcCGCAGCGCaTtGTtgattCgtGCATtCCcTTCTGCGCGCTGG
consensus        -Agg-cc-t---cgCgTGGcCGCAGCGC-TtGT-g-g-CgtGCaTgCCcTTCTGCGCGCTGG cdg1       1709  CgcTgGAGCAGcaCGccACcaagaccCAccTgaCCCAGCTTgCCcgcTatGACAGCCTGAC
                  |  | ||||||||   || ||         ||    | |||||||||| ||   |   ||||||||||||
cdg2       1246  CCaTcGAGCAGAgCGagACGCgccAaCATATCgCCCAGCTTtCCAATTTcGACAGCCTGAC
                  ||  || |||| |    |||| ||  | |||||| ||| |||||||||| ||  |||||||||||||||
cdg3       1230  CCtTtGAaCAGAatGcaACGCaggAgCATATCtCCCAcCTTgCCAATTTtGACAGCCTGAC
consensus        Cc-T-GAgCAGaacGc-ACgcag-a-CAtaTc-CCCAgCTTgCCaatTttGACAGCCTGAC cdg1       1770  CGGcCTGCTCAACCGtggcgCGCTGCAtcgcgTgATgGAagaCaTcATC    gccCagccC
                  |||  |||||||||||||       |||||||| |  | |||   |  ||   |  |          |  |
cdg2       1307  CGGGCTGCTCAACCGCaCgTCGCTGCACAAtaTcATCGAGcGCcTGATCA   tGCgcGgC
                  |||||||||||||||||| | | ||||||||||     | ||||| || | |||||||    || |
cdg3       1291  CGGGCTGCTCAACCGCtCcTCGgTGCACAggTgATCGAGgGCaTGATCAgcaaGCagGat
consensus        CGGgCTGCTCAACCGc-cctCGcTGCAcaa-gTgATcGAgggCaTGATCagc--gCagg-c
```

FIG. 1F

```
cdg1      1828 GGCaACcGCacGcTggCcaTcTTCATGcTcGATATCGACCGtTTCCGCGATATCAACGAtG
               ||| || ||  | |  |  | ||||||| | ||||||||||| ||||||||||||||||| |
cdg2      1365 GGCgACaGCCAGTTctCgcTgTTCATGgTtGATATCGACCGcTTCCGCGATATCAACGAcG
               ||| || | ||||||  | | ||||||| | ||||||||||| ||||||||||||||||| |
cdg3      1352 GGCaACcGgCAGTTtgCcaTcTTCATGcTcGATATCGACCGtTTCCGCGATATCAACGAtG consensus      GGCaACcGccaGtT-gCcaTcTTCATGcTcGATATCGACCGtTTCCGCGATATCAACGAtG cdg1      1889 CGCTcGGCCATGTctATGCCGACCagTTCCTtgTcGAGATCGcagGCCGCATCCGCtccaT
               |||| |||||||||  |||||||||  ||||| | ||||||||   ||||||||||    |
cdg2      1426 CGCTtGGCCATGTgaATGCCGACCgcTTCCTcATaGAGATCGgtcGCCGCATCCGCcatcT
               |||| |||||||||  |||||||||  ||||| || ||||||    ||||||||||     |
cdg3      1413 CGCTcGGCCATGTctATGCCGACCagTTCCTtAtCgAGATCGcagcCCGCATCCGttccaT consensus      CGCTcGGCCATGTctATGCCGACCagTTCCTtaTcGAGATCGcaggCCGCATCCGctccaT cdg1      1950 cGcCAAGGAcGAtTACgTgcTCAGCCGCTCgGGtGGTGATGAGTTCgTggTgGTCGTGCCg
                | ||||||| || ||| | | ||||||||||| || |||||||||||  | || |||||||
cdg2      1487 gGtCAAGGAtGAaTACaTtgTCAGCCGCTCCGGCGGTGATGAGTTCaTcaTcGTCGTGCCt
                | ||||||| || ||| | | |||||||||||| || ||| ||  |  | || ||||| 
cdg3      1474 cGcCAAGGAgGAtTACgTgcTCAGCCGCTCCGGCGGcGACGAaTTCgTggTgGTgGTGCCc consensus      cGcCAAGGA-GAtTACgTgcTCAGCCGCTCcGGcGGtGAtGAgTTCgTggTgGTcGTGCCcdg1      2011 GAtTGCgaaggcaAgCagatCGAGgAAaTTGCCcAcAAgCTGcTCgAaaCCATCGgtcGcC
               || |||      |  |    |||| ||| ||||  | || || ||   | ||||||    ||
cdg2      1548 GAaTGCtCGCAtgAaCgcGCCGAGaAATTTGCCGAGAAcCTGaTCaAcgCCATCGCCAGGC
               || ||| ||||  |  |   ||  | ||||||||   |   ||  |   | ||||  ||| ||
cdg3      1535 GAcTGCcCGCAcaAggaaGCCacagAcTTTGCCGAGcAtCTGcTCgcttCCATgaCCAtGC consensus      GA-TGC-cgcacaAgca-gcCgaggAatTTGCCgAgaA-CTGcTCga--CCATcgccaggC cdg1      2072 CGCTcCAGaTcGGgcAGAAtACGCTgtctATCTCGTGCTcgaTcGGCATCAGCACtTTCCC
               |||| ||| | ||  |||||  |||||   |||||||||  | ||||||||||||| |||||
cdg2      1609 CGCTGCAGgTgGGCgAGAACACGCTcAgCATCTCGTGCTgCgTTGGCATCAGCACCTTCCC
                |  |||||| |    ||||| ||||| |  ||||||||  |  ||||||||||||| |||
cdg3      1596 CcaTGCAGaTtGGCcAGAACACGCTgAcCATtTCaTGCTcCaTTGGCATCAGCACCTaCCC consensus      CgcTgCAGaT-GGccAGAAcACGCTgaccATcTCgTGCTccaTtGGCATCAGCACcTtCCC Cel-141
                                      _____→
cdg1      2133 CGCCAACGGGCCGGACAGCGAATCCTGCTCAGCCATGCCGATaCCGCcAtgCGgCAGGCC
               ||||||||||||||||||||||||||||||||||||||||||||||||| |||| | ||||||
cdg2      1670 CGCCAACGGGCCGGACAGCGAATCCTGCTCAGCCATGCCGATGCCGCGAccCGCCAGGCC
               || ||||||||||||||||||||||||||||||||||||||||        ||  |||||||||
cdg3      1657 CGatAACGGGCCGGACAGCGAATCCTGCTCAGCaccGCCGATGtgGCGctgCGCCAGGCC consensus      CGccAACGGGCCGGACAGCGAATCCTGCTCAGCcatGCCGATgccGCgatgCGcCAGGCC
```

FIG. 1G

```
cdg1      2194 AAGGAaGACGGGCGcGGCaTcTTCCGCTTcGCCaatCtcGAgAAaAACCAgGTGGCGCAGG
               |||||  |||||||||  |||  |  |||||||||  |||     |  ||  ||  |||||  ||||||||||
cdg2      1731 AAGGAgGACGGGCGtGGCcTgTTCCGCTTtGCCggcCagGAaAAgAACCAaGTGGCGCAGG
               |||||  |||||||||  |||  |  |||||||||  |||     |  ||  ||  |||||  |||||||| |
cdg3      1718 AAGGAaGACGGGCGcGGCgTcTTCCGCTTcGCCaatCtcGAgAAaAACCAgGTGGCGCAaG
consensus      AAGGAaGACGGGCGcGGC-TcTTCCGCTTcGCCaatCtcGAgAAaAACCAgGTGGCGCAgG cdg1      2255 ACCGGCTGGTGCTcGGCTCGGCGCTGCGtGATTCGCTggCgcAGGGCATGCTgcAaCTGcA
               ||||||||||||| |||||||||||||||| ||||||||| |  ||||||||||| | ||| |
cdg2      1792 ACCGGCTGGTGCTgGGCTCGGCGCTGCGcGATTCGCTctCCAAGGGCATGCTCAACCTGaA
               |||||||||||||  ||||||||||||||||  ||||||||  |||||||||||||||||| |
cdg3      1779 ACCGGCTGGTGCTcGGCTCGGCGCTGCGtGATTCGCTggCCAAGGGCATGCTCAACCTGcA
consensus      ACCGGCTGGTGCTcGGCTCGGCGCTGCGtGATTCGCTggCcaAGGGCATGCTcaAcCTGcA cdg1      2316 tTACCAGCCGCAGGTgcgcACCcacACgctCGaaCTcagCGGtGTcGAGGCGCTgTCaCGC
               ||||||||||||||     |||   ||   ||   ||  ||   ||  ||||||||  ||  |||
cdg2      1853 CTACCAGCCGCAGGTcgagACCatgACcggCGgcCTttaCGGgGTgGAGGCGCTcTCGCGC
               ||||||||||||||     |||   ||   ||   ||  ||   ||  ||||||||  ||||||
cdg3      1840 CTACCAGCCGCAGGTgcgcACCcacACgctCGaaCTcagCGGcGTcGAGGCGCTgTCGCGC
consensus      cTACCAGCCGCAGGTgcgcACCcacACgctCGaaCTcagCGG-GTcGAGGCGCTgTCgCGC cdg1      2377 TGGCATCAtCCgcatCTtGGCAAtATCTtcCCCTCgCGCTTCATcGCCGTGGCGGAGGAGA
               ||||||||  ||     || |||||  ||||  |||||  ||||||||||  |||||||||||||
cdg2      1914 TGGCATCAcCCcacgCTgGGCAACATCTatCCCTCcCGCTTCATtGCCGTGGCGGAGGAGA
               ||||||||  ||     || ||||||||||  |||||  ||||||||||  |||||||||||||
cdg3      1901 TGGCATCAtCCgcatCTtGGCAACATCTtcCCCTCgCGCTTCATcGCCGTGGCGGAaGAGA
consensus      TGGCATCAtCCgcatCTtGGCAAcATCTtcCCCTCgCGCTTCATcGCCGTGGCGGAgGAGA cdg1      2438 CcGGCCAGATCGAGGCCATTGGCCGCTGGTCGCTgctcGAgGCcTGCcGCCAGATcGTGAA
               | |||||||||||||||||||||||||||||||||||||  ||  ||  |||  ||||||||  |||||
cdg2      1975 CgGGCCAGATCGAGGCCATTGGCCGCTGGTCGCTtgagGAaGCgTGCaGCCAGATgGTGAA
               | |||||||||||||||||||||||||||||||||||||  ||  ||  |||  ||||||||  |||||
cdg3      1962 CcGGCCAGATCGAGGCCATTGGCCGCTGGTCGCTgctcGAgGCcTGCcGCCAGATcGTGAA
consensus      CcGGCCAGATCGAGGCCATTGGCCGCTGGTCGCTgctcGAgGCcTGCcGCCAGATcGTGAA Ce1-142
cdg1      2499 GTGGGACCGCGACGGCaTcCatGTGCCcACCGTGGCcGTgAACCTgTCtGCCGTGCATTTC
               |||||||||||||||||| | |  ||||| |||||||| || |||| ||  |||||| ||  |||||||||||
cdg2      2036 GTGGGACCGCGACGGCgTgCggGTGCCgACCGTGGCgGTcAACCTcTCcGCCGTGCATTTC
               |||||||||||||||||| | |  ||||| |||||||| || |||| ||  |||||| ||  |||||||||||
cdg3      2023 GTGGGACCGCGACGGCaTcCatGTGCCcACCGTGGCcGTgAACCTgTCtGCCGTGCATTTC
consensus      GTGGGACCGCGACGGCaTcCatGTGCCcACCGTGGCcGTgAACCTgTCtGCCGTGCATTTC
```

FIG. 1H

```
cdg1      2560  CGCAACCGCGcGCTGCCCGAGCACATcGCggcgCTGCTCAAGgACCATaaCCTcAaGCCtt
                ||||||||||| ||||||||||||||| ||   ||||||||| |||||  ||| | |||
cdg2      2097  CGCAACCGCGgGCTGCCCGAGCACATtGCcaacCTGCTCAAGcACCATggCCTgAcGCCgg
                ||||||||||| ||||||||||||||| ||   ||||||||| |||||  ||| | |||
cdg3      2084  CGCAACCGCGcGCTGCCCGAGCACATcGCggcgCTGCTCAAGgACCATaaCCTcAaGCCtt consensus       CGCAACCGCGcGCTGCCCGAGCACATcGCggcgCTGCTCAAGgACCATaaCCTcAaGCCtt cdg1      2621  cgCGCCTGACGGTGGAAAAtACCGAGAGCGTGATGATGGAtAaCAGCcGCGAcACCGAGGA
                   |||||||||||||||| |||||||||||||||||||| |  ||| |||| ||||||||
cdg2      2158  acCGCCTGACGGTGGAAAAtaACCGAGAGCGTGATGATGGACAgCAGCaGCGAgACCGAGGA
                   |||||||||||||||| |||||||||||||||||||| |  ||| |||| ||||||||
cdg3      2145  cgCGCCTGACGGTGGAAAAtACCGAGAGCGTGATGATGGAtAaCAGCcGCGAcACCGAGGA consensus       cgCGCCTGACGGTGGAAAAtACCGAGAGCGTGATGATGGAtAaCAGCcGCGAcACCGAGGA cdg1      2682  aGTGCTcCAgtCgATCCGCAataTcGgctgtGGcCTGTCGATGGATGATTTtGGCACcGGG
                ||||| ||  | ||||||||    |     || ||||||||||||||||| |||||| |||
cdg2      2219  gGTGCTgCAtgCcATCCGCAggcTtGatgtcGGgCTGTCGATGGATGATTTCGGCACgGGG
                ||||| ||  | ||||||||    |     || |||||||||||||||||||||||| |||
cdg3      2206  aGTGCTcCAgtCgATCCGCAataTcGgctgtGGcCTGTCGATGGATGATTTCGGCACcGGG consensus       aGTGCTcCAgtCgATCCGCAataTcGgctgtGGcCTGTCGATGGATGATTTcGGCACcGGG cdg1      2743  TATTCATCGCTCTCGCGGCTcACgCGCCTGCCaCTGACCGAGATCAAGATCGACCGtAGCT
                |||||||||||||||||||| || ||||||||  |||||||||||||||||||||||| ||||
cdg2      2280  TATTCATCGCTCTCGCGGCTgAccCGCCTGCCGCTGACCGAGATCAAGATCGACCGCAGCT
                |||||||||||||||||||| || |||||||||||||||||||||||||||||||||||||
cdg3      2267  TATTCATCGCTCTCGCGGCTcACgCGCCTGCCGCTGACCGAGATCAAGATCGACCGCAGCT consensus       TATTCATCGCTCTCGCGGCTcACgCGCCTGCCgCTGACCGAGATCAAGATCGACCGcAGCT cdg1      2804  TCATCAACGAtTTtGAatAcGACACCAACGCCCAGGCCGTGACCATGGCgGTGATCGGCAT
                |||||||||| ||  |  |  ||||||||||||||||||||||||||||| |||||||||
cdg2      2341  TCATCAACGAcTTCGAGCATGACACCAACGCCCAGGCCGTGACCATGGCaGTGATCGGCAT
                |||||||||| ||||||| |||||||| |||||||||||||||||||||| |||||||||
cdg3      2328  TCATCAACGAtTTCGAGCATGACACCAAtGCCCAGGCCGTGACCATGGCgGTGATCGGCAT consensus       TCATCAACGAtTTcGAgcAtGACACCAAcGCCCAGGCCGTGACCATGGCgGTGATCGGCAT cdg1      2865  CGGCTCGCGGCTGGGCATGACGGTcGTGACCGAAGGCGTcGAgACCGAGCAGCAGCGcgaC
                |||||||||||||||||||||||| ||||||||||||||   |||||||||||||| |  |
cdg2      2402  CGGCTCGCGGCTGGGCATGACGGTGGTGACCGAAGGCGTGGAAACCGAGCAGCAGtGgcgC
                |||||||||||||||||||||||| ||||||||||||||   |||||||||||||| |  |
cdg3      2389  CGGCTCGCGGCTGGGCATGACGGTGGTGACCGAAGGCGTGGAAACCGAGCAGCAGcGcgaC consensus       CGGCTCGCGGCTGGGCATGACGGTgGTGACCGAAGGCGTgGAaACCGAGCAGCAGcGcgaC
```

FIG. 11

```
cdg1      2926  CTgCTGGAGaAAcTcaAcTGCGAcGTGATGCAGGGCTAcctgttcgccaagccgctggcgC
                 II IIIIII II I  I IIIII IIIIIIIIIIIII
cdg2      2463  CTtCTGGAGgAAtTgcAtTGCGAtGTGATGCAGGGCTA                      tC
                 II IIIIII II I  I IIIII IIIIIIIIIIIII
cdg3      2450  CTgCTGGAaaAAcTcaAcTGCGAcGTGATGCAGGGCTA consensus       CTgCTGGAgaAAcTcaAcTGCGAcGTGATGCAGGGCTAcctgttcgccaagccgctggc-c cdg1      2987  cgcaggatcttgaAtcctgGgtgcgccgtggcGgAgcgcctgcggtCattCGtgAaattga
                    I              I        II            I     II I
cdg2      2503  ttttctcgaagccActaccGcCagcggaaCtgGaAaaaTgGttCCgCgaGCGgcAGgagcG
                                                 I   I II  I    I    I
cdg3      2488            CctgttcgCcaagccgcTcGcaCCcgatGatttcGagaaG consensus       ---------------a------g-c--g----c--gga---tcg--cc-catgcgt-aga---g cdg1      3048  gGcagCCcgCgccAagaagggtggcaagcccgaaAgcaGcgGCaaaaaAgacGgtgCccct
                 I II   III II   I          I       I  II    I  I   I
cdg2      2564  TGGcTCCttCcttAttccAacgaCgGcatAgaGCAtgtGGtGCCcCgcACTGGCAcCggTG
                III I  I    I    I       I  II   I   I  II  III II    II
cdg3      2528  TGGaTgCgcCaccAccagAcgatCcGgcaAatGCtgcctGccgCgCcggCTGcCAaaaaTG consensus       tGgatcC--C-ccA--a-a-g--ccg---a--gcagc-gg-gcc-c--actggca-c--tg cdg1      3109  gcagccaaGCcTGCtGctGCaaGccccgcaaCccccgaaAagtCctgaTcTgcTaCgggAt
                II IIII   II  I  II I            I   I    II ★II  I
cdg2      2625  TTTCagGgGCATGCgGgggGCCgGttTgAgTTCatgAcgcATaaCagttTGTTTTTCatTAC
                IIII   I     I         I I       I              IIIIIIII  II
cdg3      2589  TTTC    GtcaAaaaaGaaaaCatccTaAaTTaccaAtaggTcAattaagGTTTTTCgaTcC consensus       tttc--g-gcatgc-G--gccagcct-a-ttccc-a-a-at-ac-t-atgTttTtCg-tac cdg1      3170  aGATggagccatacgcCATGtCAcTcaAgCACGATGATCGcCTGCGcGCgCTGACcCACCA
                 III            IIII II I  I IIII▼IIIIII IIIII II IIIIII IIIII
cdg2      2686  GGATtCcAGGcgggAaCATGgCAtTgCAaCACGATGATCGGCTGCGgGCCCTGACgCACCA
                 I II I III     I   IIII   II II III I IIIIIIII IIIII II II I
cdg3      2648  GtATcCgAGGtaacAgaATGtCcgcaCcgCAtGATaAcaGGCTcCGcGCCCTtACaCAtgA consensus       ggAT-c-agg--aca-cATGtCa-t-cagCAcGATgAtcGgCTgCGcGCcCTgAC-CAccA cdg1      3231  GGATtCGGATTTCTGGGCcGATgTtGTgGAcAATGTCCTgATcGTgGCcATTACcGATgtg
                IIIII IIIIIIIIIIII III I II II IIIIIIIII II II II IIIII III
cdg2      2747  GGATGCGGATTTCTGGGCtGATcTGGTtGATAATGTCCTcATTGTcGCGATTACgGATaGC
                IIIII II IIIIIIIII II  IIII IIIIIIIIIIIII IIIII III I II II  II
cdg3      2709  aGATGCcGAcTTCTGGGCgGAcgTGGTgGATAATGTCCTtATTGTtGCGgTcACcGAccGC consensus       gGATgCgGAtTTCTGGGC-GAtgTgGTgGAtAATGTCCT-ATtGT-GCgaTtACcGAt-gc
```

FIG. 1J

```
cdg1       3292  cgtGGtGTgATtACCTAtGTGAATGACCGCTTTTGCGAGATcAGCCgcTACcCGCGtGAaG
                 ||  || || ||||||  ||||||||||||||||||||||||| ||||  ||| |||| || |
cdg2       2808  gAGGGgGTCATcACCTACGTGAATGACCGCTTTTGCGAGATaAGCCAGTACTCGCGcGAGG
                 ||||  ||||  |||||||| |||||    || |||||||||  ||||||||| || ||  ||||
cdg3       2770  aAGGGcaTCATtACCTACGTcAATGAtaaaTTcTGCGAGATcAGCCAGTAtTCcCGtGAGG
consensus        -agGG-gTcATtACCTAcGTgAATGAccgcTTtTGCGAGATcAGCCagTActCgCGtgAgG cdg1       3353  AACTGcTGGGggCGACGCAtCGcATCGTCAATTCCGGgTAtCATGATGCgagcTTcTTCaG
                 ||||| ||||     |||||||| ||  ||||||||||||||||  ||  |||||||| |   || ||| |
cdg2       2869  AACTGgTGGGatCGACGCAcCGgATCGTCAATTCCGGCTAcCATGATGCcGatTTtTTCCG
                 ||||| ||||       || || || |||  | || || ||| | ||| |       |  || |||||
cdg3       2831  AACTGcTGGGccatACcCAtCGcATCCtGAAcTCgGGCgAgCACGggaagGccTTcTTCCG
consensus        AACTGcTGGG--cgACgCAtCGcATCgTcAAtTCcGGctA-CAtGatgcgg-cTTcTTCcG cdg1       3414  GcAgaTGTACCGCACCATCcgGGgGGGcgAgaTaTGGCGcGGCAATATCTGCAACCGgGCC
                 | |  ||||||||||||||||| || |||  |    |     ||||| |||||||||||||||| |||
cdg2       2930  GGAtcTGTACCGCACCATCaaGGCGGGGcAacTgTGGCGgGGCAATATCTGCAACCGCGCC
                 || ||||||| ||| |       |||| |    |||   ||||||| | ||||||||||||
cdg3       2892  cGAgaTGTACCagACCcTgttctCGGGcCgcaccTGGtatGGCAATtTgTGCAACCGCGCC
consensus        ggAgaTGTACCgcACCaTc--ggcGGGcca-at-TGGcg-GGCAATaTcTGCAACCGcGCC cdg1       3475  AAGGATGGcaCGCTGTACTGGGTGGCCACCACCATCATgCCCAAGcaCaAActcGCttGGCg
                 ||||||||      |||||||||||||||||||||||||||| ||||||  | ||  ||  |||
cdg2       2991  AAGGATGGgtCGCTGTACTGGGTGGCCACCACCATCATtCCCAAGatCgACcgGCAGGGCa
                 ||||||||       |  |||||||||||||||||||||| ||   |   |   |||||
cdg3       2953  AAGGATGGcagcCacTACTGGGTGGCCACCACCATCATgCCgcAccgCaAtgccaAGGGCg
consensus        AAGGATGGcacgCtgTACTGGGTGGCCACCACCATCATgCCcaAgc-CaAc-cgcagGGCg cdg1       3536  CGgTTgaGGGcTATGTcGCgAcCCGtTTCGAGATTACCGAACTgATGAACACcCGCGACCG
                 ||  ||   |||  || ||| ||   |||||||| ||||||||| ||||||||  |||||||
cdg2       3052  CGATTACGGGgTATGTGGCCAGCCGGTTCGAGATTACCGAACTcATGAACACgCGCGACCG
                 |||||||      ||||| ||||||||  || || || ||||||  ||||||||       | |||
cdg3       3014  aGATTACcGGtTtcGTGGCCAGCCGGTTtGAaATcACgGAACTgATGAACACcaagGtCCG
consensus        cGaTTacgGG-TatGTgGCcAgCCGgTTcGAgATTAccGAACTgATGAACACccgcGaCCG cdg1       3597  GCTcaagtcgCTtGCCGcGACCGAccCgCTGACgGGgCTGtTCAACCGtGGtGGCTTCAAC
                 |||           || |||| ||||||  | |||||| || ||| |||||||| || |||||||||
cdg2       3113  GCTgtgtgAACTGGCCGaGACCGAtaCcCTGACCGGcCTGCTCAACCGcGGCGGCTTCAAC
                 |||       ||| |||||| ||||||            ||||||||| |||||||||||||||||||
cdg3       3075  GCTcaagaAACaGGCCGcGACCGAcgtgCTGACCGGgCTGCTCAACCGtGGCGGCTTCAA
consensus        GCTcaag-aaCtgGCCGcGACCGAc-cgCTGACcGGgCTGcTCAACCGtGGcGGCTTCAAc
```

FIG. 1K

```
cdg1        3658  A   acgTGctCcAgaccgcaGtGgaagataaatcGCaGaaCATtaCCcgCgACatcatgC
                  I    I  I I      I I             III I  III  II I III      I
cdg2        3174  AcgGCgcTGgcCGAtgagatcGcGcgctgCcgCgAGCcGggCATgACCGcCCACCcGGCaC
                      II  I                         I III        III  I  I III  I
cdg3        3135       tGCcagccttGtcaccgcactcgagaaCgcCaAGCgaccgcaccCCgagCcgCaGGCgC consensus         ac-gcc-tgctcga-accgcagtgga--ac---c-aGC-g---cat-aCCg-ccacc-ggcgC cdg1        3716  TgGtCATGTTCGAtCTCGATGGCTTCAAGCAGATCAAcGACaTtCATGGCCACCATGCGGG
                  I I IIIIIIIII IIIIIIIIIIIIIIIIIIIIIIII III I IIIIIIIIIIIIIIII
cdg2        3235  TtGcCATGTTCGACCTCGATGGCTTCAAGCAGATCAATGACgTgCATGGCCACCATGCGGG
                  I I IIIIIIIIIII II II IIIIIIII I I IIIIII I IIIIIIIIIIIIIIIII
cdg3        3194  TgGtCATGTTCGACCTtGAcGGgTTCAAGCcGgTtAATGACaTcCATGGCCACCATGCGGG consensus         TgGtCATGTTCGAcCTcGAtGGcTTCAAGCaGaTcAAtGACaT-CATGGCCACCATGCGGG cdg1        3777  cGAtgTgGTGCTGaagGtgATTtCCaacCGcCTtcTgGcGCTTgtCCACCCtGAaGATgCG
                  II I IIIIIII I III II  II II I I IIII IIIIII II III II
cdg2        3296  tGAcaTcGTGCTGcgtGccATTGCCtcGCGgCTGATCGAGCTTAcCCACCCCGATGATcCG
                  II   IIIII    III   III  III IIIIIIIIIII I   IIIIIIIIII  II
cdg3        3255  cGAtgagGTGCTcaagGtaATcGggcaGCGcCTGATCGAGCTgAtCggCCCCGATGATgCG consensus         cGAtgtgGTGCTgaagGt-ATtgcc-agCGcCTgaTcGaGCTtatCcaCCCcGAtGATgCG cdg1        3838  GTCtGCCGGCTGGGgGGCGATGAGTTTGCgcTCATCCTcaACCatACGCTgcAtaAatTtc
                  III IIIIIIIIII IIIIIIIIIIIII IIIIIII III IIIII I  I  I
cdg2        3357  GTCAGCCGGCTGGGTGGCGATGAGTTTGCCgTCATCCTGCACCGCACGCTCgAGgAtgTat
                  IIII IIIIIIIIIIIIIIIIIIIIIIII III IIIIIIIII IIIII II II I
cdg3        3316  aTCAGtCGGCTGGGTGGCGATGAGTTcGCCaTCATCCTGCgCCGCAgcCTCaAGctcaTgc consensus         gTCaGcCGGCTGGGtGGCGATGAGTTtGCc-TCATCCTgcaCCgcAcgCTc-Ag-a--T-c cdg1        3899  CGCTTtccCtcatgcTGGAgaagCTGCtGGCCgagCTcGAAgcgCCgATCGAggTgGgcAa
                  IIIII  I        IIII    IIII IIII  II III   II IIIIII I  I  I
cdg2        3418  CGCTTGAGCggtaCaTGGAccgcCTGCAGGCCaTcCTTGAAcgCCCcATCGAtaTcGAgAc
                  IIII III   I I  I     IIIII I I IIIIIII II III   II III    I II
cdg3        3377  CGCTcGAGaccatCcTGacCaaggTGCAGaaCcTgCTTGAAgagCCgATCatgcTgGACAg consensus         CGCTtgagc-catccTGgacaagcTGCaGgcC-tgCTtGAAg-gCCgATCgag-TgGacAcdg1        3960  caccAtGGTcAaCGTgtCGGGCAGcATcGGgGtcaccCccaTCGccaGCcagGAaAgtgcc
                      I IIII III  III IIIIIIII II II          I      III  II
cdg2        3479  gGtaACGGTGAGCGTtgCGGGCAGtATtGGcGCggtGCtGcTCGatGGCaCCGACACGaTg
                     II IIIIIII II  IIIIIIII II IIII   II     II II  IIIIIIIII
cdg3        3438  tGccACGGTGcGCaTatCGGGCAGcATcGGgGCcacGCcGaTCacgGGggCCGACACGcTt consensus         -gccAcGGTgagCgT-tCGGGCAGcATcGGgGccacgCcgaTCgc-gGc-ccGAcAcg-t-
```

FIG. 1L

```
cdg1      4021 GAAtcgcTGCAGAAAAAtGCCGAtATcGCGcTtTAtGCcGCCAAGCGCGCGGGtGGCcAcC
               |||   ||||||||||| |||||  |  ||| |  || ||  || ||||||||||||| ||| | |
cdg2      3540 GAAGaCgTGCAGAAAAACGCCGAcATGGCGaTgTACGCtGCCAAGCGCGCGGGCGGCAAgC
               || | | ||||||||||||| ||  |||||  | |||||  |||||||       |||||||||| |
cdg3      3499 GAgGgCcTGCAGAAAAACGCgGAtgTGGCGgTcTACGCcGCCAAGCagtCGGGCGGCAAaC consensus      GAag-ccTGCAGAAAAAcGCcGAtaTgGCG-T-TAcGCcGCCAAGCgcgCGGGcGGCaA-C cdg1      4082 AGgCGCgcATGTTtgaCAtGAcCCTGCaCcAGCatGCgCtGGaGCGgGcgcaGATCCTcAa
               || |||  |||||     || || ||||| |  |||  || ||| ||| |||| |       |||||| |
cdg2      3601 AGtCGCagATGTTCACCAgGAaCCTGCgCgAGCgCGCaCaGGcGCGtGtCtcGATCCTGAg
               || |||   |||||||||  || |||||| | ||  | |   |  || ||| | |  |||||||||
cdg3      3560 AGgCGCgcATGTTCACgccGAgCCTGCaCaAGacCaCgatGGaGCGgGcCaaGATCCTGAc consensus      AGgCGCgcATGTTcacca-GA-CCTGCaC-AGc-cgCgctGGaGCGgGcc-aGATCCTgAcdg1      4143 tGAtGCGCGtgaaGGGGTgatGaaggACCAGTTCGAGcTtTAcTACCAGCCGATCaTGAAC
               || |||||       |||||  |          |||||||||||| | ||  ||||||||||| |||||
cdg2      3662 CGAGGCGCGgtgcGGGGTcGAGCgCAACCAGTTCGAGGTcTAtTACCAGCCGATCgTGAAC
               |||||||||        ||  ||| ||||  ||||||||||| || |||||||||||||  |  |||
cdg3      3621 CGAGGCcCGcaagGGcGTgGAGCtCAggCAGTTCGAGGTtTAcTACCAGCCcATacTcAAC consensus      cGAgGCgCG--a-GGgGTggaGc-caacCAGTTCGAGgTtTAcTACCAGCCgATc-TgAAC cdg1      4204 TtCAgCACcggcaAGtgcGACCAGATCGAGGCGCTGCTGCGCTGGCAcCACCCgcAGCGCG
               | || |||    ||   |||||||||||||||||||||||||||||||||||| ||||| |||||
cdg2      3723 TgCAaCACGatggAGgTgGACCAGATCGAGGCGCTGCTGCGCTGGCAgCACCCCGAGCGCG
               ||||    |||| |   | || |||  ||| ||| || |||||||||||||||||||| || |
cdg3      3682 gcgcgCACGggccgcaTcGAgCAGgcggAaGCGCTGaTGCGCTGGCAcCACCCCGAtCGgG consensus      t-cagCACgggc-ag-tcGAcCAGatcGAgGCGCTGcTGCGCTGGCAcCACCCcgAgCGcG cdg1      4265 GcCTGCTgGCGGCGGAAagCTTCcgCGAtGTaTTccttGATGCGGctCTgGCgCAGGtcAT
               | ||||||| |||||||||  ||||  ||| || || || |||||||  || || ||||  ||
cdg2      3784 GgCTGCTCGCGGCGGAAGaCTTCtCCGAcGTgTTtaCCGATGCGGgcCTcGCCCAGGcgAT
               | ||||||  |  || || || ||| ||  |||| ||||| ||||| ||||| |||||| ||
cdg3      3743 GcCTGCTCtCcGCtGgcGcaTTtaCCGAtGTcTTTgCCGActCGGctCTgGCCCAGatcAT consensus      GcCTGCTcgCgGCgGaag-cTTc-cCGAtGT-TTt-ccGAtgCGGctCTgGCcCAGgtcAT cdg1      4326 GaGcCCGCGCcTGgTCaAGtCCTTCCaGaatGAcaTGcGgATGTGGAAtacaAgcctCGAc
               | | ||||||| |||| ||| |||||||    || ||| || |||||||     ||  | |
cdg2      3845 GGGGCCGCGCaTGaTCgAGgCCTTCCgGcgCGATgTGtGcATGTGGAAcGAgAaaGGCCAG
               || |||||| | ||| ||||||||||||   ||||| ||| ||||| |||| |     ||||
cdg3      3804 GGaGaCGCatcTtgTgcAGtCCTTCCatgaCGATaTccagAaaTGGAAgGAagcgGGCCtg consensus      GgggcCGCgccTggTc-AGtCCTTCCag-acGAtaTgcggAtgTGGAA-gaaa--ggCcag
```

FIG. 1M

```
cdg1       4387  gCGtatCcCaAcCTgaCCATCAAtCTCTCGCGgcTGGACCTGcTCaatatcGgCTtCCAGa
                  ||  ||   |  | |   ||  |||||||  ||||||||  ||||||||  |   |  || ||||
cdg2       3906  CCGccgCgCCAGCTtGCCATCAACCTCTCGCGcaTGGACCTGaTCcgCgaTGACTACCAGc
                  |||  |   |  |||  ||   |||||||  ||||  |||||||||  |     |||    |  |||
cdg3       3865  CCGagcCtgCgGCTgGCggTCAACCTgTCGCatcTGGACCTGcTaaaCctTGAgcAgCAGa
consensus        cCG---C-ccagCTggCcaTCAAcCTcTCGCg-cTGGACCTGcTcaac-ttGactacCAGa cdg1       4448  atGAcCTTGAGGctgaaaTaaaGCGgcagggtggcaaGgCgGcCgatTacGTGCTGGAAaT
                  ||  ||||||||     |   |||   |   |||        |   |     |  |  ||||||||| |
cdg2       3967  gCGAgCTTGAGGaatcGcTgCGGCGctTCAACaTgtcGCCCGaCAgcTTtGTGCTGGAAGT
                  |||   |   ||  ||      |||||   |     |   | ||   |  ||   ||||||||!
cdg3       3926  tCGAcCTgttcagcgaGaTcCGtgaacTCAACcTtgaaCCCtctActTTcaTtCTGGAAGT
consensus        -cGAcCTtgagg--gagaT-cggcg-ctcaac-t--agcCcgcca-tTtcgTgCTGGAAgT cdg1       4509  atCGGAAagCgTGCTGgcgGGCaGgCGctCCGAtCgtGtgcTgCagcgCCTGCagGAACTG
                  ||  ||   |  ||||||    |||  | ||    ||||   |    |    ||    |||||    ||||||
cdg2       4028  gACGGAAgcCATGCTGCAtGGCCGcCGGGCCGAgCAgGgCaTCCgcaaCCTGCGTGAACTG
                  ||   ||     ||   ||  ||  ||  ||  ||  ||||||  ||        |   ||     ||||||||    ||
cdg3       3987  aACcGAgcagATtCTtCAgGGgCGgCgGGCgGAaaAaaaCcgCCttcgCCTGCGTtcgCTt
consensus        aaCgGAa--caTgCTgcagGGccGgCGggCcGA-ca-g-cctcC--cgCCTGCgtgaaCTg cdg1       4570  agcgaactcGGcTTCCaGcTaaCGCTcGATgATTTCGGgctggcgacgctgccaatctcgg
                                ||  ||||  |  ||    ||||  |||  |||||||
cdg2       4089  gCGcGggcgGGtTTCCGGaTcGCGCTtGATAATTTCGG
                                ||  |    ||   || !|  |   |    ||   |  ||  ||  ||  ||  ||
cdg3       4048  tCGgGaaacGGgTTtgGccTgGCcaTgGAcAAaTTtGG
consensus        -cggga--cGG-TTccggcT-gCgcT-GAtaAtTTcGGgctggcgacgctgccaatctcgg cdg1       4631  ttctgcgcacgatttccttcacgcaggccaagatatcacgcaagctggtCAAGGacattga
                                                                                                  |||||
cdg2       4127                                                                   CAAGG
                                                                                                  | |
cdg3       4086                                                                   ttAcG
consensus        ttctgcgcacgatttccttcacgcaggccaagatatcacgcaagctggtcaAgGacattga cdg1       4692  aaccagcccgcaggcgcgcggcgtggtggcGCATCtgattggtctggcacatgcgttcGgG
                                                                     |||||                                                    ||| |
cdg2       4132                                                GCATC                                                  acGGtG
                                                                     |||                                                         |
cdg3       4091                                                GCA                                                      cagtGcgc
consensus        aaccagcccgcaggcgcgcggcgtggtggcGCAtctgattggtctggcacatgc--tgggg
```

FIG. 1N

```
cdg1      4753  CTGAgcgtgaccgtgagcggcgtggaaACCAaaggccagatggaggtCCTGCGCGAgatgg
                ||||                         ||||                ||||||||||
cdg2      4143  CTGA                         ACCA                CCTGCGCGA     A
                ||                              |                ||||  | ||    |
cdg3      4102  CT                           ttcC                acCCTGgGgGA    A consensus       CTgagcgtgaccgtgagcggcgtgg--aCcaaaggccagatggag--CCTGcGcGAgatga cdg1      4814  gTGCCGaccgaattcagggttttatatTTCTCccccgatttctgctGCgaaTCttGtgCt
                |||||                      |||||               ||   ||  |  |
cdg2      4161  CTGCCG                     TTCTC               GCaggTCaaGatCg
                ||||||                     |||
cdg3      4120  CTGCCG                     TTC consensus       cTGCCGaccgaattcagggttttatatTTCtccccccgatttctgctgc---tc--g--c- cdg1      4875  tgCgGAGCAcatcattgcgccagatcataccgagatcacgttacaggcgtcatgacacgcc
                  | |||||
cdg2      4186  acCaGAGCA cdg3      4129 consensus       --c-gagcacatcattgcgccagatcataccgagatcacgttacaggcgtcatgacacgcc cdg1      4936  atgcgccttactttatacaccGACTActccattcgaacccttatctAcCtTGGGCAgaACC
                                     |||||                     | | ||||||||  |||
cdg2      4195                       tggtGACTA                   acAtCgTGGGCA  ACC cdg3      4129 consensus       atgcgccttactttata----gactactccattcgaacccttat--a-c-tgggcagaacc cdg1      4997  CgggtagacgggttgCGATccaggagattgCTGCgacgcaccgcatttcccagaatcatcT
                |              ||||          ||||                             |
cdg2      4219  C              CGAT          gcCTGC                           aT cdg3      4129 consensus       cgggtagacgggttgcgatccaggagat--ctgcgacgcaccgcatttcccagaatcat-t cdg1      5058  GGTCaaggtggtgaaccgtCTGTCCAGCaacggtgtcattctggcgcggcgcgggcgcagt
                ||||                |||||||||
cdg2      4232  GGTC                CTGTCCAGC cdg3      4129 consensus       ggtcaaggtggtgaaccgtctgtccagcaacggtgtcattctggcgcggcgcgggcgcagt
```

FIG. 10

```
cdg1      5119  ggcggccTgGAacTtGccggtGcgccgcACcaGatcaTtAttGgCGAtatcaTccAcctta
                   ||| ||     |       || |   | | | ||   ||
cdg2      4245       ctgaTcGAcaTgGggcagGgcttcaACatGgaagTcAcgGtCGAgggtgTtgAaaacc cdg3      4129 consensus       ggc----t-ga--t-g-----g------ac--g----t-a--g-cga-----t--a----- cdg1      5180  tgGAGgcGgaTatgggCaaaAttGtGtcCtGtaatcctgaaAaCggGcaggcgTgcGTaTt
                   |||    |    |    |  |  | |           |   ||      || |
cdg2      4303  gcGAGCAGTtTgaactCgtcAagGcGctCaGgcccgagcgcAtCcaGggtttCTttGTcTc
                    ||||
cdg3      4129       CAGT consensus       --gagcaGt-t-----c---a--g-g--c-g----------a-c--g------t--gt-t- cdg1      5241  GgCTGatgcaTgTcgCCtGcAaagaCTgtttgccaaatCGgtcaaTGccttcaTGtCGgTa
                 | |||   |  | || |    ||      ||      ||      ||      || ||| |
cdg2      4364  GtCTGcactgTcTtcCCaGgAtattCTCAAGCTgcccgCGcgttttTGaaggggTGaCGcTg
                                           ||||||||
cdg3      4133                        cgCTCAAGCTt consensus       g-ctg-----t-t--cc-g-a----CTcaagct-----cg-----tg------tg-cg-t- cdg1      5302  ctcGatcgcATtacgttgcatgatatcCtGCatGagcctaaGAaactgTaaaatcaGgctc
                   |   ||                  | ||  |        ||      |        |
cdg2      4425  tgaGcgatgATgcgccccgcatggtggCcGCgcGcattggcGAtgaccTgccgcgcGtgga cdg3      4144 consensus       ---g-----at----------------c-gc--g-------ga-----t-------g---- cdg1      5363  atgcAggcAGgctGaaggcAtGtGaCcCgctgTGCATGCGatgcgcatgggattgaaaaat
                     |   ||   |     | | | | |   | |||||||
cdg2      4486  cgtgAttgAGctgGccaatAcGcGgCgCatcaTGCATGCG cdg3      4144 consensus       ----a---ag---g-----a-g-g-c-c----tgcatgcgatgcgcatgggattgaaaaat cdg1      5424  cgcgcgtatcggaatgctcaGtGtcatccAATGATaagcctgacttatgatgagataatat
                                        | |       ||||||
cdg2      4526                        GaGcggcatAATGAT            ggctcgcgcatg cdg3      4144 consensus       cgcgcgtatcggaatgctcag-g------aatgataagcctgacttatg------------
```

FIG. 1P

```
cdg1      5485  ttatctaTaAgTCagGaaGgCTacattttctGGTTGCaataaggacggcatagGtcttTtt
                    ||  | | || ||||||                    |  |
cdg2      4553  cccatgtTcAtTCccGccGcCTcatgggcgcGGTTGC              tGgaacTgc cdg3      4144 consensus       -------t-a-tc--g--g-ct---------ggttgcaataaggacggcata-g----t-- cdg1      5546  tggtgtgGcatGAGGaatttgGctCaCaCagtGtaataaCagGaacaccatgCcccgcacg
                       |  ||||       | | | |   |       |          |
cdg2      4599  attgcacGgggGAGGgcgaccGgcCcCgCctcGcgccctCgcGtgtcatggaCgggctcga cdg3      4144 consensus       -------g---gagg------g--c-c-c---g------c--g---------c-------- cdg1      5607  cCGttgCCTTGGCCtaccgtctgctcctGcATCATGcaggcggcctttaaaagacagggag
                || ||||||||                 |  ||||||
cdg2      4660  gCGcgcCCTTGGCC              GtATCATG cdg3      4144 consensus       -cg---ccttggcctaccgtctgctcctg-atcatgcaggcggcctttaaaagacagggag cdg1      5668  ccagagCCGAGatactaTGCGCCtgacccttcataccgActATGCcattcgtgttctggtt
                      |||||       ||||||               | ||||
cdg2      4682        aCCGAG     gtggTGCGCC              AtgATGC cdg3      4144 consensus       ccaga-ccgagat----tgcgcctgacccttcataccga--atgccattcgtgttctggtt cdg1      5729  tatctggggcaaaaccctGgtcGACGCGtttcagtgcatgaaatttcggaaaatcatggca
                                 |    ||||||
cdg2      4705                  ggcGcagGACGCG cdg3      4144 consensus       tatctggggcaaaac---g---gacgcgtttcagtgcatgaaatttcggaaaatcatggca cdg1      5790  tttcccataatcanctcgtcaggtggggtcaaatcgGCtCtCtacCacgGgTtTnggtcgg
                                                    || |  |   |   | |
cdg2      4718                                      cccttGCgCcCggtCtatGaTgTcacatcc cdg3      4144 consensus       tttcccataatcanctcgtcaggtggggtca-----gc-c-c---c---g-t-t-------
```

FIG. 1Q

```
cdg1      5851  ataCccgTCGGGGggggcagGGggGntttGGaactGccgCGCATGCcgcaTGAaatcgg
                   |   ||||||        ||  ||   |  |||||||   |||
cdg2      4748  gacCtgtTCGGGG       cggaGGaaGggccGGtcgaGatcCGCATGCttgtTGAc cdg3      4144 consensus       ---c---tcggggggg----gg--g----gg----g---cgcatgc----tga-atcgg
```

FIG. 2A

```
pdea1       1                    mpditaltteillpA          LEQAIDATVIIgqeNEiIFyNQAa
                                 |||||||||||              || || |||
pdeq3       1           mskpnlsAeVL        ISA            LEQAIDATVIIDdkNEvIFFNQAg
                          | ||             |||            ||||  |||    ||||
pdea2       1  mpaqvrkmilhgavgrAdVLeftvdqpkISAdvllsamEQAIDpmVvIDehNliIFFNaAa consensus      mpaqvrkmi-------a-vl--------isAdvllsalEQAIDatViId--NeiIFfNqAa pdea1      40  esLWGipraDViGrNVdcLVPTrlrheHDryidRnRetgHNRIVGTSREVEFTRaDGEYIC
               |||    || | || ||||     ||    |   |||||||||||||||||| ||||||
pdea3      39  snLWGldkkDVLGkNVnvLVPTlhqagHDafveRsRgssHNRIVGTSREVEFTRsDGEYIC
                | |    | | ||  |||     ||    |   ||||||||||||   ||| |||||
pdea2      62  ekiWGcsreeVmGrNVscLVPeperdrHDdyinRnRetgvgRIVGTSREVEFrRanGEYvC consensus      e-lWG--r-dv-GrNV-cLVPt--r--HD-yi-RnRetghnRIVGTSREVEFtRadGEYiC pdea1     101  GELSLSKVqigqgDKRltyyMGVMKNVTeESQrRKILILQNDVLQALASDMlIQDigeLiC
               ||||||||   |||    ||||||||| ||| ||||||||||||||||||| |||   | |
pdea3     100  GELSLSKV  VNDDKR IffMGVMKNVTnESQQRKILILQNDVLQALASDMmIQDVaDLLC
               ||||      |||       ||| ||    || |||| ||||||||||||  || | |||
pdea2     123  GELS  isrvqVND  cgkIyyiaVMKdVTeqSrQRKILvLQNDVLQALASDMsIQeVgDLLC consensus      GELSlskv--vnddkr-iyymgVMKnVTeeSqqRKILiLQNDVLQALASDM-IQdvgdLlC pdea1     162  RkVEaFVPnsVAaLlvlddaqpwRVictsaLPpRiRnaLEttvpSpSdvEKLkanasytgh
                | | |||   ||  || |     ||   | |  |    |   |  |  |||    |
pdea3     158  RRVESFVPGtVAvLMLItpdgqLRVlsSPtLPKRYRAsLESlyvSsSeLEKLRvdPkhatr
               ||    ||| | || ||   | |      || |    |      |   ||||    | | |
pdea2     182  RRadSFVPGaVgaLMLIdrsrrLsVsaSPsmPKRYRAaLdSmqltpeqLEmLRanPagsnt consensus      RrvesFVPg-VaaLmlid----lrV--sp-lPkRyRaaLes---sps-lEKlranp----- pdea1     223  lVWnnYqSmcrSLGLQsCyaaPVmagdGrVtGIFALYLREpnqlqaWPQRlVgaClPFCAL
                ||   |  | |||||  |       | |   | ||||||||      |||| |  |||||
pdea3     219  mVWDsYrSLgiSLGLQqCfctPVstRsGQVkGIFALYsREDqgrntWPQRiVdsCiPFCAL
                ||| | |  |||||| |   ||   | | ||||||  |  | |   | |||| |  |||||
pdea2     243  vVWDgYaSLarSLGLerCcsstiisRtGQVmGvFALYlRgDeadlaWaQRvVstsmPFCAL consensus      -VWd-Y-Sl-rSLGLq-C---pv--r-GqV-GiFALYlRed----aWpQR-V--c-PFCAL pdea1     284  AlEQhATktHltqLAryDSLTGLLNR galhrvmedIiaQpGNRtlAIFMLDIDRFRDIND
               |  ||  ||   || |||||||||||      |       |  ||| |||||||||||||||
pdea3     280  AfEQnATqeHIshLANFDSLTGLLNRsSvHkvIEgmIskQdGNRQFAIFMLDIDRFRDIND
                |      |   |   |||||||||||      |    ||  ||   || || |||||||||||
pdea2     304  AiEQseTrqHIaqLsNFDSLTGLLNRtSlHniIE  rlimrgGdsQFslFMvDIDRFRDIND consensus      A-EQ-aT--Hi-qLanfDSLTGLLNR-s-h---ie--ii-q-Gnrqfai FMlDIDRFRDIND
```

FIG. 2B

```
pdea1      344  ALGHVYADQFLvEIAgRIRSIAKdDYVLSRSGGDEFVVVVPDCegKqieeiAhkLLetigr
                ||||||||||| ||| |||||||| ||||||||||||||||||| |       |   ||
pdeq3      341  ALGHVYADQFLIEIAaRIRSIAKeDYVLSRSGGDEFVVVVPDCpHKeAtdFAEhLLasmtm
                ||||| || ||||| |||  ||   |  ||||||||| ||| |  |   | ||| |
pdea2      364  ALGHVnADrFLIEIgrRIRhlvKdeYivSRSGGDEFiiVVPeCsHerAekFAEnLinaiar consensus       ALGHVyADqFLiEIa-RIRsiaKddYvlSRSGGDEFvvVVPdC-hk-ae-fAe-Ll--i-r pdea1      405  PlQIGQNTLsISCSIGISTfPaNGPDSESLLShADtAmRQAKEDGRGiFRFANLEKNQVAQ
                | |||||||| ||||||||| | |||||||||||| | |||||||||| |||||||||||||
pdea3      402  PmQIGQNTLtISCSIGISTyPdNGPDSESLLStADvAlRQAKEDGRGvFRFANLEKNQVAQ
                | | ||| ||| |||| | ||||||||||||| || |||||||||| |||   ||||||||
pdea2      425  PlQvGeNTLsISCcvGISTfPaNGPDSESLLShADaAtRQAKEDGRGlFRFAggEKNQVAQ consensus       PlQiGqNTLsISCsiGISTfPaNGPDSESLLShAD-A-RQAKEDGRG-FRFAnlEKNQVAQ pdea1      466  DRLVLGSALRDSLAqGMLqLHYQPQVRTHTLELSGVEALSRWHHPHLGNIFPSRFIAVAEE
                |||||||||||||| ||| ||| ||| |||||||||||||||||||||||| ||||||||||
pdea3      463  DRLVLGSALRDSLAKGMLNLHYQPQVRTHTLELSGVEALSRWHHPHLGNIFPSRFIAVAEE
                ||||||||||||| |||||| ||||| | |  ||||||||||||||| |||| ||||||||||
pdea2      486  DRLVLGSALRDSLsKGMLNLnYQPQVeTmTggLyGVEALSRWHHPtLGNIyPSRFIAVAEE consensus       DRLVLGSALRDSLakGMLnLhYQPQVrThTleLsGVEALSRWHHPhLGNIfPSRFIAVAEE pdea1      527  TGQIEAIGRWSLLEACRQIVKWDRDGIHVPTVAVNLSAVHFRNRALPEHIAALLKDHNLKP
                ||||||||||||||||||||||||||||||||||||||||||||||||||||||||||||
pdea3      524  TGQIEAIGRWSLLEACRQIVKWDRDGIHVPTVAVNLSAVHFRNRALPEHIAALLKDHNLKP
                |||||||||||| ||||  ||||||||| |||||||||||||||| |||||| ||| | |
pdea2      547  TGQIEAIGRWSLeEACsQmVKWDRDGvrVPTVAVNLSAVHFRNRgLPEHIAnLLKhHgLtP consensus       TGQIEAIGRWSLlEACrQiVKWDRDGihVPTVAVNLSAVHFRNRaLPEHIAaLLKdHnLkP pdea1      588  SRLTVEITESVMMDNSRDTEEVLQSIRNIGCGLSMDDFGTGYSSLSRLTRLPLTEIKIDRS
                ||||||||||||||||||||||||||||||||||||||||||||||||||||||||||||
pdea3      585  SRLTVEITESVMMDNSRDTEEVLQSIRNIGCGLSMDDFGTGYSSLSRLTRLPLTEIKIDRS
                 ||||||||||||| |||| |  || |  ||||||||||||||||||||||||||||||||
pdea2      608  dRLTVEITESVMMDsSseTEEVLhaIRrldvGLSMDDFGTGYSSLSRLTRLPLTEIKIDRS consensus       sRLTVEITESVMMDnSrdTEEVLqsIRnigcGLSMDDFGTGYSSLSRLTRLPLTEIKIDRS pdea1      649  FINDFEyDTNAQAVTMAVIGIGSRLGMTVVTEGVETEQQRDLLEKLNCDVMQGYLFAKPLA
                ||||| ||||||||||||||||||||||||||||||||||||||||||||||||||||||
pdea3      646  FINDFEHDTNAQAVTMAVIGIGSRLGMTVVTEGVETEQQRDLLEKLNCDVMQGYLFAKPLA
                ||||||||||||||||||||||||||||||||||||||||   || || ||||||||| |||
pdea2      669  FINDFEHDTNAQAVTMAVIGIGSRLGMTVVTEGVETEQQwrLLEeLhCDVMQGYLFsKPLp consensus       FINDFEhDTNAQAVTMAVIGIGSRLGMTVVTEGVETEQQrdLLEkLnCDVMQGYLFaKPLa pdea1      710  PqdleswvrrggapavlReieaaarakkggkpessgkkdgAPAAKpaaaspaTpeks.
                |                   ||                     |||||          |
pdea2      707  P     ddfEKWmrhhqtIR             QmlpaAPAAKnvsskkkTs.
                |     |||           |            |
pdea3      730  P     aelEKW     freR            Qergsfliptta.

consensus       Pqdl---ekw------iReieaaarakkggkpessq----apaak-a-----t--ks.
```

FIG. 3A

```
dgc1      1 MSlkHDdRLRALTHqDsDFWADVVDNVLIVAiTDvrGvITYVNDrFCEISrYpREELLGaT
            || || |||||||| | ||||||||||||| || | |||||| ||||| | |||||| |
dgc3      1 MSapHDnRLRALTHeDADFWADVVDNVLIVAvTDrkGiITYVNDkFCEISQYSREELLGhT
            |  || |||||||| ||||||| |||||||| || | |||||| |||||||||||| | |
dgc2      1 MalqHDdRLRALTHqDADFWADlVDNVLIVAiTDseGvITYVNDrFCEISQYSREELvGsT consensus   Msl-HDdRLRALTHqDaDFWADvVDNVLIVAiTD--GvITYVNDrFCEISqYsREELlG-T dgc1     62 HRIvNSGyHdasFFRqMYrTirgGeiWrGNiCNRAKDGtlYWVATTIMPkhNslGaveGyV
            ||| ||| |   ||| || ||  |   | |||||||||  |||||||| |  |    ||
dgc3     62 HRIlNSGeHgkaFFReMYqTlfsGrtWyGNlCNRAKDGShYWVATTIMPhrNakGeITGfV
            ||| ||| |   ||| || ||   |  | |||||||||  |||||||| |    |||||
dgc2     62 HRIvNSGyHdadFFRdlYrTikaGqlWrGNiCNRAKDGSlYWVATTIiPkidrqGtITGyV consensus   HRIvNSGyHda-FFR-mYrTi--G--WrGNiCNRAKDGslYWVATTImPk-n--G-itGyV dgc1    123 AtRFEITELMNTrdRLKslAATDpLTGLfNRGGFN nvLqTAvEdksqnitrdimLVMFDL
            | |||||||||| ||| | |||| |||| |||||  | | | | |             ||||||
dgc3    123 ASRFEITELMNTkvRLKkqAATDvLTGLLNRGGFN AsLvTAlEnakrphpepqALVMFDL
            |||||||||||| || | |||| |||| |||||     |  |                || ||||
dgc2    123 ASRFEITELMNTrdRLcelAeTDtLTGLLNRGGFNtAladeiarcrepgmtahpALaMFDL consensus   AsRFEITELMNTrdRLk-lAaTD-LTGLlNRGGFNta-l-ta-e------t---aLvMFDL dgc1    183 DGFKqiNDIHGHHAGDvVLKVIsnRLlaLvhPeDAvcRLGGDEFAlILnhtLhkfaLslmL
            ||||  ||||||||||  ||||  |||    |||  |||||||| || ||  |  | | |
dgc3    183 DGFKpvNDIHGHHAGDeVLKVIggRLIELigPDDAiSRLGGDEFAiILrRsLklmpLEtiL
            ||||  || ||||||||   |||     |||  ||||||||||| ||    |  ||
dgc2    184 DGFKqiNDvHGHHAGDiVLralasRLIELthPDDpvSRLGGDEFAvILhRtLedvsLErym consensus   DGFKqiNDiHGHHAGD-VLkvI--RLieL-hPdDavsRLGGDEFA-IL-rtL----Le--l dgc1    244 eKllaeLEaPIevgntmVnvSGSIGvTPIasqesaEsLQKNADiAlYAAKraGGhQARMFd
             | ||  ||||    |||  ||||| ||| | |   ||||||| |||||| || ||||| 
dgc3    244 tKvQnlLEePImldsaTVriSGSIGATPItGaDTlEgLQKNADvAvYAAKqsGGKQARMFT
             | || ||||| ||  || ||||| || | || | |||||||  |||||| ||| ||| 
dgc2    245 drlQaiLErPIdietvTVsvaGSIGAvlldGtDTmEdvQKNADmAmYAAKraGGKQsqMFT consensus   -klqa-LE-PI-----tV-vsGSIGatpi-g-dt-E-lQKNAD-A-YAAKraGGkQarMFt dgc1    305 mtLHqhalERAqILndAReGVmkdQFElYYQPImNfsTGkcdQiEALlpWHHPqRGLLaAe
              ||   | ||| || ||  || | ||| |||||| |  ||   | |||  ||||| |||||
dgc3    305 psLHkttmERAkILtEARkGVElrQFEVYYQPIlNarTGrieQaEALmRWHHPdRGLLSAg
                | || || ||| || || | ||||||||| | ||   ||||| | || |||||| |
dgc2    306 rnLreraqaRvsILsEARcGVErnQFEVYYQPIvNcnTmevdQiEALlRWqHPeRGLLaAe consensus   --Lh--a-eRa-IL-eAR-GVe--QFEvYYQPI-N--Tg--dQiEALlrWhHP-RGLLaAe
```

FIG. 3B

```
dgc1       366 sFrDVFIDaALAQvMsprLVkSFqnDmrmWntsldaypnLtiNLSrLgLLNigfQnDLeaE
                   ||||| |||| |  || ||| |   |  ||  ||| ||||| || |   | ||
dgc3       366 aFtDVFaDsALAQiMethLVqSFhdDiqkWkEaGlPslrLAvNLShLDLLNleqQiDLfsE
                   ||||| |||    ||  |||   |  |    |  ||  || ||  || |    | |
dgc2       367 dFsDVFtDagLAQaMgprmieaFrrDvcmWnEkGqPprqLAiNLSrmDLirddyQreLees
consensus      -F-DVF-DaaLAQ-M-prlv-sF--D--mWne-g-p---LaiNLSrldLln---Q-dLe-e dgc1       427 IkrqggkaadyvLEisEsvLaGRRsdrvlqRLqeLSelGFqLtlDdFGlaTlpiSvLrtis
                 |          ||  |  | |||    ||  ||  ||  | ||  |   ||  |||
dgc3       427 IRelNlePstFiLEVTEqiLqGRRAEknrlRLRsLSgnGFgLAmDkFGyGTvrLStLgELP
                 |  |      |||||||  ||||||      || ||  ||    ||  |   |  |||
dgc2       428 lRrfNmsPdsFvLEVTEamLhGRRAEqgirnLReLaraGFriAlDnFGKGitvLnhLrELP
consensus      irr-n--p--fvLEvtE--L-GRRae----rLreLs--GF-lalD-FG-gt--ls-Lrelp dgc1       488 FtqaKi
                | |
dgc3       488 FqslKl
                |  |
dgc2       489 FsqvK
consensus      F-q-K-
```

FIG. 4

```
  1   ..............MSLVQPSLSSDGTKRTFSERQEFMTEDMPASMHFHV  36
                    |...:.|:.    |:... .|: .::  ... ::|
  1   MYAAAQAKPQSIEVEHLGPAPMSGPRLVATYKPGREIYAQGDLNDKCYQV  50

37   VSGGARLFKSLPDGRPQIIGFAHKGDVLPAYPCTRYHYSAEAMRSLQVVC  86
       .|:.|::: |.|||.|:::|   .|:::.   .....  |||:.  :.
 51   STGAVRIYRLLSDGRRQVVSFHLPGEMFGFEAGSNHSFFAEAITETTLAI 100

87   VPAPYLSHLHETSPGACAASLNSARQLLVSLHARLLMLGRQTARERLATF 136
      ...   :::| |.:   | .|.:    :... :.:||:||||:| ||:|.|
101   FGRR...NMQERSRELLALALTG....MARAQQHLLVIGRQCAVERIAAF 143

137   LLGQGTRMGPGELWPVDPSISRADMADFLGLTTETVSRLLSAFHREQLIC 186
      |::  ..| |.|   :..  .:||.|:||||||.||||::..  :.   ||.
144   LVDLCERQGGG..RQLRLPMSRQDIADYLGLTIETVSRVVTKLKERSLIA 191

187   .RERRAIHILDPDRLRAIVAHPE* 209
       |: |.|...:.|: ||.:..
192   LRDARTIDIMKPEALRSLCN*... 212
```

FIG. 5

```
  1   ..................MRLTLYTDYSIRTLIYLGQNP.GRRVAIQEIA  31
                        :.|||:|||::|.|||::  | ||...| |:.
651   WFIININVFFPDFPFEVDVQLTSFTDYGLRALIYMASLPEGRMTSISEVT 700

32   ATHRISQNHLVKVVNRLSSNGVILARRGRSGGLELAGAPHQIIIGDIIHL  81
      ... :|.||:||::|.||..| :|:..||: |:  | |||||:.::||.
701   DVYGVSRNHMVKIINQLSRAGYVTAVRGKNGGIRLGKPASAIRIGDVVRE 750

82   MEADMGKIVSCNPENGQACVLADACRLQGLFAKSVNAFMSVLDRITLHDI 131
      :|   .:|.|...|       |  :::. |||.. :.|.|...|::  ||..||  |:
751   LEP..LSLVNCSSE...FCHITPACRLKQALSKAVQSFLTELDNYTLADL 795

132   LHEPKKL*......................................... 139
      :.|  ..|
796   VEENQPLYKLLLVE*
```

CYCLIC DI-GUANYLATE METABOLIC ENZYMES

This is a continuation of application Ser. No. 07/800,218, filed Nov. 29, 1991, now abandoned.

FIELD OF THE INVENTION

The invention relates to the field of recombinant DNA techniques for the production of proteins and the manipulation of metabolic pathways. More specifically, this invention relates to the cloning of diguanylate cyclase operons, the expression and regulation of the operons, and methods of using the operons for modifying the production of cellulose in microorganisms.

BACKGROUND OF THE INVENTION

Cellulose is relied upon as the raw material for a number of useful products including paper products and wound dressings. Cellulose may be obtained from plants and various microorganisms in culture, for example from the cellulose producing bacteria of the genus Acetobacter. Acetobacter is characteristically a Gram-negative, rod-shaped bacterium 0.6–0.8 μm by 1.0–4 μm. It is strictly aerobic; metabolism is respiratory, never fermentative. It is further distinguished by the ability to produce multiple poly β(1–4) -glucan chains, chemically identical to cellulose. Multiple cellulose chains or microfibrils are synthesized at the bacterial surface at sites on the cell wall. The production of cellulose by Acetobacter has been the subject of intense study since at least the 1930's. In particular, *Acetobacter xylinum* has been widely studied to attempt to elucidate the mechanism of cellulose synthesis in intact cells [Schramm and Hestrin, (1954) *J. Gen. Microbiol.* 11:123–129].

The enzymatic pathway for cellulose synthesis in *Acetobacter xylinum* has been investigated and essentially four enzymatic steps have been characterized in cell-free extracts of *A. xylinum* which appear to comprise the complete pathway from glucose to cellulose. These are the phosphorylation of glucose by glucokinase [Benziman, et al., (1972) *J. Bacteriol.*, 111:325–330], the isomerization of glucose-6-phosphate to glucose-1-phosphate by phosphoglucomutase [Gromet, et al., (1957) *Biochem. J.*, 67:679–689; Frei-Roitman, Factors affecting the activity of phosphoglucomutase and UDP-glucose pyrophosphorylase of *Acetobacter xylinum*, M.Sc. thesis, The Hebrew University of Jerusalem, Jerusalem, Israel (1974)]; the synthesis of uridine 5'-diphosphoglucose (UDP-glc) by UDPG-pyrophosphorylase, [Frei-Roitman, supra; Swissa, Biosynthesis of cellulose in *Acetobacter xylinum*, Ph.D. thesis, The Hebrew University of Jerusalem, Jerusalem, Israel (1978)], and the cellulose synthase reaction.

The novel nucleotide activator c-di-GMP, i.e., cyclic diguanosine monophosphate is essential for the high activity of cellulose synthase. Ross et al., *Nature* 325:279–281 (1987); Ross et al., *Carbohyds Res.* 149:101–117 (1986). Studies of cell-free preparations from *A. xylinum* have given rise to a model in which c-di-GMP functions as a reversible, allosteric activator of the membrane-bound cellulose synthase, the enzyme that performs the "committed" step in cellulose biosynthesis. The concentration of c-di-GMP, the net result of the ongoing synthesis and degradation of c-di-GMP is controlled by the opposing action of the associated enzymes which together account for these two pathways. Diguanylate cyclase (abbreviated as DGC) catalyzes the synthesis of c-di-GMP from two molecules of GTP, via the linear dinucleotide triphosphate pppGpG, in two distinct, pyrophosphate-releasing steps. Within the cell, inorganic pyrophosphate is rapidly cleaved to yield orthophosphate, Benziman and Palgi *J. Bacteriol*, 104:211–218 (1970). The pathway of c-di-GMP degradation is initiated by a c-di-GMP - specific, $Ca^{++}$-sensitive phosphodiesterase A, PDE-A, which cleaves a single phosphodiester bond in the cyclic structure, yielding the linear dimer pGpG and simultaneously inactivating the molecule. The mononucleotide residues of the inactive dimer structure are then recovered as free 5'-GMP units through the action of phosphodiesterase B, PDE-B. The $Ca^{++}$-inhibition of PDE-A may represent an additional locus of regulatory control; according to this model, fluctuations in $Ca^{++}$ levels may modulate the rate of cellulose synthesis as they influence the level of activator in the system.

As with its cyclic mononucleotide-forming counterparts, adenylate-and guanylate cyclase, the diguanylate cyclase of *A. xylinum* appears to occur in both a cytoplasmic and a membrane-associated form.

The pathway of c-di-GMP synthesis attributed to diguanylate cyclase proceeds from GTP via the diguanosine tetraphosphate intermediate pppGpG (115; P. Ross, Ph.D. Thesis, The Hebrew University of Jerusalem, 1990). Each of the two 3'-5'phosphodiester bond-forming, pyrophosphate-releasing steps in the pathway appears to be catalyzed by a single enzyme on the basis that a separate pppGpG - forming activity has not been isolated in the course of purification.

While native diguanylate cyclase appears to be a multi-subunit enzyme, the precise nature of its subunit composition has not been completely ascertained. The enzyme has been purified by ≈2000 fold by affinity chromatography based on an immobilized form of the GTP substrate, Ross, et al., *FEBS Lett.*, 186:191–196 (1985); Ross, et al, *Carbohydr. Res.*, 149:101–117. Polyclonal antibodies raised against two different peptides (61 and 57 kDa, also referred to as bands III and IV, respectively), both highly-enriched in the course of the purification, have been shown to bind to the native enzyme but not to be cross-reactive with respect to the original antigens (P. Ross, Ph.D. Thesis, The Hebrew University of Jerusalem, 1990). Thus the native, soluble form of diguanylate cyclase, which bears a molecular weight of 190 kDa, appears to be a hetero-oligomeric protein.

Two phosphodiesterases, PDE-A and PDE-B, are associated with the C-di-GMP degradation pathway. PDE-A is the more important of the two enzymes in determining C-di-GMP levels because it inactivates c-di-GMP by cleaving the molecule to form pGpG. This form of negative control is irreversible in the sense that, at least within the in vitro system, the pGpG degradation intermediate is not subject to rephosphorylation (in the co-presence of ATP) but rather is rapidly degraded to produce two molecules of 5'-GMP. This latter reaction, catalyzed by the activity of PDE-B, evidently serves a salvage role, regenerating monophosphate units from one round of c-di-GMP formation and breakdown for de novo GTP synthesis.

The $Mg^{++}$-dependent PDE-A and PDE-B reactions have been determined to be distinct enzymes mainly by the criteria of sensitivity to divalent cations, differential degree of intracellular distribution, and immunochemical analysis, in addition to substrate specificity (R. Mayer, MSc Thesis, The Hebrew University of Jerusalem). The ratio of PDE-A to PDE-B activity in membrane preparations is approximately 10:1, while in soluble extracts this ratio is reversed. Anti-sera which effectively inhibits PDE-A activity has no inhibitory or binding effect on the PDE-B enzyme. Furthermore, in contrast to the PDE-B reaction, the $Mg^{++}$- requiring ($K_a \approx 4$ mM) PDE-A activity is inhibited at low ($K_{1/2} \approx 50$ µM) concentrations of $Ca^{++}$-ions. Kinetically, the PDE-A reaction obeys a first order rate pattern ($K_H \approx 0.25$ µM) typical to an enzyme bearing a single substrate-binding site.

The c-di-GMP -specific, $Ca^{++}$-sensitive PDE-A occupies a crucial regulatory role and has been studied in further detail, with particular regard to regulatory properties and substrate specificity. A subunit molecular weight of 85 kDa has been assigned to the membrane-associated PDE-A, which in soluble form displays a native weight of $\approx 190$ kDa. The inhibitory effect of $Ca^{++}$ on the rate of hydrolysis of c-di-GMP appears to result directly from a reduction in the catalytic constant ($V_{max}$) of PDE-A activity, rather than from a Ka effect (Ross et al., *J. Biol Chem* 265:18933–18973 (1990)). The mechanism of inhibition does not appear to be allosteric in nature, as via a specific $Ca^{++}$-binding site which paralyzes the enzyme when occupied, but rather may involve specific interaction with the cyclic dinucleotide substrate. PDE-A activity is sensitive as well to the presence of polyethylene glycol; inhibition of c-di-GMP degradation offers an adequate explanation for the previously reported potentiating effect of this hydrophilic, protein aggregating polymer on the cellulose synthase reaction under cell-free assay conditions.

There is biochemical evidence to suggest that organisms other than Acetobacter possess peptides that are homologous to cdg peptides and cellulose synthase peptides. This evidence is based on detection of c-di-GMP synthetic activity, GDC activity, and cellulose synthase activity in cellulose synthesizing bacteria like *Agrobacterium tumefaciens* and cross reacting activity of antiserum for cellulose synthase bcsB with variety of plant cells. Interestingly, these peptides which cross react with antiserum to the bcsB peptide also bind. UDPG and c-di-GMP in affinity labeling studies. For a review of those experiments see P. Ross, et al., (1991) *Microbiol. Rev.*, 55(1), 35–58.

Given the importance of c-di-GMP in regulation of cellulose synthase activity, the ability to produce recombinant c-di-GMP metabolic enzymes provides useful mechanisms for regulating cellulose synthesis, ultimately providing enhanced cellulose production from cells grown in culture.

SUMMARY OF THE INVENTION

The present invention provides for operons encoding enzymes for the biosynthesis and degradation of c-di-GMP (cyclic-di-guanosine monophosphate), a positive allosteric regulator of cellulose synthase. Three operon sequences isolated from Acetobacter are specifically disclosed: cdg1 (SEQ ID NO: 1), cdg2 (SEQ ID NO: 2), and cdg3 (SEQ ID NO: 3). Those operons contain genes encoding diguanylate cyclase (dgc) and c-di-GMP phosphodiesterase A (pdeA). These operons also contain nucleotide sequences encoding other proteins of interest, including CDG1A (SEQ ID NO: 4) and CDG1D (SEQ ID NO: 7). The nucleotide sequences of cdg operons, including cdg1 (SEQ ID NO: 1), cdg2, (SEQ ID NO: 2) and cdg3 (SEQ ID NO: 3) or portions thereof, find a variety of uses including the preparation of purified compositions of any polypeptide encoded by the operons, vectors containing nucleotide sequences encoding cdg operon proteins, and hybridization probes for the detection of genes encoding cdg operon genes.

Another aspect of the subject invention is to provide for genetically manipulated strains of cellulose producing bacteria, including Acetobacter species, wherein the expression levels of cdg operon encoded proteins is either increased or decreased, thereby modifying the intracellular level of c-di-GMP, and hence cellulose synthase activity and cellulose synthesis, in the cell. Of particular interest is the production of genetically manipulated strains producing elevated levels of CDG activity and/or decreased levels of PDE-A activity.

BRIEF DESCRIPTION OF THE SEQUENCES

SEQ ID No: 1 is the nucleotide sequence the cdg1 operon (SEQ ID NO: 1). The sequence in the figure is 5276 bp in length. The operon is divided into at least 4 identified open reading frames. The first open reading frame, cdg1A, nucleotides 206–829, the second open reading frame, pdeA1, nucleotides 856–3150, the third, dgc1, nucleotides 3184–4923, and the fourth, cdg1D, nucleotides 4933–5346.

SEQ ID No: 2 is the nucleic acid sequence of the cdg2 operon (SEQ ID No: 2). The operon may be divided into at least 2 open reading frames. The first open reading frame pdeA2, nucleotides 98–2353, and the second open reading frame dgc2, nucleotides 2465–4186.

SEQ ID No: 3 is the partial nucleotide sequence of the cdg3 operon (SEQ ID No: 3). The operon may be divided into at least two open reading frames. The first open reading frame is pdeA3, nucleotides 392–2611, and the second partial open reading frame is dgc3, nucleotides 2665–4143.

SEQ ID No: 4 is the deduced amino acid sequence of CDG1A (SEQ ID No: 4).

SEQ ID No: 5 is the deduced amino acid sequence of PDEA1 (SEQ ID No: 5).

SEQ ID No: 6 is the deduced amino acid sequence of DGC1 (SEQ ID No: 6).

SEQ ID No: 7 is the deduced amino acid sequence of CDG1D (SEQ ID No: 7).

SEQ ID No: 8 is the deduced amino acid sequence of PDEA2 (SEQ ID No: 8).

SEQ ID No: 9 is the deduced amino acid sequence of DGC2 (SEQ ID No: 9).

SEQ ID No: 10 is the deduced amino acid sequence of PDEA3 (SEQ ID No: 10).

SEQ ID No: 11 is the deduced partial amino acid sequence of DGC3 (SEQ ID No: 11).

FIG. 1 is a homology comparison between the nucleotide sequences of the cdg1 (SEQ ID NO: 1), cdg2 (SEQ ID NO: 2), and cdg3 (SEQ ID NO: 3) operons Acetobacter.

FIG. 2 is a homology comparison between the amino acid sequences of Acetobacter proteins PDEA1 (SEQ ID NO: 5), PDEA2 (SEQ ID NO: 8), and PDEA3 (SEQ ID NO: 10).

FIG. 3 is a homology comparison between the amino and acid sequences of Acetobacter proteins DGC1 (SEQ ID NO: 6), DGC2 (SEQ ID NO: 9) DGC3 (SEQ ID NO: 11).

FIG. 4 is a homology comparison between the amino acid sequences of the *Rhizobium melliloti* fixK protein and the Acetobacter CDG1A (SEQ ID NO: 4)protein.

FIG. 5 is a homology comparison between the amino acid sequences of the *E. coli* purA protein and the Acetobacter CDG1D (SEQ ID NO: 7) protein.

DETAILED DESCRIPTION OF THE INVENTION

In order that the invention herein described may be more fully understood, the following detailed description is set forth.

A. Definitions

As used herein, the term "Acetobacter" refers to a particular genus of bacteria described in detail in *Bergey's Manual of Determinative Bacteriology*, Buchanan and Gibbons eds., Williams and Wilkins Publishers. The specific strains of Acetobacter from the nucleotide sequences of the subject invention where isolated are Acetobacter 1306-11 (ATCC deposit number 53263) and Acetobacter 1306-21 (ATCC deposit number 53524), the isolation of which are described in detail in PCT Application PCT/US90/01811.

As used herein, the term "diguanylate cyclase" refers to one or more polypeptides having diguanylate cyclase activity. Diguanylate cyclase activity refers to the property of enzymatically converting two molecules of GTP (guanosine triphosphate) to bis-(3' 5')—cyclic diguanylic acid. At least 3 diguanylate cyclase enzymes have been identified in Acetobacter, DGC1 (SEQ ID NO: 6), as encoded by the dgc1 (SEQ ID NO: 1, nucleotides 3184–4923) gene in the cdg1 (SEQ ID NO: 1) operon and the DGC2 (SEQ ID NO: 9), as encoded by the dgc2 (SEQ ID NO: 2, nucleotides 2465–4186) gene in the cdg2 (SEQ ID NO: 2) operon and DGC3 (SEQ ID NO: 11) encoded by dgc3 (SEQ ID NO: 3, nucleotides 2665–4143) in cdg3 (SEQ ID NO: 3) operon. The term "DGC" refers to any enzyme with diguanylate cyclase activity, including DGC1 (SEQ ID NO: 6), DGC2 (SEQ ID NO: 9), and DGC3 (SEQ ID NO: 11).

The term "diguanylate phosphodiesterase" refers to one or more polypeptides having "diguanylate phosphodiesterase activity." "Diguanylate phosphodiesterase activity" refers to the property of enzymatically cleaving a single phosphodiester bond in c-di-GMP to yield the linear dimer pGpG, i.e., the activity of the diguanylate phosphodiesterase A enzyme, as opposed to the enzyme diguantate phosphodiesterase B. At least three diguanylate phosphodiesterases have been identified from Acetobacter, PDEA1 (SEQ ID NO: 5), as encoded by the pdeA1 (SEQ ID NO: 1, nucleotides 856–3150) gene in the cdg1 (SEQ ID NO: 1) operon, PDEA2 (SEQ ID NO: 8) as encoded by the pdeA2 (SEQ ID NO: 2, nucleotides 98–2353) gene in the cdg2 (SEQ ID NO: 2) operon and PDEA3 (SEQ ID NO: 10), as encoded by the pdeA3 (SEQ ID NO: 3) nucleotides 392–2611) gene in the cdg3 (SEQ ID NO: 3) operon. The term "PDE-A" refers to any enzyme with diguanylate phosphodiesterase activity, including PDEA1 (SEQ ID NO: 5) and PDEA2 (SEQ ID NO: 8).

The terms "cyclic diguanylic acid operon", "cdg operon", "cdg", and "cdg operon" mean the same thing, and refer to operons containing genes encoding enzymes with either diguanylate cyclase activity, diguanylate phosphodiesterase activity, or both. A cdg operon may also encode one or more regulatory proteins having the property of modulating the expression of one or more cdg operon proteins. These terms are not limited to any particular Acetobacter strain or species. The operon may also include transcriptional and translational regulatory elements such as promoter sequences, transcriptional terminator sequences, attenuator sequences, operator sequences, and the like. "cdg1", "cdg2" and "cdg3" refer to the Acetobacter cdg operons represented (at least in part) by SEQ ID NO: 1, SEQ ID NO: 2, and SEQ ID NO: 3 respectively.

The term "cdg operon gene" is defined as a nucleic acid sequence encoding a polypeptide product and encoded by a cdg operon.

The term "cdg operon protein (or polypeptide)" refers to any polypeptide encoded by a cdg operon gene. In addition to referring to polypeptides encoded by cdg operon genes, the term "cdg operon protein", which includes PDE-A1, PDE-A2, PDE-A3, DGC1, DGC2, DGC3, CDG1A, and CDG1D, refers to various derivatives of the polypeptides encoded by naturally occurring cdg operon sequences.

"Operably linked" refers to a juxtaposition such that the normal function of the components can be performed. Thus, a coding sequence "operably linked" to control sequences refers to a configuration wherein the coding sequences can be expressed under the control of these sequences. Such control may be direct, that is, a single gene associated with a single promoter, or indirect, as in the case where a polycistronic transcript is expressed from a single promoter.

"Control sequence" refers to a DNA sequence or sequences necessary for the expression or regulation (transcriptional or translational) of an operably linked coding sequence in a particular host organism. The control sequences which are suitable for procaryotes, for example, include a promoter, optionally an operator sequence, a ribosome binding site, a transcription terminator, and possibly other as yet poorly understood sequences. Eucaryotic cells are known to utilize promoters, polyadenylation signals, enhancers, silencers, and the like.

By "elevated levels" of expression of a molecule of interest, it is intended that a cell expressing "elevated levels" of that molecule contains more molecules for each cell under a given set of growth conditions than a similar cell not producing "elevated levels" of the molecule of interest.

By "reduced levels" of expression of a molecule of interest, it is intended that a cell expressing "reduced levels" of that molecule contains less molecules for each cell under a given set of growth conditions than a similar cell not producing "reduced levels" of the molecule of interest.

"Cells" or "recombinant host cells" or "host cells" are often used interchangeably, and all such designation include progeny. Thus "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell are included. Where distinct designations are intended, it will be clear from the context.

When a specific polypeptide sequence is referred to, the amino acid sequence of the protein referred to includes amino acid sequences derived from the naturally occurring sequence. A polypeptide "derived from" a designated sequence refers to a polypeptide having an amino acid sequence identical to, or in substantial correspondence with a polypeptide encoded in the sequence, or a portion thereof wherein the portion consists of at least 5–10 amino acids, and more preferably at least 10–15 amino acids, which is immunologically identifiable with a polypeptide encoded in the sequence, or exhibits similar biological activity as that of the reference protein in the in vitro or in vivo assays described herein.

As used herein with reference to an amino acid sequence "substantial correspondence" refers to a sequence usually differing by fewer than 10 amino acids, more usually differing by fewer than 5 amino acids. The recombinant protein, displays substantially the same biological properties as the naturally occurring protein. The biological properties may include immunological properties, where antibodies raised to the authentic protein cross-react with the recombinant protein.

When a specific nucleotide sequence is referred to, the nucleotide sequence referred to includes nucleotide sequences derived from the naturally occurring sequence. A polynucleotide "derived from" a designated sequence, for example, the DNA from the pdeA1 (SEQ ID NO: 1, nucleotides 846–3150), refers to a polynucleotide sequence which is comprised of a sequence of at least 6–20 nucleotides, more preferably at least 15 to 20 nucleotides corresponding, i.e., identical to or complementary to, a region of the designated nucleotide sequence. The correspondence to the nucleic acid sequence will be approximately 70% or greater, will preferably be at least 80%, and even more preferably will be at least 90%.

The correspondence or non-correspondence of the derived sequence to other sequences can be determined by hybridization under the appropriate stringency conditions, using standard DNA hybridization technologies in liquid phases or on solid supports. Hybridization techniques for determining the complementarity of nucleic acid sequences are known in the art (see, for example, Sambrook, et al. (1989) Molecular Cloning: A Laboratory Manual, Second Edition, Cold Spring Harbor Press, Cold Spring Harbor, N.Y.). In addition, mismatches of duplex polynucleotides formed by hybridization can be determined by known techniques, including digestion with a nuclease such as S1, that specifically digests single-stranded sequences in duplex polynucleotides.

The derived polynucleotide is not necessarily physically derived from the nucleotide sequence shown, but may be generated in any manner, including, for example, chemical synthesis, DNA replication or reverse transcription, which methods are based on the information provided by the sequence of bases in the region(s) from which the polynucleotide is derived.

The term "recombinant polypeptide" as used herein to characterize a cdg operon polypeptide intends a polypeptide encoded by genomic, cDNA, semisynthetic, or synthetic nucleic acid sequences which, by virtue of their origin or manipulation: (1) are not associated with all or a portion of the polynucleotide with which they are associated in nature or in the form of a library; and/or (2) are linked to a polynucleotide sequence other than that to which it is linked in nature.

"Expression system" refers to DNA sequences containing a desired coding sequence and control sequences in operable linkage, so that host cells transformed with these sequences are capable of producing the encoded proteins. In order to effect transformation, the expression system may be included on a vector; however, the relevant DNA may also be integrated into the host chromosome.

The term "heterologous" when used in reference to polynucleotide sequences, refers to polynucleotide sequences not naturally present in a cell or present at a particular genome location. Thus the term heterologous includes, for example, the promoter of gene A operably joined to structural gene B, when A and B genes are from the same organism, as well as the case in which a polynucleotide sequence of one species is transferred to a cell of a different species (or strain).

As used herein, the term "vector" refers to a polynucleotide sequence suitable for transferring nucleic acid sequences into a host cell. The term may include plasmids, mini-chromosomes, phage, naked DNA and the like.

The term "genetic manipulation" intends the purposeful alteration of polynucleotide sequences either by in vitro techniques, in vivo techniques, or a combination of both in vitro and in vivo techniques. "Genetic manipulation" includes the introduction of heterologous polynucleotide sequences into cells either into the chromosome or as an extrachromosomally replicating elements, the alteration of chromosomal polynucleotide sequences, the addition and/or replacement of transcriptional and/or translational regulatory signals to chromosomal or plasmid encoded genes, and the introduction of various insertion, deletion and replacement mutations in genes of interest. Methods for in vitro and in vivo genetic manipulations are widely known to those skilled in the art and can be found, for example, in Sambrook, et al., Molecular Cloning: A Laboratory Manual, 2nd Ed., Cold Spring Harbor Press (1989), Goeddel, Method in Enzymology, Vol. 185, Academic Press (1990). Specific techniques for the genetic manipulation of Acetobacter species can be found in U.S. patent applications Ser. No. 07/689,008 which are herein incorporated by reference.

The term "recombinant" when used to refer to cells, intends cells that have been genetically manipulated, or are the progeny of cell that have been genetically manipulated.

The composition of all bacterial growth media used in this application can be found in U.S. patent application Ser. No. 07/689,008 filed Apr. 22, 1991.

B. Specific Embodiments

This section provides the nucleotide sequences of the cdg1 (SEQ ID NO: 1), cdg2 (SEQ ID NO: 2) and cdg3 (SEQ ID NO: 3) operons, the amino acid sequences of cdg operon encoded proteins, purified preparations of cdg operon proteins, and cells possessing the ability to produce either elevated or diminished levels of one or more cdg operon proteins.

(i) General Description

The subject invention, among other things, provides the nucleotide sequence of portions of at least 3 c-di-GMP operons isolated from Acetobacter. The first of the operons, cd1 (SEQ ID No: 1), comprises at least 4 genes. In order of transcription these genes are: (1) cdg1A (SEQ ID NO: 1, nucleotides 206–829), a gene of unknown function; (2) pdeA1 (SEQ ID NO: 1, nucleotides 846–3150), a diguanylate phosphodiesterase; (3) dgc1 (SEQ ID NO: 1, nucleotides 3184–4923), a diguanylate cyclase, (4) cdg1D (SEQ ID NO: 1) nucleotides 4933–5346), a gene of unknown function.

The second of the three isolated operons, cdg2 (SEQ ID No.: 2) has at least 2 genes, in order of transcription, these genes are: (1) pdeA2 (SEQ ID NO: 2, nucleotides 98–2353), a diguanylate phosphodiesterase; and (2) dgc2 (SEQ ID NO: 2, nucleotides 2465–4186), a diguanylate cyclase.

The third of the three isolated cdg operons, cdg3 (SEQ ID NO: 3) has at least 2 genes: (1) pdeA3 (SEQ ID NO: 3, nucleotides 392–2611), a diguanylate phosphodiesterase, and (2) dgc3 (SEQ ID NO: 3, nucleotides 2665–4143), a diguanylate cyclase.

The cdg1 (SEQ ID NO: 1) operon may contain more than 4 genes, cdg2 (SEQ ID NO: 2) operon may contain more than 2 genes, and the cgd3 (SEQ ID NO: 3) operon may contain more than 2 genes. The presence of these other genes may be readily detected by standard recombinant DNA library screening techniques such as nucleic acid hybridization screening of genomic libraries with hybridization probes derived from the 5' or 3' terminal regions of the cdg1 (SEQ ID NO: 1), cdg2 (SEQ ID NO: 2), or cdg3 (SEQ ID NO: 3) operon sequences. Additional cdg operon sequences discovered by the library screening may then be subjected to DNA sequencing in order to detect open reading frames, and thus the amino acid sequence of these other cdg operon encoded polypeptides.

An important aspect of the subject invention is the discovery that Acetobacter strains may contain more than one cdg operon. Without the knowledge of the existence of multiple cdg operons, a successful strategy for the inactivation of cdg encoded genes might not be achieved because of residual expression of non-inactivated genes.

The cdg operon genes are highly homologous to one another at both the amino acid and the nucleotide level, as can be seen in FIGS. 1–5. Homology scores are calculated based on the method of Genalign multiple Sequences Alignment Program from Intellegenetics.

It will be appreciated by those skilled in the art that homologous regions between proteins may be evolutionarily conserved, and it is unlikely that substantial amino acid sequence changes, can be made in the conserved regions without altering the enzymatic properties of the protein. Thus by considering regions of homology between different cdg operon polypeptides and nucleic acid sequences, guidance is provided to one seeking to modify the amino acid sequence of a cdg operon protein without substantial loss of the biological activity of the protein.

Although the function of the proteins encoded by cdg1A (SEQ ID NO: 1, nucleotides 206–829) and by cdg1D (SEQ ID NO: 1. nucleotides 4933–5346) have not been identified, comparison of the amino acid sequence of CDG1A (SEQ ID NO: 4) and CDG1D (SEQ ID NO: 7) with protein data bases reveal homology with known proteins. CDG1A (SEQ ID NO: 4) bears 29% amino acid identity and 53% similarily with the protein encoded by fixK of *Rhizobium melliloti*, a nitrogen fixation operon regulatory gene. CDG1D (SEQ ID NO: 7) bears 38% amino acid identity and 59% similarity over 100 amino acid residues, with the protein encoded by purA of *E. coli*, an adenylosuccinate synthetase, which converts IMP to adenylosuccinate (later converted to ATP).

It will be appreciated by those skilled in the art that as a result of the degeneracy of the genetic code, a multitude of nucleotide sequences, some bearing minimal nucleotide sequence homology to the nucleotide sequence cdg1 (SEQ ID NO: 1) and cdg2 (SEQ ID NO: 2) may be produced. The invention has specifically contemplated each and every possible variation of peptide or nucleotide sequence that could be made by selecting combinations based on the possible amino acid and codon choices made in accordance with the standard triplet genetic code as applied to the sequences of Sequences ID Number 1–3, and all such variations are to be considered as being specifically disclosed.

(ii) Construction of Strains Expressing Altered Levels of c-di-GMP Metabolic Enzymes By providing the nucleotide sequence of cdg operons cdg1 (SEQ ID NO: 1) and cdg2 (SEQ ID NO: 2), the subject invention provides for cells genetically manipulated so as to be altered with respect to the ability to produce levels of cdg operon polypeptides under specific growth conditions. The genetic manipulations of interest involve alterations of cdg operon nucleotide sequences or sequences adjacent to cdg operon sequences. These alterations include the ability to express one or more cdg operon protein at elevated levels compared to the levels prior to genetic manipulation, the expression of one or more cdg operon gene proteins at reduced levels, and the altered regulation of expression of one or more cdg operon proteins. Genetically manipulated cells may also be produced in which expression of several cdg operon encoded polypeptides is altered so as to achieve different levels of expression relative to the wild type level, e.g., the expression of one cdg operon encoded protein may be increased and the expression of a second cdg operon encoded protein may be reduced.

Cells for genetic manipulation of the cdg operon may be prokaryotic or eukaryotic, prokaryotic cells being preferred. Procaryotic cells for genetic manipulation include bacterial species naturally containing cdg operons and strains of species not naturally encoding cdg operons. Particularly preferred species for genetic manipulation are cellulose producing bacterial species, especially Acetobacter species. It is also of interest to genetically manipulate cdg operons in cells not naturally producing cellulose synthase, but genetically manipulated to do so.

Recombinant DNA methodology may be employed to create bacterial strains producing reduced quantities, including the complete absence, of cdg operon proteins, reduced levels of PDE-A being of particular interest. The creation of these strains producing reduced levels of cdg operon derived proteins may be achieved by the introduction of "inactivating genetic constructs" into bacterial strains for genetic manipulation. When introduced into cells for genetic manipulation, inactivating constructs preferably recombine by a homologous recombination mechanism into various sites within cdg operons, or adjacent polynucleotide sequences, so as to reduce the expression of one or more cdg operon polypeptides. Inactivating constructs may contain a region of nucleotide sequence substantially homologous to a portion of a cdg operon. By "substantially homologous" it is intended that there be sufficient homology between the two sequences to permit the cell's endogenous homologous recombination mechanisms to function. The region of the genetic construct substantially homologous to a portion of a cdg operon preferably contains a disruption of the homologous region. By disruption, it is intended a mutation that if present in a chromosomal copy of a cdg operon would reduce the expression of one or more cdg operon proteins. These mutations include insertions, deletions, and replacements (preferably nonsense codon generating replacements) of one or more nucleotides. Preferred mutations are insertions within a coding region of the cdg operon region of the inactivating vectors. More preferably, these insertion nucleotide sequences encode a genetic marker selectable in the organism of interest, thereby providing for the monitoring of the cdg operon disruption process.

Inactivating genetic constructs may or may not contain a vector sequence, i.e., a nucleotide sequence capable of independent replication. Inactivating genetic constructs are preferably incapable of replication in the organism to be modified. Thus introduction of an inactivating genetic construct into an organism for modification will necessarily results in recombination into the chromosome or loss in subsequent cell divisions.

Inactivating constructs may contain a replicon functional in at least one organism but incapable of replication in the organism which is to be genetically modified. Inactivating constructs containing a replicon preferably contain a mobilization sequence permitting the transfer of the inactivating construct from a species in which the replicon is functional to species in which the replicon is not functional by the process of conjugation. Alternatively, inactivating constructs not containing replicons may be introduced into cells for genetic manipulation by the process of transformation.

When inactivating a single gene within a cdg operon, preferred inactivating genetic constructs may contain nucleotide sequence alterations that do not disrupt the reading frame of the cdg operon protein gene in which the mutation is made, thereby minimizing polar effects on the transcription of other cdg operon genes.

Other means of decreasing the expression of cdg operon encoded genes include the production of anti-sense RNA complementary to a portion of the cdg operon. The antisense RNA may be expressed from a plasmid vector or from a vector inserted into the chromosome of the cells of interest.

When creating cells lacking the ability to express a cdg operon gene, inactivation of all expressed copies of the gene present in the cell is necessary, otherwise residual expression from other copies of the cdg operon gene may occur. In Acetobacter species, particularly Acetobacter 1306-21, each cdg operon may contain a pdeA and a dgc gene. When more than one cdg operon is present in a cell, the different operons may be transcribed at different rates, thus significant decrease in cdg operon gene expression may be achieved by inactivating fewer than all of the cdg operons in a cell. When inactivating more than one cdg operon by means of more than one inactivating genetic constructions, it is preferable that the different inactivating genetic constructions contain different selectable markers.

In addition to using inactivating genetic constructs to reduce or eliminate the expression of cdg operon genes, the subject invention also provides for the reduction or elimination of cdg operon gene expression by means of anti-sense RNA. Various cdg operons, or portions thereof, preferably portion that are conserved between isozymes of different cdg operons from the same organism, may be functionally joined to promoter sequences in reverse-orientation so as to provide for anti-sense transcripts. Anti-sense RNA is particularly useful for reducing the expression of genes transcribed from multiple operons. The promoter (and associated regulatory sequences) initiating the transcription of anti-sense RNA may be constitutive or inducible. The anti-sense RNA producing "gene" may be located on the chromosome of the organism of interest or may be located extra-chromasomally, e.g., plasmid-borne.

The subject invention also provides for cells that produce elevated levels of one or more cdg operon encoded proteins, elevated levels of DGC being especially of interest. Increased levels of expression may be achieved by a variety of genetic manipulations, including placing cdg operons, or portions and thereof, on multi-copy plasmids (or other similar vectors), and operably joining high level heterologous promoter sequences to cdg sequences (either on plasmids or on the chromosome). High level heterologous promoters may be operably linked to cdg sequences for expression by in vitro manipulations and introduced into cells of interest. When introduced into cells of interest the cdg sequences joined to the heterologous promoter sequences may recombine into the chromosome so as to replace a region of chromosome containing the promoter sequence naturally joined to a cdg operon.

In addition to operably linking high level promoters to cdg operon encoded genes, other transcriptional control sequences (promoters, operators, attenuators and the like) may be operably linked to cdg operon genes so as to provide for inducible or constitutive expression of cdg operon encoded gene or genes. Thus the regulation of cdg operon genes may be altered so as to provide for expression during specific growth phases and under the desired media conditions. Genetic techniques for joining transcriptional control sequences to cdg operon sequences are essentially the same as the previously discussed techniques for joining heterologous high level promoters to cdg operon sequences.

The previously discussed techniques for modifying the expression of cdg operon genes are not limited to genes encoding enzymes, but also include the modification of expression of cdg operon encoded regulatory genes. It will be appreciated that increases in the expression of cdg operon genes may be increased by increasing the expression of a transcriptional activator or decreasing the expression of a transcriptional repressor; the converse being true for decreasing the expression of cdg operon genes.

Other means for modulating the expression levels of cdg operons include the titration of cdg operon regulatory polypeptides having the ability to bind to specific nucleotide sequences within cdg operons. Titration at these regulatory proteins may be achieved by placing cdg operon nucleotide sequences that bind regulatory proteins on multicopy number plasmid capable of replicating in suitable cells. For example, the expression of a cdg operon gene may be decreased if a polypeptide exists that stimulates transcription of a cdg operon and the nucleotide sequence that polypeptide binds to is placed on a high-copy number plasmid. Nucleotide sequences capable of binding cdg operon regulatory proteins may be readily determined by performing sequential deletion analysis of nucleotide sequences known to modify the expression of cdg operon genes.

The subject invention provides for conferring the ability to produce c-di-GMP a desired levels on a variety of cells by transferring genetic constructions comprising cdg operons or portions thereof, especially dgc genes, into cells of interest. These genetic constructions may be capable of expressing DGC, or both DGC and PDEA. Cells of interest for synthesizing c-di-GMP may be eukaryotic or prokaryotic, prokaryotic cells being preferred. Of particular interest is the introduction of these genetic constructions into cells possessing the ability to produce a cellulose synthase having an activity that is capable of being modulated interaction with c-di-GMP preferably cellulose synthase from Acetobacter species, more preferably from Acetobacter 1306-21. Cells of interest may naturally produce cellulose synthase or be genetically modified to do so. Furthermore, it is of interest to in details on how to transfer the ability to produce cellulose synthase to cells not naturally producing cellulose synthase, e.g., E. coli can be found in co-pending U.S. patent application Ser. No. 07/689,008, filed Apr. 22, 1991 which is herein incorporated by reference. Since c-di-GMP may increase the activity of cellulose synthase, it may be of interest to confer the ability to produce c-di-GMP on cells producing cellulose synthase.

(iii) Isolation of cdg Operon Sequences

The polynucleotide sequences encoding cdg operons were obtained from an Acetobacter 1306-3 and Acetobacter 1306-21 genomic DNA library, as set forth in the examples.

Oligonucleotide probes pools were produced based on information obtained by Edman degradation amino acid sequencing of purified Acetobacter DGC and PDEA enzymes. The oligonucleotide pools were used as primers for PCR reactions amplifying Acetobacter chromosomal DNA; the amplified region of the chromosomal DNA was used as a hybridization probe to screen the library. Alternatively, hybridization probes were produced solely from amino acid sequence information obtained from purified proteins without reliance on a PCR amplification step. Library isolates were confirmed by comparison with deduced amino acid sequences obtained from DNA sequencing the clones against the amino acid sequence obtained from amino acid sequencing the isolated proteins. The DNA sequences isolated from the library were used to construct strains of Acetobacter in which production of protein encoded by the cloned gene was abolished. Analysis of the enzymatic activity of these genetically manipulated strains revealed the presence of multiple PDEA and DGC encoding genes. SDS-PAGE analysis and western blots of extract made from Acetobacter strains genetically manipulated so as to not produce specific cdg operon polypeptides were used to confirm the identity of the cloned genes.

The nucleotide sequences of operon cdg1, (SEQ ID No: 1), cdg2 (SEQ ID No: 2), and cdg3 (SEQ ID No: 3) or portions thereof may be used as hybridization probes for the isolation of homologous genes from genetic libraries produced from the genomes of a variety of species, including those species other than those from which cdg1 and cdg2 were isolated. Species of particular interest include species producing bacterial cellulose synthase, these species include species from the genera Acetobacter, Agrobacteria, Sarcinae, and Rhizobia. Techniques for the screening of genetic libraries are well known and can be found for example in *Molecular Cloning: A Laboratory Manual* 2nd Ed., Sambrook, et al., Cold Spring Harbor Press (1989).

Suitable nucleic acid hybridization probes for the detection of cdg operon gene homologous sequences comprise at least 14, preferably 25, and more preferably at least 500 nucleic acid base pairs from the sequence of cdg1 (SEQ ID NO: 1), cdg2 (SEQ ID NO: 2), or cdg3 (SEQ ID NO: 3). Hybridization probes may be labeled by a variety of labels including radionuclides, such as $^{32}p$ or $^{35}S$, or enzymatic labels such as alkaline phosphatase coupled to the probe via avidin/biotin coupling systems and the like.

Probes for hybridization may be synthesized by both enzymatic, and in vitro techniques. Short hybridization probes are preferably synthesized by in vitro methodology such as the use of commercially available DNA synthesizers such as Applied Biosystems™ machines. An additional use for nucleic acid hybridization probes involves their use as primers for the polymerase chain reaction (PCR). The polymerase chain reaction is described in detail in U.S. Pat. Nos 4,965,188 and 4,683,202 and 4,800,195.

(iv) Production of cdg Operon Proteins

The nucleotide sequences of the cdg operons being provided for, as well as the amino acid sequences of the polypeptides encoded by cdg operons, the present invention enables the production of purified cdg operon encoded proteins by recombinant DNA expression techniques and by both in vitro polypeptide synthesis techniques and by in vivo production.

Automated equipment for the direct synthesis of polypeptides disclosed herein is commercially available. Such equipment provides convenient access to peptides of the invention, either by direct synthesis or by synthesis of a series of fragments that can be coupled using other known techniques.

Other methods for synthesis of cdg operon proteins include the in vitro transcription of cdg operon gene sequences coupled with the in vitro translation of the RNA transcripts thus produced. In vitro transcription systems are well known in the art. In vitro transcription systems typically involve the creation of nucleotide sequences in which the coding sequence of interest is located downstream from a strong promoter, such as promoters specific for SP-6 or T7 RNA polymerases, followed by the addition of an RNA polymerase specific for the promoter, and substrates required for the reaction. Similarly, in vitro translation systems are well known in the art and may be used to produce cdg operon protein from a variety of transcripts produced by in vitro transcription systems.

Expression vectors may be used to express quantities of cdg operon proteins in a variety of cell hosts. Detailed descriptions of many expression vectors and their use can be found, for example in Goeddel, *Methods in Enzymology*, Vol. 185 (1990) Academic Press. Expression vectors contain promoters functional in the host of interest. The promoter may be operably linked to the coding sequence of a gene of interest so as to produce a translatable mRNA transcript encoding a cdg operon protein. Expression vectors will generally have convenient restriction sites located near the promoter sequence so as to provide for the insertion of coding nucleic acid sequences. The promoters in suitable expression vectors in particular expression vectors for use in eukaryotic cells, may be either constitutive or inducible. In addition to having promoter sequences, expression vectors may contain various enhancer sequences and the like, included for the purpose of maximizing expression of cdg operon proteins.

The invention having been described, the following examples are offered to illustrate the subject invention by way of illustration, not by way of limitation.

EXAMPLES

I. Purification of Diguanylate Cyclase

The enzyme was purified from Acetobacter 1499 essentially as described by Ross, et al. (*Nature* 325:279–281 (1987)). The GTP affinity column purification scheme used resulted in the isolation of 4 polypeptides bands that could be visualized by PAGE: band Ia, having an apparent molecular weight of about 80 kDa, band Ib, having an apparent molecular weight of 78 kDa, band III, having an apparent molecular weight of 65 kdal, and band IV, having an apparent molecular weight of 59 kDa. Bands Ia and Ib were found to be produced by proteins having diguanylate phosphodiesterase activity. Bands III and IV were found to be produced by proteins having diguanylate cyclase activity.

II. $NH_3$ - terminus amino acid sequence of diguanylate cyclase

Peptides were analyzed by automated Edman degradation on an Applied BioSystems, Inc. Model 470A Sequenator. Analysis of band III, i.e., the 65 kdal polypeptide band, gave no sequence, indicating that the N-terminal residue was blocked. Treatment of the peptide sample with trifluoracetic acid in order to deblock an acetylation or hydrolyze the formyl group on a terminal N-formyl methionine failed to render the sample capable of being sequenced directly.

The band III peptide was then subjected to partial digestion by oxidation with performic acid (Hirst *J. Biol. Chem.* 19:611 (1956) and Moore *J. Biol. Chem.* 238:235 (1963). The preparation was then dialyzed against 0.1% TFA/25% $CH_3CN/H_2O$ and dried. The preparation was then incubated 4 hours at 40° C. in 100 µl 6M guanidine chloride, 98 µl 0.05M Tris pH 9.1, 2 µl lysyl endopeptidase from Achromobacter (200 µg/400 µl in 0.022 mM Tris pH8.1). The peptides from the digestion were subsequently separated by HPLC on a C4 reverse-phase column D-1 elution with a gradient of 0 to 70% solvent B, where solvent A is 0.1% TFA in $H_2O$ and B is 0.085% TFA/85% $CH_3CN/H_2O$. The peptides in 5 column fractions were sequenced. The sequence of fraction 50 was particularly useful.

TABLE 1

(SEQ ID NO: 12)
Sequence of a Diguanylate Cyclase Peptide
HPLC Fraction 50; SEQ 904

| 1 | 2 | 3 | 4 | 5 | 6 | 7 | 8 | 9 | 10 | 11 | 12 |
|---|---|---|---|---|---|---|---|---|----|----|----|
| * | LEU | SER | GLU | LEU | ALA | GLU | THR | ASP | THR | LEU |    |
| 13 | 14 | 15 | 16 | 17 | 18 | 19 | 20 | 21 | 22 | 23 | 24 |
| THR | ALA | LEU | LEU | ASN | ARG | GLY | GLY | PHE | ASN | THR | ALA |
| 25 | 26 | 27 | 28 | 29 | 30 | 31 | 32 | 33 | 34 |    |    |
| LEU | SER | ALA | ALA | LEU | GLY | * | * | * | LYS |    |    |

* indicates that amino acid residue was not identified

III. PCR Generation of Oligonucleotide Probes For Cloning of Diguanylate Cyclase On the basis of the amino acid sequence information obtained from fraction 50 (Run 904), pools of oligonucleotides corresponding to amino acids 7 to 11 (ALA GLU THR ASP THR) and amino acids 19 to 24 (GLY PHE ASN THR ALA). The oligonucleotide pools are given in Table 2.

TABLE 2

3' region

| 19 | 20 | 21 | 22 | 23 | 24 |
|----|----|----|----|----|----|
| GLY | GLY | PHE | ASN | THR | ALA |
| GGT | GGT | TTT | AAT | ACT | GC |
| C | C | C | C | C |   |
| A | A |   |   | A |   |
| G | G |   |   | G |   |

Oligonucleotide Probes

```
Cel-5  (SEQ ID NO: 15)  GGA GGA TTT AAT ACA GC
                         C   C   C   C   C
Cel-6  (SEQ ID NO: 16)  GGT GGA TTT AAT ACA GC
                         G   C   C   C   C
Cel-7  (SEQ ID NO: 17)  GGA GGT TTT AAT ACT GC
                         C   G   C   C   G
Cel-8  (SEQ ID NO: 18)  GGA GGA TTT AAT ACT GC
                         C   C   C   C   G
Cel-9  (SEQ ID NO: 19)  GGT GGT TTT AAT ACA GC
                         G   G   C   C   C
Cel-10 (SEQ ID NO: 20)  GGT GGA TTT AAT ACT GC
                         G   C   C   C   G
Cel-11 (SEQ ID NO: 21)  GGA GGT TTT AAT ACT GC
                         C   G   C   G   G
Cel-12 (SEQ ID NO: 22)  GGT GGT TTT AAT ACT GC
                         C   G   C   G   G
(SEQ ID NO: 13)
```

5' region

```
 7   8   9   10  11
ALA GLU THR ASP THR  (SEQ ID NO: 23)

GCT GAA ACT GAT AC   (SEQ ID NO: 24)
 C   G   C   C
 A       A
 G       G (SEQ. ID NO: 14)
```

TABLE 2-continued

Oligonucleotide Probes

```
Cel-1 (SEQ ID NO: 25)  GCT GAA ACT GAT AC
                        C   G       C
                        A
                        G
Cel-2 (SEQ ID NO: 26)  GCT GAA ACC GAT AC
                        C   G       C
                        A
                        G
Cel-3 (SEQ ID NO: 27)  GCT GAA ACC GAT AC
                        C   G       C
                        A
                        G
Cel-4 (SEQ ID NO: 26)  GCT GAA ACG GAT AC
                        C   G       C
                        A
                        G
```

Various combinations of the oligonucleotide pools were used as PCR primers in a PCR amplification of Acetobacter 1306-3 DNA. As the distance between amino acids 7 and 24 is 53 nucleotides, pools containing specifically binding nucleotide primers would be expected to produce a 53 base pair DNA product upon amplification by PCR. The 53 bp amplified sequence would be expected to be an exact match for a diguanylate cyclase encoding gene.

PCR amplification was carried out in a volume of 50 µl in 3 mM MgCl$_2$, 10 mM Tris pH8.3, 50 µM KCl, 100 µg 1 ml gelatin, 200 µM each dNTP, 500 µM primer (downstream), 50–500 µM of primer (upstream), 2 units Tag polymerase. Following heat denaturation of the template at 93° C., the reactions were allowed to cool to 35° C. for annealing. The temperature was then raised to 68° C. for 30 seconds for DNA synthesis. The temperature was then raised to 93° C. again for denaturation. The reaction cycle was repeated 15–30 times. Primer pool combinations Cel-2 (SEQ ID NO: 26)+Cel-5 (SEQ ID NO: 15) and Cel-2 (SEQ ID NO: 26)+Cel-8 (SEQ ID NO: 78) produced a 53 bp DNA band as visualized by gel electrophoresis.

IV. Cloning of Diguanylate Cyclase

A gene bank of Acetobacter 1306-11 was constructed in the broad host range, mobilizable cosmid pKT230COS5. The average size of the cosmid insert is about 30 Kb. The gene bank contained about 2000 clones.

Hybridization Conditions for Probing of the Cosmid Bank with 53 bp PCR Product

The cosmid bank was probed as follows:

Nitrocellulose filters containing plasmid DNA from approximately 2000 clones were first pre-hybridized at 42°

C. for 1½ hours in a solution containing 6×SSC, 5×Denhardt solution, 50 mM NaPO₄ pH 6.5, 40% formamide and 100 ug/ml sheared salmon sperm DNA. This solution was replaced with a similar hybridization solution that contained only 20 ug/ml of sheared salmon sperm DNA. The 53 bp probe was end labeled with gamma $^{32}$P ATP to $2.16 \times 10^6$ cpm/pmole and $4.17 \times 10^7$ cpm of the boiled probe were added to 50 mls of hybridization solution. The filters were incubated at 60° C. for 3 hr. The filters were then washed once with 5×SSC+0.1% SDS solution at room temperature for 5 min., once with 2×SSC+0.1% SDS at 60° C. for 10 min., and twice with 1×SSC+0.1% SDS at 60° C. for 10 and 30 min. respectively. The filters were exposed to Kodak® XAR film for 1 hr. and positive clones were scored. The cosmid clones were streaked on R2-4 plates containing Str at 50 μg/ml. Three unique cosmid classes were identified and are represented by the cosmids 6C5, 3F3, and 15A8. 6C5 contains the cdg2 (SEQ ID NO: 2) operon, 3F3 contains the cdg1 (SEQ ID NO: 1) operon, and 15A8 contains cdg3 operon.

Clones 3F3 and overlapping 12A7 were studied for further analysis. Restriction analysis of 3F3 and 12A7 revealed that the inserts overlapped; both clones contained a 1.7 Kb and 1.6 Kb PstI fragment that hybridized to Cel-21. Also isolated were clones 15A8 and 6C5. 15A8 contains a 2.3 kd Pst I fragment that hybridizes to Cel-21. Clone 6C5 contains a single 2.6 Kb Pst I band that hybridizes to Cel-21.

PCR amplification of the various clones with the primers Cel-14 and Cel-8 (SEQ ID NO: 18), or Cel-2 (SEQ ID NO: 26) and Cel-8 (SEQ ID NO: 18), revealed a 53 bp product only with clone 6C5, indicating that clone 6C5 contained a diguanylate cyclase gene subsequently identified as the dgc2 (SEQ ID NO: 2, nucleotides 2465–4186) gene. Subsequently the clone was found to contain only part of the dgc2 (SEQ ID NO: 2, nucleotides 2465–4186) gene.

Cloning of Diguanylate Cyclase Gene

In order to clone the complete dgc2 (SEQ ID NO: 2, nucleotides 2465–4186) gene and other dgc genes, a second gene bank, prepared from Acetobacter 1306-3 was screened. The gene bank was prepared and screened essentially as described for the isolation of clones 6C5, 3F3, and 15A8. Cel-18 was used as a hybridization probe. Six clones, 5C10, 13O1, 13G6, 22D6, 16G3 and 21B4 were isolated. Pst I and Hinc II restriction digests indicated that T16G3 and T21B4 are similar to each other, the remaining four clones are also similar to each other, but not to the other two clones.

PCR amplification was used to confirm the presence of the diguanylate cyclase gene. PCR was performed using Cel-15 as the 5' primer and Cel-8 (SEQ ID NO: 18) as the 3' primer under conditions as described in section III. 5C10 and 13D1 contained an intact diguanylate cyclase gene.

V. Cloning of Diguanylate Phosphodiesterase Genes

N-terminal Amino Acid Sequence of Diguanylate Phosphodiesterase A

Acetobacter 1306-21 was used for the purification. Growth conditions and medium are as described in Section XII for "seed cultures".

About 9 gms of cells (dry weight) were centrifuged and washed twice with TME (50 m Tris pH 7.5, 10 mM MgCl₂, 1 mM EDTA), then the cells were suspended in the same buffer plus 20% polyethylene glycol and broken in a french press. The disrupted cells were centrifuged and the supernatant of the second wash was loaded onto a 2 ml GTP-agarose column. The supernatant of the first wash was discarded due to the presence of significant amounts of band Ib protein. The column was washed with 50 ml TME and 30ml 1 mM ATP, 20 ml 1 mM CTP, and 20 ml 1 mM 5' GMP, each in TME, followed by 30 ml TME. Diguanylate cyclase was eluted with 50 mM Tris, pH 7.5, 10 mM MgCl₂, 10 mM EDTA, 200 mM KCl. After washing with 9 ml TME, the PDEA was eluted with 15 ml 2 mM GTP in TME. SDS PAGE showed that the majority of the PDEA eluted between 2 to 7 ml. These five ml were pooled and concentrated in an Amicon Centricon 10 concentrator to 0.5 ml. Protein was estimated relative to BSA on SDS PAGE to be roughly 9 μg. This sample was dried to 10 μL in a Speed Vac, subjected to SDS PAGE, and transferred to a PVDF membrane. The top and bottom halves of the PDEA band were cut out and submitted separately for N-terminal amino acid sequencing.

The final purification exploited the observation that PDEA binds more tightly to the cell membranes than do other proteins, allowing a starting preparation containing a smaller amount of contaminating proteins. Additional separation was obtained by eluting the column first with 200 mM KCl, which also removed a significant amount of the Band Ib protein. Furthermore, division of the transferred protein band into halves helped to remove the contribution of the Band Ib protein to the final sequence. Band Ib migrates just below the PDEA on SDS-PAGE and thus could overlap with the bottom of the PDEA band. This overlap could be seen in the presence of a contaminating initial Met in the sequence from the bottom half, which is not present in the top half. Each of the three modifications significantly reduced the recovery of the protein.

An Applied Biosystems, Inc., Model 470A Sequenator was used to determine the NH₃-terminal amino acid sequence of the band Ia protein. The NH₃-terminal sequence was determined to be:

NH₃ --- Pro Asp Ile Thr Ala Leu Thr Thr Glu Ile Leu Leu Pro
Ala Leu Glu Arg Ala - COOH (SEQ ID NO: 52)

Cloning of Phosphodiesterase A

Oligonucleotide hybridization probes were designed based on the first 5 amino terminal amino acids of purified phosphodiesterase. Table 3 is a summary of the oligonucleotide probe pools synthesized.

TABLE 3

| CCS | GAT | ATH | ACN | GC | | | |
|-----|-----|-----|-----|-----|-----|-----|-----|
| W | C | | | | CEL-117 | (SEQ ID NO: 29) | N = G + A + T + C |
| S | C | | | | CEL-118 | (SEQ ID NO: 30) | H = A + T + C |
| W | C | | | | CEL-119 | (SEQ ID NO: 31) | S = G + C |
| C | C | W | S | | CEL-120 | (SEQ ID NO: 32) | Y = C + T |
| W | T | W | W | | CEL-121 | (SEQ ID NO: 33) | W = A + T |
| | | | | | CEL-122 | (SEQ ID NO: 34) | |

TABLE 3-continued

| CCS | GAC | ATH | ACN | GC | CEL-119 | (SEQ ID NO: 31) |
|-----|-----|-----|-----|-----|---------|-----------------|
|     | C   | C   |     |    | CEL-123 | (SEQ ID NO: 35) |
|     | C   | A   |     |    | CEL-124 | (SEQ ID NO: 36) |
|     | C   | T   |     |    | CEL-125 | (SEQ ID NO: 37) |
|     | G   | C   |     |    | CEL-126 | (SEQ ID NO: 38) |
|     | G   | A   |     |    | CEL-127 | (SEQ ID NO: 39) |
|     | G   | T   |     |    | CEL-128 | (SEQ ID NO: 40) |
| CCS | GAC | ATC | ACS | GC | CEL-121 | (SEQ ID NO: 33) |
|     | C   |     | C   |    | CEL-129 | (SEQ ID NO: 41) |
|     | C   |     | G   |    | CEL-130 | (SEQ ID NO: 42) |
|     | G   |     | C   |    | CEL-131 | (SEQ ID NO: 43) |
|     | G   |     | G   |    | CEL-132 | (SEQ ID NO: 44) |
|     | C   |     | A   |    | CEL-133 | (SEQ ID NO: 45) |
|     | C   |     | T   |    | CEL-134 | (SEQ ID NO: 46) |

Oligonucleotide pools Cel-117 (SEQ ID NO: 29) through Cel-120 (SEQ ID NO: 32), each containing 24 sequences, represent all possible codon combinations for the first four amino acids and the first 2 bases of alanine. Oligonucleotide pools Cel-121 (SEQ ID NO: 33) and Cel-122 (SEQ ID NO: 34) were also designed based on the N-terminal amino acid sequence, but the third codon positions were limited to G and C in Cel-121 (SEQ ID NO: 33) and A and T in a Cel-122 (SEQ ID NO: 34).

The pools were kinased with $^{32}$P-ATP to a specific activity of approximately $1 \times 10^7$ cpm/pmole. The kinased probe pools were used to hybridize against dot blots of Acetobacter 1306-3 chromosomal DNA.

The dot blots were prepared by digesting 100 µg of 1306-3 chromosomal DNA with Pst I. The DNA was ethanol precipitated and resuspended in a solution containing 85 µl of 100 mM Tris pH 74, 15 µl of 2N NaOH and 50 ml 2×SSC. The DNA was incubated at 80° C. for 10 minutes, 20 µl of 2M Tris pH 7.4 was added. 10 µl of solution were spotted onto a nitrocellulose filter. 2-fold serial dilution were made and spotted onto the filter; thus, 5.88, 2.9, 1.47 and 0.07 µg of DNA were spotted. Each row of 5 DNA samples was spotted six times. The filter was subsequently baked under a vacuum at 80° C. for 1 hr. The filter was cut into strips, 1 row per strip. Each strip was separately probed with a single oligonucleotide pool. $1 \times 10^6$ counts/ml of hybridization solution was added, hybridization was allowed to proceed overnight at 40° C. The filters were subsequently washed with 50 mls each with 5×SSC+0.1% SDS at room temperature for 10 minutes, 2×SSC+0.1% SDS at 40° C. for 15 minutes, and 1×SSC+0.1% SDS at 40° C. for 15 minutes. Autoradiography revealed that Cel-121 hybridized the most strongly, while Cel-119 (SEQ ID NO: 31) hybridizing somewhat more weakly. Pools Cel-118 (SEQ ID NO: 30) and Cel-120 (SEQ ID NO: 32) hybridized extremely weakly. Based on the hybridization information, subpools Cel-129 (SEQ ID NO: 41) to Cel-134 (SEQ ID NO: 46) were designed based on Cel-121 (SEQ ID NO: 33), and subpools Cel-123 (SEQ ID NO: 35) to Cel-128 (SEQ ID NO: 40) were designed based on Cel-119 (SEQ ID NO: 31). The subpools were used as hybridization probes for dot blots essentially as above. Cel-121 (SEQ ID NO: 33) and Cel-123 (SEQ ID NO: 35) appeared to hybridize the most strongly.

Another gene bank prepared from Acetobacter 1306-3 genome DNA inserted in the vector PUC18-824 described in U.S. patent application Ser. No. 07/689,008, filed Apr. 22, 1991 was probed with a combined probe of labeled Cel-121 (SEQ ID NO: 33) and Cel-123 (SEQ ID NO: 35) in essentially the same way as the hybridization probing for dgc genes was performed. Approximately 5000 E. coli colonies were screened by hybridizing against replica plated nitrocellulose filters using essentially the method of Grunstein and Hogness, Proc. Natl. Acad. Sci. USA, 72:3961 (1975). The filters were probed with $^{32}$p-ATP labeled Cel-121 (SEQ ID NO: 33) and Cel-123 (SEQ ID NO: 35). The probe was labeled by kinasing to a specific activity level of $5 \times 10^6$ cpm/pmole. $1 \times 10^6$ cpm/ml of hybridization solution of each probe was added and hybridization/washing was performed essentially the same as the way in which the dot blot hybridization was performed. Six strongly hybridizing independent clones were isolated. Restriction mapping of the 6 clones revealed that all were siblings. One clone, PDEA-7A was selected for further analysis.

Southern blot analysis revealed that Cel-121 (SEQ ID NO: 33) hybridized to a 0.8 Kb Pst I fragment of PDEA-7A, and no other PstI fragments. The PstI fragment was subsequently subcloned and sequenced.

A PDEA Gene Is Present on Cosmid Clone pKT230cos5-3F3

Nucleotide sequence determination of the pdeA on PDEA-7A revealed that a PDEA encoding gene, i.e., pdeA1 (SEQ ID NO: 1, nucleotides 856–3150), was present on 3F3, a cosmid clone isolated during the cloning of dgc1 (SEQ ID NO: 1) nucleotides 3184–4923).

To determine whether other homologous genes are present in the genome of strain 1306-3, Southern blot analysis was performed on chromosomal DNA isolated from strain 1306-3. 2 µg aliquots of DNA were digested with a variety of restriction enzymes, separated by electrophoresis 1% agarose gel, transferred by electroblotting to a nylon GeneScreen® membrane and probed with a radiolabeled PDEA-7A 3 Kb EcoRI fragment containing the PDEA gene. 200 ng of the DNA fragment were labeled with T4 DNA polymerase using $^{32}$P dCTP as the labelled nucleotide. The probe was then used at $1 \times 10^6$ cpm/ml essentially under GeneScreen® manufacturer conditions, except that 40% formamide was used and the hybridization temperature was 40° C. These conditions allowed for detection of sequences in the genome that are somewhat homologous to pdeA1 (SEQ ID NO: 1) nucleotides 856–3150). The Southern blot results suggest that there are at least 3 and as many as 6 to 7 of homologous sequences in the genome.

VI. Disruption of the pdeA1 gene

The cdg1 (SEQ ID NO: 1) operon is located on cosmid 3F3. The cosmid was mapped by restriction analysis followed by Southern blot analysis. Convenient restriction sites were utilized to disrupt dgc1 (SEQ ID NO: 1, nucleotides 3184–4923) and pdeA1 (SEQ ID NO: 1, nucleotides 856–3150) by insertion inactivation.

The 4.2 Kb EcoRI fragment of 3F3 was subcloned into the EcoRI site of the plasmid pACYC184. Chloramphenicol (Cam) sensitive clones were isolated and DNA was prepared from this clone. This plasmid DNA was partially digested with EcoRV and the linearized DNA was ligated to an EcoRI to AlwNI fragment containing the β-lactamase gene isolated from pBR322 after its sticky ende were repaired by T4 DNA polymerase. Clones resistant to both ampicillin (Amp) and tetracycline (Tet) were identified in which the β-lactamase gene was inserted between the EcoRV sites located at nucleotides 1855 and 1873 (SEQ ID NO:1) causing a gene disruption almost half way from the N-terminus. The resultant plasmid was linearized with BamHI and the DNA was used to transform strains 1306-3 and 1306-21 by electoporation. The resultant transformants were isolated from R20-2+100 µg/ml Amp plates. This transformant was designated 1306-21:Dis1. All 1306-21 transformants were uniformly Cel⁺. Isolates were grown in R20-2+100 µg/ml Amp and their chromosomal DNA was purified. This DNA was digested with PstI or HincII+BglII and the DNA was analyzed by Southern blot. 3 µg of the digested DNA were resolved on an agarose gel, blotted onto Zeta-probe™ filters (BioRad) and probed according to the manufacturer instructions with the 4.0 Kb EcoRI fragment containing the pdeA1 (SEQ ID NO: 1, nucleotides 856–3150) gene. The results suggest that strain 1306-21:Dis1 is disrupted as expected in the pdeA1 (SEQ ID NO: 1, nucleotides 856–3150) gene. In addition to hybridizing to the expected pdeA1 (SEQ ID NO: 1, nucleotides 856–3150) restriction fragments, the pdeA1 (SEQ ID NO: 1, nucleotides 856–3150) probe also hybridized to other phosphodiesterase genes, such as pdeA2 (SEQ ID NO: 1, nucleotides 846–3150).

Cellulose synthase, diguanylate phosphodiesterase A, and diguanylate cyclase assays were performed on the mutants. (See tables 5–9 for results). The results suggest that the disruption of pdeA1 (SEQ ID NO: 1, nucleotides 856–3150) resulted in 80–90% reduction of both phosphodiesterase and diguanylate cyclase activities in these recombinant strains. The results also suggest that disruption of pdeA1 (SEQ ID NO: 1, nucleotides 856–3150) gene has a polar effect on the expression of dgc1 (SEQ ID NO: 1, nucleotides 3184–4923) gene. The cellulose production of these strains was reduced by 30–40%.

In addition to the gene disruption described above in which the pdeA1 (SEQ ID NO: 1, nucleotides 856–3150) gene was disrupted by inserting the amp gene between the EcoRV sites on 3F3, a similar disrupted mutant was constructed by inserting the str gene isolated from the broad host range plasmid pKT230. The fragment containing this antibiotic resistance gene was isolated from the plasmid pNV16 by digestion with HindIII and BamHI. After the fragment ends were repaired with T4 polymerase and dNTPs, the fragment was ligated between the two EcoRV sites located in pdeA1 (SEQ ID NO: 1, nucleotides 856–3150). The disrupted gene was then introduced into strains 1306-21 and 1306-3 by the gene replacement method described above; these transformants were designated 1306-21:ABT3 and 1306-3:ABT3, respectively.

VII. Disruption of the cdg2 operon

The diguanylate cyclase gene, dgc2 (SEQ ID NO: 2, nucleotides 2465–4186), was disrupted by insertion of a beta-lactamase gene into the EcoRV site. An inactivating genetic construction with the disrupted gene was introduced into Acetobacter 1306-21 by electroporation. Southern blot analysis of ampicillin resistant strains confirmed that the endogenous intact dgc2 gene was replaced with the disrupted one. These strains retained a Cel⁺ phenotype on plates. Western-blot analysis showed that these strains lacked Band IV.

An inactivating genetic construction was made by inserting a disrupted diguanylate cyclase gene, dgc2 (SEQ ID NO: 2, nucleotides 2465–4186), in the plasmid pACYC184 as follows. The dgc2 (SEQ ID NO: 2, nucleotides 2465–4186) gene was isolated from the plasmid III531-1 as a HindIII-BamHI fragment and cloned in the EcoRV site of the plasmid pACYC184. The plasmid pACYC184 cannot replicate in Acetobacter and served as a suicide vector. The beta lactamase gene was isolated from the plasmid pBR322 as an EcoRI-AlwNI fragment. This fragment was repaired with Klenow and cloned in the EcoRV site of the dgc2 (SEQ ID NO: 2, nucleotides 2465–4186) gene in the suicide plasmid. The EcoRV site is located near the middle of the coding region of the cyclase gene.

Two plasmids were obtained in which the beta lactamase gene is oriented in either direction with respect to the dc2 (SEQ ID NO: 2, nucleotides 2465–4186) gene, i.e., inactivating genetic constructions. They were designated TRT146-2 and TRT146-4. The beta lactamase gene is in the same transcriptional orientation as the chloramphenicol resistance gene in TRT146-4.

10 micrograms of each plasmid were digested with EcoRI and washed with H₂O in a Centricon spin tube. In addition, 10 micrograms of uncut DNA of each were washed. These DNAs were used to transform about 10¹⁰ cells of 1306-21 by electroporation. The transformation mix was grown in 1 ml of R20-2 at 30° C. for 1 hr. and plated on R20-2 plates containing 50 micrograms of Amp. The plates were incubated at 30° C. for 5 days and scored.

Single colonies from each transformation were picked and streaked on R20-2 plates containing 50 micrograms of ampicillin. The strains containing plasmids TRT146-2 and TRT146-4 were designated 1306-21:TRT150-1 and 1306-21:TRT151-1, respectively.

Chromosomal DNA was prepared from these isolates. Chromosomal DNAs from four transformants and from the wild type strain 1306-21 were digested with HincII or with HindIII+SmaI. Southern blot analysis was performed according to standard procedure. Two identical panels were probed either with a dgc2 (SEQ ID NO: 2, nucleotides 2465–4186) specific probe, CEL30, or a beta-lactamase specific probe, AE108.

All four transformants contained a disrupted gene instead of the intact gene. No gene duplication occurred when the intact plasmid was used, suggesting that the gene replacement must have occurred in two recombinational steps.

VIII. Disruption of dgc1

In order to produce an inactivating genetic constuct for dgc1 (SEQ ID NO: 1, nucleotides 3184–4923), a 3.5 Kb StuI fragment from cosmid 3F3 was cloned into the EcoRV site in the tet resistance gene of pACYC184. Tet sensitive E. coli isolates were screened and a plasmid containing the insert was prepared and was partially digested with NruI (a unique NruI restriction site exists very close to the 5' end of dgc1 (SEQ ID NO: 1, nucleotides 3184–4923)). The linearized full length plasmid DNA was ligated to the blunt-ended fragment containing the beta-lactamase gene of pBR322. Colonies that were resistant to amp and cam (chloramphenicol) were analyzed and two plasmids containing the interrupting amp gene in either orientation in the NruI site in dgc1 (SEQ ID NO: 1, nucleotides 3184–4923) were identified. Each plasmid was linearized by digestion with BamHI and used to transform strains 1306-21 and 1306-3. The phenotype of all transformants was uniformly Cel⁺. Two independent isolates containing the inserted beta-lactamase gene in opposite orientations were grown in R20-2+100 µg/ml Amp. These recombinant strains were grown in 150 ml of R70-2+100 µg/ml ampicillin and chromosomal DNA was prepared. The DNA from these strains was then isolated and digested with PstI or StuI, and run on a gel. These strains were named Dis4 mutants.

To ascertain that the Acetobacter recombinant strains obtained resulted from a gene replacement event in dgc1 (SEQ ID NO: 1, nucleotides 3184–4923) in the cdg2 (SEQ ID NO: 2) operon, a genomic Southern blot analysis was performed. Chromosomal DNA was prepared and analyzed essentially as described above except the probe was hybridized at 55° C. The results show that dgc1 (SEQ ID NO: 1, nucleotides 3184–4923) was disrupted, but not dgc2 (SEQ ID NO: 2, nucleotides 2465–4186).

DNA from the recombinant strain was probed by a dgc2 (SEQ ID NO: 2, nucleotides 2465–4186) specific probe to ascertain that the disrupted copy has not recombined into the highly homologous cdg2 (SEQ ID NO: 2) locus. The dgc2 (SEQ ID NO: 2, nucleotides 2465–4186) probe was isolated from a plasmid pTRT93-3 by preparing a 2090 bp HindIII to HincII fragment containing dgc2 (SEQ ID NO: 2, nucleotides 2465–4186), starting at the ATG, nucleotide 2465 and extending to nucleotide 4555 [SEQ. ID NO:2] which contained an engineered HindIII site in front of the dgc2 (SEQ ID NO: 2, nucleotides 2465–4186) initiation ATG. The probe was labeled with T4 polymerase as described by O'Farrel, P. (1981) Focus 3 (Bethseda Research Laboratories, Md.), and hybridization was at 55° C. Strain Dis4 and the recombinant strain TRT 150-1, that is disrupted in dgc2 (SEQ ID NO: 2, nucleotides 2465–4186) and consequently lacking the 57 Kd DGC2 (SEQ ID NO: 9) peptide as determined by western analysis, were subjected to a genomic Southern blot analysis for comparison purposes. The results suggest that the interrupted dgc1 (SEQ ID NO: 1, nucleotides 3184–4923) copy did not recombine into the dgc2 (SEQ ID NO: 2, nucleotides 2465–4186) locus.

In a separate Southern blot analysis, chromosomal DNA was probed with the same dgc2 (SEQ ID NO: 2, nucleotides 2465–4186) probe under hybridization conditions less stringent than prescribed by Zeta-probe™, i.e., at 50° C. In this genomic Southern analysis the dgc2 (SEQ ID NO: 2, nucleotides 2465–4186) probe not only hybridized to dgc2 (SEQ ID NO: 2, nucleotides 2465–4186) in the cdg2 (SEQ ID NO: 2) operon but also to dgc1 (SEQ ID NO: 1, nucleotides 3184–4923) in the cdg1 (SEQ ID NO: 1) operon. The fragments that the probe hybridized are consistent with the restriction map of the cdg1 (SEQ ID NO: 1) and cdg2 (SEQ ID NO: 2) operons.

IX. Disruption of The cdg2 (SEQ ID NO: 2) Operon and Simultaneous Disruption of Both cdg1 (SEQ ID NO: 1) and cdg2 (SEQ ID NO: 2) Operons To inactivate the cdg 2 (SEQ ID NO: 2) operon, a 1.5 Kb PstI fragment spanning pdeA2 (SEQ ID NO: 2, nucleotides 98–2353) and dgc1 (SEQ ID NO: 1) was deleted from plasmid pRT93-4, which contains the 5.6 Kb HindIII to SmaI fragment from cosmid 6C5. The resulting 4.1 Kb fragment was introduced between the HindIII and EcoRV sites in pACYC184. Tetracycline sensitive clones were identified and DNA was prepared in E. coli. The plasmid DNA was linearized with PstI, the ends were repaired and ligated to the fragment containing the amp resistance gene. Amp resistant clones were isolated and plasmid DNA was prepared, linearized with BamHI and introduced into strains 1306-3 and 1306-21 and also into the same strains containing the str disrupted cdg1 (SEQ ID NO: 1), i.e., ABT3 strain (see Section VI). The transformants were obtained by plating on R20-2+100/µg Amp and 80 µg/ml Str colonies of these double mutants are phenotypically Cel$^±$. The double operon mutant strains containing disruptions in pdeA1 (SEQ ID NO: 1, nucleotides 856–3150), pdeA2 (SEQ ID NO: 2, nucleotides 98–2353), and dgc2 (SEQ ID NO: 2, nucleotides 2465–4186) were designated ABT1 strains. Strains containing only a deletion and gene disruption of cdg2 (SEQ ID NO: 2) are phenotypically Cel$^+$. These strains containing disruptions only in the pdeA2 (SEQ ID NO: 2, nucleotides 98–2353) and dgc2 (SEQ ID NO: 2, nucleotides 2465–4186) genes were called ABT2 strains.

Construction of Double Operon Mutants

The 5.6 Kb SmaI to HindIII fragment from the cosmid 6C5, which contains cdg2 (SEQ ID NO: 2), was purified by gel electrophoresis and ligated to a purified HindIII to EcoRV fragment from plasmid pACYC184. The ligation mixture was used to transform E. coli MM294. The cells were plated on R2-4 plates containing 40 µg/ml Cm. Clones that were both Cam resistant and Tet sensitive containing the fragment DNA were identified. Plasmid DNA prepared from one such clone was linearized at the BglII site located within the pdeA2 (SEQ ID NO: 2, nucleotides 98–2353) gene. The ends were repaired with T4 DNA polymerase. Approximately 400 ng of this 9.8 Kb fragment were ligated to approximately 400 ng of the 1.4 Kb EcoRI to AlwNI repaired beta-lactamase gene described above. The ligation mixture was used to transform E coli MM294; Amp and Cm resistant colonies were isolated. Mini-prep DNA from one such colony was analyzed by restriction digests to confirm the insertion of the amp gene in the coding region of pdeA2. The rest of the mini-rep DNA (2–5 µg) was linearized with BamHI and was used to transform strains 1306-3, 1306-21, 1306-3:ABT3 and 1306-21:ABT3. The ABT3 mutants contain the Str$^R$ gene introduced into the Bgl II site of pdeA2 (SEQ ID NO: 2, nucleotides 98–2353). The resulting mutants/transformants were designated 1306-3:ABT9, 1306-23:ABT9, 1306-3:ABT11 and 1306-21:ABT11 respectively. Phenotypically ABT9 mutants are Cel$^+$while ABT11 double mutants are Cel$^±$.

A strain in which the amp gene was inserted between the SmaI site upstream of the cdg1A (SEQ ID NO: 1, nucleotides 206–829) gene in cdg1 (SEQ ID NO: 1) operon was also made. This construction may have caused a disruption of the cdg1 (SEQ ID NO: 1) operon promoter. This strain was designated 1306-21:ABT8. Its phenotype is Cel$^+$ on R20-2 plates+50 µg/ml Amp.

X. Overexpression of DGC1 in Acetobacter

Attempts were made to overexpress dgc1 (SEQ ID NO: 1, nucleotides 3184–4923) in a mutant in which pdeA1 (SEQ ID NO: 1, nucleotides 856–3150) was inactivated. Only 15% of the PDEA activity remains in the mutant 1306-21:Dis1 (see table 4).

Experiments were performed to test whether overexpression of dgc1 (SEQ ID NO: 1) in this mutant may have a positive effect on cellulose production. A shuttle vector, pUC19-824:dgc1 was constructed to effect the overproduction of dgc1. A 3.5 Kb StuI fragment was isolated from the cosmid 3F3 which contains the cdg1 (SEQ ID NO: 1) operon. The StuI fragment contains approximately 350 bp of the 3' end of pdeA1 (SEQ ID NO: 1, nucleotides 856–3150) and the entire dgc1 (SEQ ID NO: 1, nucleotides 856–3150) gene. The StuI fragment was ligated into the SmaI site of the shuttle vector pUC19-824. The ligation mixture was used to transform the E coli strain DG101. The transformation mixture was plated on R2-4+50 µg/ml Amp plates on nitrocellulose filters. The colonies were probed with the dgc1 specific probe GE407 (5'-TGATCTGCTACGGGATAG-3'(SEQ ID NO: 47)). Several positive clones were identified. Two clones, one containing the dgc1 gene downstream from the lac promoter and the other in the opposite orientation were designated pUC19-824:dgc1 #8 and #11, respectively. Diguanylate cyclase activity in these strains was constitutively expressed at about 10% of the level in 1306-21. Mini-prep plasmid DNA from clones was used to transform the following strains: 1306-3, 1306-21, 1306-3:ABT3 and 1306-21:ABT3. These strains were designated 1306-3:ABT10, 1306-21:ABT10, 1306-3:ABT6 and 1306-21:ABT6/L1 and 1306-21:ABT6/S1, respectively. The 1306-21:ABT3 transformants has 2 colony phenotypes, large (L1) and small (S1) of the approximately 3000 1306-21:ABT3 transformants, 10 had a large colony phenotype) and the remaining had a small colony phenotype. Enzyme assays (see table 5) indicate that the level of DGC activity in 1306-21:ABT10 is approximately four-fold higher than Acetobacter 1306-21. All other tested enzymatic activities in comparable to the 1306-21.

XI. Biochemical Studies of cdg1 (SEQ ID NO: 1) and cdg2 Mutants

Table 4 is a summary of recombinant Acetobacter strains with disruptions in the cdg1 and cdg2 (SEQ ID NO: 2) operons. Table 5 is a summary of PDEA and DGC activity in the mutant strains given in percent of the wild type levels. The last column of Table 5 indicates the ability of each recombinant strain to inhibit the activation of cellulose synthesis relative to the inhibition in mutant 1306-21:Dis1.

The results indicate that cdg1 (SEQ ID NO: 1) operon codes for about 85% of PDEA and DGC activities and that cdg2 (SEQ ID NO: 2) operon codes for 5–15% of PDEA and DGC activities. cdg3 (SEQ ID NO: 3) operon probably codes for the remaining activities (1–5%). because inactivation of cdg1 (SEQ ID NO: 1) and cdg2 (SEQ ID NO: 2) operons results in 1 to 5% of PDEA and DGC activities. Extra copies of dgc1 (SEQ ID NO: 1, nucleotides 3184–4923) gene on pUC19-824 plasmid increase DGC activity by about 4 fold, compared to parent strain 1306-21.

TABLE 4

Summary Recombinant Strains with disrupted cdg Operon

| Strains | Mutation | Marker | Insertion Site |
|---|---|---|---|
| Dis1 | pdeA1 | amp | between EcoRV sites |
| Dis4 | dgc1 | amp | NruI |
| TRT150 | dgc2 | amp | EcoRV |
| ABT1 | pdeA1 | str | between EcoRV sites (ABT3) |
|  | pdeA2, dgc2 | amp | between PstI sites, one in pdeA2 (ABT2), one in dgc2 |
| ABT2 | pdeA2, dgc2 | amp | between PstI sites, as above, made from pTRT1343 (page 44) |
| ABT3 | pdeA1 | str | between EcoRV sites |
| ABT6 | pdeA1 | str | between EcoRV sites |
|  |  | amp | PUC 18-824 + dgc1 |
| ABT8 | upstream of cdg1A | amp | BglII |
| ABT9 | pdeA2 | amp | between SmaI sites |
| ABT10 | none | amp | PUC18-824 + dgc1 |
| ABT11 | pdeA1 | str | between EcoRV sites |
|  | pdeA2 | amp | BglII |
| ABT20 | dgc2 | str | EcoRV |
| ABT21 | dgc1 | amp | NruI |
|  | dgc2 | str | EcoRV |

TABLE 5

Summary of Strains

| Strain | Mutation | Synthase Activity | pdeA | dgc | Inhibition of Dist1 |
|---|---|---|---|---|---|
| 1306-21 | None | 100% | 100% | 100% | 90% |
| Dis1 | pdeA1 | 70% | 15% | 12% | NA |
| Dis4(*) | dgc1 | 83% | 65%* | 12%* | 55%* |
| TRT150 | dgc2 | 95% | 92% | 95% | 95% |
| ABT1, | pdeA1, dgc1 (PstI deletion) pdeA2, dgc2 | 76% | 5% | 1% | 0 |
| ABT2 | pdeA2, dgc2 (PstI deletion) | 98% | 89% | 121% | 70% |
| ABT3 | pdeA1 | NT | NT | NT | NT |
| ABT/6 | L1 Like DIS1 + PUC19-824 + dgc1 | NT | NT | NT | NT |
| ABT6/S1 | L1 Like DIS1 + PUC19-824 + dgc1 | NT | NT | NT | NT |
| ABT8 | Upstream of cdg1A | NT | NT | NT | NT |
| ABT9 | pdeA2 | NT | NT | NT | NT |
| ABT10 | None + PUC19-824 + dgc1 | NT | 100% | 500% | NT |
| ABT11 | pdeA1, dgc1, pdeA2, dgc2 | 105% | 3% | 5% | 0 |
| ABT20 | dgc2 | 100% | 125 | 109 | 105 |
| ABT21 | dgc1, dgc2 | 105 | 122 | 4 | 63 |
| 1306-43 Gene A | | 2% | 10% | 2% | 0 |
| C90-1 Gene A | | 3% | 18% | 20% | 0 |
| 1306-34 ? (cel-) | | 58% | 19% | 10% | 39% |
| B180-12 | | 25% | 47% | 9% | 52% |
| C90-14 | | 24% | 15% | 5% | 0 |

NA = Not applicable
NT = Not Tested
*= Average of two independent isolates, Dis1 = Dis2 and Dis4 = Dis7.

XII. Production of Cellulose in pdeA Mutant Strains

The recombinant strains of Acetobacter were tested for alterations in cellulose production levels. The construction of strains with the $P_L$ promotor operably linked to the cellulose synthase operon is reported in U.S. patent application Ser. No. 07/689,008, filed Apr. 22, 1991. Details on how to obtain cellulose from Acetobacter can be found in U.S. Pat. No. 4,929,550 and U.S. patent application Ser. No. 07/604,587, filed Oct. 26, 1990. The cellulose production of these strains was measured in flasks with Floxan EA-1340. The flasks were incubated at low agitation in order to provide the optimum conditions for cellulose production.

All seed cultures were grown in R70-3 medium plus 0.5% (w/v) TYE, 25 mM DMG and 0.1% (v/v) cellulase (1, 2, 3 cellulase Genencor). The 1306-21 seed cultures had 3% (w/v) glucose while the 1306-3 cultures were grown in 3% (w/v) fructose. The recombinant strains were grown in 100 ug/ml Amp. Some of the 1306-3 recombinant strains were originally isolated from relatively small or large colonies. These different isolates have the designation "small" or "large" respectively.

The test medium for this experiment was R70-3 plus 1 g/L Floxan EA-1340, 2% (v/v) E801A corn steep liquor (CSL) (corn steep liquor, from Corn Products Inc., Ango, Ill.) and 25 mM DMG. All 1306-21 strains were grown in 10 g/L glucose, while all 1306-3 strains were grown in 10 g/L fructose. All recombinant strains were grown in the presence of 100 ug/ml Amp.

The experiment was done in 125 ml baffled flasks (25 ml medium/flask). The seed flasks were incubated at 30° C., 125 rpm overnight, and then the cell mass in each flask was determined by $OD_{680}$ measurements. The 1306-21 test flasks received a 5% (v/v) inoculum, and the rest of the test flasks were given an inoculum of 3.5% to 9% so that all of the flasks would have the same cell mass at time 0. The test flasks were incubated at 30° C., 125 rpm for three days, and then the cellulose and cell mass were determined using standard procedures.

The results of the 1306-21 and 1306-3 cultures are given in Tables 6 and 7. All of the cultures had a final pH of 5.6–5.9. These high pH values have not been observed in previous glucose limited flask experiments. However, this experiment used E801A CSL, and E801A CSL media has relatively high levels of lactic acid. The high pH is most likely the result of the cells consuming the large amount of lactic acid.

Table 6 shows that 1306-21 strains containing either pABCD or P$_L$ produced similar levels of cellulose. Plasmid pABCD or pL contain sequences encoding the cellulose synthase operon and express cellulose synthase in bacterial cells, see co-pending U.S. patent application Ser. No. 07/687,008 for details on construction of these plasmids.

The results observed with the 1306-21 recombinant strains were not observed with the 1306-3 recombinant strains. Table 7 shows that the 1306-3 P$_L$ strain appears to produce less cellulose than the control. All of the 1306-3 cultures were grown in fructose in order to minimize pH problems.

All of the putative PDEA gene disrupted strains (1306-21 Dis1, 1306-21 Dis2 and 1306-3 Dis5) produced less cellulose than their respective controls. The 1306-21 putative PDEA disrupted strains also appeared to have a significant drop in the cellulose to cell ratio.

TABLE 6

Evaluation of Recombinant Strains In Flasks Growth in
R70-3 plus 1 g/L Floxan EA-1340, 2% E801A CSL and 10 g/L Glucose
Day 3 Results at 125 rpm

|  |  | Cellulose (g/L) | Average Cellulose | Cell Mass (g/L) | Cellulose/ Cell Ratio |
|---|---|---|---|---|---|
| 1306-21 | Control | 5.39 5.38 | 5.39 | 1.58 | 3.41 |
| 1306-21 | pABCD | 6.22 6.23 | 6.23 | 1.25 | 4.98 |
| 1306-21 | Dis1 | 4.90 5.01 | 4.96 | 1.79 | 2.77 |
| 1306-21 | Dis2 | 4.28 4.28 | 4.28 | 1.82 | 2.35 |
| 1306-21 | pL | 6.26 6.27 | 6.27 | 1.52 | 4.13 |

TABLE 7

Evaluation of Recombinant Strains Growth in
R70-3 plus 1 g/L Floxan EA-1340, 2% E801A CSL and 10 g/L Fructose
Day 3 Results at 125 rpm

|  |  | Cellulose (g/L) | Average Cellulose | Cell Mass (g/L) | Cellulose/ Cell Ratio |
|---|---|---|---|---|---|
| 1306-3 | Control | 5.44 5.32 | 5.38 | 1.57 | 3.43 |
| 1306-3 | Dis5 (small) | 5.16 5.08 | 5.12 | 1.33 | 3.85 |
| 1306-3 | pL | 4.76 4.90 | 4.83 | 1.54 | 3.14 |

Cellulose Production in Strains with Modified PDEA and DGC Activities

Various mutant strains were evaluated for alterations in their ability to produce cellulose. Seed cultures were grown up in R70-3 plus 25 mM DMG, 30 g.L glucose, 0.5% (w/v) TYE and 0.1% cellulase. The test medium for all experiments was R70-3 plus 1% (v/v) E801A CSL, 1 g/L Floxan EA-1340, 10 g/L glucose and 25 mM DMG. All recombinant strains except 1306-21:ABT3 has 100 ug/ml Amp in the seed and test flasks. Strain 1306-21:ABT3 had 40 ug/ml Str in the seed and test flasks. All test flasks received a 5% inoculum, and the flasks were incubated for three days at 30° C., 250 rpm (1" throw).

The results of the experiments are given in Table 8. The largest drop in cellulose production can be found in the double dgc1 (SEQ ID NO: 1, nucleotides 3184–4923)\dgc2 (SEQ ID NO: 2, nucleotides 2465–4186) mutant 1306-21:ABT21. 1306-21:ABT10 appeared to produce more cellulose than the control. 1306-21:ABT10 has dgc1 (SEQ ID NO: 1, nucleotides 3184–3923) overexpressed in the parental strain 1306-21.

TABLE 8

|  | Cellulose (g/l) | Average Cellulose | Cell Mass (g/l) | Cellulose/ Cell Ratio |
|---|---|---|---|---|
| 1306-21:ABT3 | 2.84 3.00 | 3.32 (61%) | 1.71 | 1.94 |
| 1306-21:ABT2 | 4.96 5.07 | 5.01 (99%) | 1.07 | 4.68 |
| 1306-21:ABT3 | 3.70 | 3.70 (68%) | 1.59 | 2.33 |
| 1306-21:ABT6/L1 | 3.90 3.52 | 3.71 (69%) | 1.88 | 1.97 |
| 1306-21:ABT6/S1 | 4.82 4.82 | 4.82 (89%) | 1.58 | 3.05 |
| 1306-21:ABT8 | 4.70 4.62 | 4.66 (86%) | 1.84 | 2.53 |
| 1306-21:ABT9 | 5.51 5.53 | 5.52 (102%) | 1.63 | 3.39 |
|  | 4.82 4.64 | 4.73 (98%) | 1.00 | 4.73 |
| 1306-21ABT10 | 5.80 5.76 | 5.78 (109%) | 1.50 | 3.85 |
|  | 4.82 5.07 | 4.95 (102%) | 0.97 | 5.10 |
| 1306-21:ABT11 | 3.25 4.09 | 3.67 (68%) | 2.29 | 1.60 |
| 1306-21:ABT20 | 4.70 4.94 | 4.83 (100%) | 1.13 | 4.27 |
| 1306-21:ABT21 | 1.87 1.60 | 1.74 (36%) | 1.79 | 0.97 |
| 1306-21 | 5.11 5.05 | 5.08 | 0.96 | 5.29 |
|  | 5.56 5.40 | 5.48 | 1.09 | 5.03 |
|  | 5.48 5.32 | 5.40 | 1.51 | 3.58 |
|  | 5.32 | 5.31 | 1.49 | 3.56 |
|  | 4.74 4.94 | 4.84 | 0.98 | 3.94 |

XIII. Probes for cdg Operons

Inspection of the DNA sequence in cdg operons revealed that genes pdeA1, pdeA2, pdeA3, dgc1, dgc2, and dgc3 share of highly homologous region of DNA. This region is contained within the 53 kb PCR product described in Example III, that was used to locate the three cdg operons. Table 9 describes the common region of homology with pdeA and dgc genes. The 53kb DNA probe can be used to indentify and clone cdg operons in other Acetobacter strains, in cellulose synthesizing bacteria or in plant cells and other cellulose synthesizing species. The hydridization conditions to utilize this probe are described in Example 3. To identify genes in other organisms, less stringent hybridization conditions may be used, e.g., lower temperatures.

Oligonucleotide regions specific to pdeA genes alone or to dgc genes alone were also identified. These probes include probes cel-141 GACAGCGAATCCCTGCTCA (SEQ ID NO: 48), and cel-142 CCGTGCATTTCCGCAAC (SEQ ID NO: 49), as specific probes for pdeA genes. These probes shared 100% homology within the three genes of pdeA. DNA probes TACTGGGTGGCCACCACC (SEQ ID NO:

50) and CATGGCCACCATGCG (SEQ ID NO: 51) located at nucleotide 3490 and 3760 of cdg1 operon, respectively, as specific probes for dgc genes. These regions also share 100% homology within dgc1 and dgc2 genes. These probes can be used to indentify corresponding pdeA and dgc genes in other organisms, as well as cdg operons. The hybridization conditions used may vary from stringent conditions for closely related strains and species, to less stringent conditions with more evolutionarily divergent organisms.

Antiserum prepared against oligopeptides encoded by these common regions can be used to identify PDEA and DGC peptides in other organisms in addition to screening expression libraries.

All patents, patent applications, and publications cited are incorporated herein by reference.

Equivalents

The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

TABLE 9

Common Domain Within the pdeA and dgc Genes pdeA1

```
GACAGCCTGACCGGCCTGCTCAACCGTGGCGCGCTG    (SEQ ID NO: 59)
 D   S   L   T   G   L   L   N   R   G   A   L       (SEQ ID NO: 53)
``` pdeA2

```
--------------G-----------CACGT-----    (SEQ ID NO: 60)
 D   S   L   T   G   L   L   N   R   T   S   L       (SEQ ID NO: 54)
``` pdeA3

```
--------------G-----------CTCCT-GG--    (SEQ ID NO: 61)
 D   S   L   T   G   L   L   N   R   S   S   V       (SEQ ID NO: 55)
``` dgc1

```
---CCG-----G--G---T----------T-GCT-C    (SEQ ID NO: 62)
 D   P   L   T   G   L   F   N   R   G   G   F       (SEQ ID NO: 56)
``` dgc2

```
--T-C--------------------C----GCT-C    (SEQ ID NO: 63)
 D   T   L   T   G   L   L   N   R   G   G   F       (SEQ ID NO: 57)
```

Consensus
```
 D   s   L   T   G   L   L   N   R   g   -   l       (SEQ ID NO: 58)
```

Biological Deposits

On Dec. 6, 1991, Applicants have deposited with the American Type Culture Collection, Rockville, Md., USA (ATCC) the cosmid pKT230COS5/5C10, described herein, ATCC accession no. 68860 cosmid pKt230COS5/3F3, described herein, given ATCC accession no. 68870 and cosmid pKT230COS5/15A8, described herein given ATCC accession no. 68871. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

What is claimed is:

1. An isolated polynucleotide comprising an Acetobacter cyclic diguanylate (cdg) operon gene, wherein said cdg operon is selected from the group consisting of cdg1 (SEQ ID NO:1), cdg2 (SEQ ID NO:2) and cdg3 (SEQ ID NO:3).

2. An isolated polynucleotide according to claim 1, wherein said polynucleotide comprises a polynucleotide vector.

3. A host cell transformed with a polynucleotide according to claim 2.

4. A method of producing a cdg operon protein, said method comprising the steps of
    culturing a host cell according to claim 3, lysing said host cell.

5. An isolated polynucleotide according to claim 1, wherein said cdg operon is cdg 1 (SEQ ID NO:1).

6. An isolated polynucleotide according to claim 5, wherein said polynucleotide comprises a polynucleotide vector.

7. A host cell transformed with a polynucleotide according to claim 6.

8. An isolated polynucleotide according to claim 1, wherein said cdg operon is cdg 2 (SEQ ID NO:2).

9. An isolated polynucleotide according to claim 8, wherein said polynucleotide comprises a polynucleotide vector.

10. A host cell transformed with a polynucleotide according to claim 9.

11. An isolated polynucleotide according to claim 1, wherein said cdg operon is cdg 3 (SEQ ID NO:3).

12. An isolated polynucleotide according to claim 11, wherein said polynucleotide comprises a polynucleotide vector.

13. A host cell transformed with a polynucleotide according to claim 11.

14. An isolated polynucleotide comprising a cyclic diguanylate (cdg) operon gene, wherein the cdg operon gene is capable of hybridizing under stringent hybridization conditions to a cdg operon selected from the group consisting of cdg1, cdg2, and cdg3.

* * * * *

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
( A ) LENGTH: 5904 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Acetobater xylinum ( x i ) SEQUENCE DESCRIPTION: SEQ ID NO:1:

| | | | | | | |
|---|---|---|---|---|---|---|
| GGGGGAAGCG | AAGTCCCGGT | CCATAACGGA | CGCTTACATC | ATATGCTCTG | ATATCCTGTT | 60 |
| AACCATTAAC | TGAAAGTATA | AACTGTCAGG | AATGGGCCAA | AATCCGGGGC | GGATATTCTG | 120 |
| TATCTATTTT | ACAAATTAAC | TTATGGCGAA | AATATGTCAT | TAATGAGATC | ATTCGTAATC | 180 |
| GCGTTGAGAA | CAGAAAAAAA | TTAACATGTC | TCTTGTGCAG | CCTTCTCTGT | CTTCTGATGG | 240 |
| AACGAAACGG | ACATTTTCCG | AACGTCAGGA | ATTCATGACG | GAAGATATGC | CCGCCAGCAT | 300 |
| GCATTTCCAT | GTGGTGTCCG | GAGGCGCGCG | CCTTTTCAAA | TCCCTGCCTG | ACGGGCGGCG | 360 |
| GCAGATTATC | GGTTTTGCCC | ATAAAGGCGA | TGTGCTCCCC | GCCTATCCCT | GCACCCGCTA | 420 |
| CCATTACAGC | GCCGAAGCCA | TGCGCAGCCT | GCAGGTGGTG | TGCGTGCCCG | CGCCCTATCT | 480 |
| GAGCCACCTG | CATGAAACCT | CGCCCGGTGC | TTGCGCGGCT | TCGCTGAATT | CCGCCCGCCA | 540 |
| GTTGCTGGTC | AGCCTGCATG | CCCGGCTGCT | CATGCTTGGC | CGCCAGACCG | CGCGCGAGCG | 600 |
| CCTGGCAACC | TTCCTGCTCG | GTCAGGGCAC | GCGCATGGGG | CCGGGTGAAC | TCTGGCCCGT | 660 |
| TGATCCGTCC | ATTTCACGTG | CGGACATGGC | CGATTTCCTT | GGCCTGACCA | CCGAGACTGT | 720 |
| CAGCCGCCTG | CTCAGTGCCT | TCCATCGGGA | GCAGCTTATC | TGCCGGGAAC | GGCGCGCCAT | 780 |
| CCATATTCTC | GATCCTGACC | GCTTGCGGGC | GATCGTGGCC | CACCCAGAAT | GACAGCGAAG | 840 |
| AAAGACAGCA | CGACGATGCC | CGACATCACA | GCCCTCACCA | CAGAAATCCT | TCTTCCCGCC | 900 |
| CTTGAGCAGG | CCATTGATGC | AACTGTCATC | ATCGGGCAGG | AAAACGAGAT | CATCTTCTAT | 960 |
| AACCAGGCGG | CGGAATCCCT | GTGGGGCATT | CCCCGCGCCG | ACGTGATCGG | CCGCAATGTC | 1020 |
| GACTGCCTGG | TGCCCACCCG | CCTGCGCCAT | GAGCATGACC | GCTACATCGA | CCGCAACCGC | 1080 |
| GAGACCGGGC | ATAACCGCAT | TGTCGGCACA | TCGCGCGAGG | TGGAGTTCAC | CCGCGCCGAT | 1140 |
| GGGGAATACA | TCTGTGGCGA | GCTTTCGCTC | TCCAAGGTGC | AGATCGGCCA | GGGCGACAAG | 1200 |
| CGGCTCACCT | ACTACATGGG | CGTGATGAAG | AACGTCACGG | AGGAGAGCCA | GCGCCGCAAG | 1260 |
| ATCCTGATCC | TGCAGAACGA | CGTGCTGCAG | GCGCTGGCCA | GCGACATGCT | GATCCAGGAT | 1320 |
| ATTGGCGAGC | TGATCTGCCG | CAAGGTTGAA | GCCTTCGTGC | CAACTCGGT | CGCGGCCTTG | 1380 |
| CTGGTGCTCG | ATGATGCGCA | GCCTTGGCGG | GTGATCTGCA | CCTCCGCCCT | GCCGCCGCGC | 1440 |
| ATCCGCAATG | CGCTTGAAAC | CACCGTGCCG | TCACCTTCGG | ATGTGGAAAA | GCTCAAGGCC | 1500 |
| AATGCCTCCT | ATACCGGCCA | CCTAGTGTGG | AACAACTACC | AGTCCATGTG | CCGCTCGCTG | 1560 |
| GGGCTGCAGT | CGTGCTATGC | GGCGCCGGTC | ATGGCTGGTG | ACGGGCGGGT | AACGGGCATC | 1620 |

-continued

```
TTCGCACTGT  ACCTGCGCGA  GCCCAACCAG  CTTGGCGCGT  GGCCGCAGCG  CCTTGTGGGG   1680
GCGTGCCTGC  CCTTCTGCGC  GCTGGCGCTG  GAGCAGCACG  CCACCAAGAC  CCACCTGACC   1740
CAGCTTGCCC  GCTATGACAG  CCTGACCGGC  CTGCTCAACC  GTGGCGCGCT  GCATCGCGTG   1800
ATGGAAGACA  TCATCGCCCA  GCCCGGCAAC  CGCACGCTGG  CCATCTTCAT  GCTCGATATC   1860
GACCGTTTCC  GCGATATCAA  CGATGCGCTC  GGCCATGTCT  ATGCCGACCA  GTTCCTTGTC   1920
GAGATCGCAG  GCCGCATCCG  CTCCATCGCC  AAGGACGATT  ACGTGCTCAG  CCGCTCGGGT   1980
GGTGATGAGT  TCGTGGTGGT  CGTGCCGGAT  TGCGAAGGCA  AGCAGATCGA  GGAAATTGCC   2040
CACAAGCTGC  TCGAAACCAT  CGGTCGCCCG  CTCCAGATCG  GGCAGAATAC  GCTGTCTATC   2100
TCGTGCTCGA  TCGGCATCAG  CACTTTCCCC  GCCAACGGGC  CGGACAGCGA  ATCCCTGCTC   2160
AGCCATGCCG  ATACCGCCAT  GCGGCAGGCC  AAGGAAGACG  GCGCGGCAT   CTTCCGCTTC   2220
GCCAATCTCG  AGAAAAACCA  GGTGGCGCAG  GACCGGCTGG  TGCTCGGCTC  GGCGCTGCGT   2280
GATTCGCTGG  CGCAGGGCAT  GCTGCAACTG  CATTACCAGC  CGCAGGTGCG  CACCCACACG   2340
CTCGAACTCA  GCGGTGTCGA  GGCGCTGTCA  CGCTGGCATC  ATCCGCATCT  TGGCAATATC   2400
TTCCCCTCGC  GCTTCATCGC  CGTGGCGGAG  GAGACCGGCC  AGATCGAGGC  CATTGGCCGC   2460
TGGTCGCTGC  TCGAGGCCTG  CCGCCAGATC  GTGAAGTGGG  ACCGCGACGG  CATCCATGTG   2520
CCCACCGTGG  CCGTGAACCT  GTCTGCCGTG  CATTTCCGCA  ACCGCGCGCT  GCCCGAGCAC   2580
ATCGCGGCGC  TGCTCAAGGA  CCATAACCTC  AAGCCTTCGC  GCCTGACGGT  GGAAATTACC   2640
GAGAGCGTGA  TGATGGATAA  CAGCCGCGAC  ACCGAGGAAG  TGCTCCAGTC  GATCCGCAAT   2700
ATCGGCTGTG  GCCTGTCGAT  GGATGATTTT  GGCACCGGGT  ATTCATCGCT  CTCGCGGCTC   2760
ACGCGCCTGC  CACTGACCGA  GATCAAGATC  GACCGTAGCT  TCATCAACGA  TTTTGAATAC   2820
GACACCAACG  CCCAGGCCGT  GACCATGGCG  GTGATCGGCA  TCGGCTCGCG  GCTGGGCATG   2880
ACGGTCGTGA  CCGAAGGCGT  CGAGACCGAG  CAGCAGCGCG  ACCTGCTGGA  GAAACTCAAC   2940
TGCGACGTGA  TGCAGGGCTA  CCTGTTCGCC  AAGCCGCTGG  CGCCGCAGGA  TCTTGAATCC   3000
TGGGTGCGCC  GTGGCGGAGC  GCCTGCGGTC  ATTCGTGAAA  TTGAGGCAGC  CCGCGCCAAG   3060
AAGGGTGGCA  AGCCCGAAAG  CAGCGGCAAA  AAAGACGGTG  CCCCTGCAGC  CAAGCCTGCT   3120
GCTGCAAGCC  CCGCAACCCC  CGAAAAGTCC  TGATCTGCTA  CGGGATAGAT  GGAGCCATAC   3180
GCCATGTCAC  TCAAGCACGA  TGATCGCCTG  CGCGCGCTGA  CCCACCAGGA  TTCGGATTTC   3240
TGGGCCGATG  TTGTGGACAA  TGTCCTGATC  GTGGCCATTA  CCGATGTGCG  TGGTGTGATT   3300
ACCTATGTGA  ATGACCGCTT  TTGCGAGATC  AGCCGCTACC  CGCGTGAAGA  ACTGCTGGGG   3360
GCGACGCATC  GCATCGTCAA  TTCCGGGTAT  CATGATGCGA  GCTTCTTCAG  GCAGATGTAC   3420
CGCACCATCC  GGGGGGGCGA  GATATGGCGC  GGCAATATCT  GCAACGGGC   CAAGGATGGC   3480
ACGCTGTACT  GGGTGGCCAC  CACCATCATG  CCCAAGCACA  ACTCGCTTGG  CGCGGTTGAG   3540
GGCTATGTCG  CGACCCGTTT  CGAGATTACC  GAACTGATGA  ACACCCGCGA  CCGGCTCAAG   3600
TCGCTTGCCG  CGACCGACCC  GCTGACGGGG  CTGTTCAACC  GTGGTGGCTT  CAACAACGTG   3660
CTCCAGACCG  CAGTGGAAGA  TAAATCGCAG  AACATTACCC  GCGACATCAT  GCTGGTCATG   3720
TTCGATCTCG  ATGGCTTCAA  GCAGATCAAC  GACATTCATG  CCACCATGC   GGGCGATGTG   3780
GTGCTGAAGG  TGATTTCCAA  CCGCCTTCTG  GCGCTTGTCC  ACCCTGAAGA  TGCGGTCTGC   3840
CGGCTGGGGG  GCGATGAGTT  TGCGCTCATC  CTCAACCATA  CGCTGCATAA  ATTTCCGCTT   3900
TCCCTCATGC  TGGAGAAGCT  GCTGGCCGAG  CTCGAAGCGC  CGATCGAGGT  GGGCAACACC   3960
ATGGTCAACG  TGTCGGCAG   CATCGGGGTC  ACCCCCATCG  CCAGCCAGGA  AAGTGCCGAA   4020
```

```
TCGCTGCAGA AAAATGCCGA TATCGCGCTT TATGCCGCCA AGCGCGCGGG TGGCCACCAG      4080

GCGCGCATGT TTGACATGAC CCTGCACCAG CATGCGCTGG AGCGGGCGCA GATCCTCAAT      4140

GATGCGCGTG AAGGGGTGAT GAAGGACCAG TTCGAGCTTT ACTACCAGCC GATCATGAAC      4200

TTCAGCACCG GCAAGTGCGA CCAGATCGAG GCGCTGCTGC GCTGGCACCA CCCGCAGCGC      4260

GGCCTGCTGG CGGCGGAAAG CTTCCGCGAT GTATTCCTTG ATGCGGCTCT GCGCAGGTC      4320

ATGAGCCCGC GCCTGGTCAA GTCCTTCCAG AATGACATGC GGATGTGGAA TACAAGCCTC      4380

GACGCGTATC CCAACCTGAC CATCAATCTC TCGCGGCTGG ACCTGCTCAA TATCGGCTTC      4440

CAGAATGACC TTGAGGCTGA AATAAAGCGG CAGGGTGGCA AGGCGGCCGA TTACGTGCTG      4500

GAAATATCGG AAAGCGTGCT GGCGGGCAGG CGCTCCGATC GTGTGCTGCA GCGCCTGCAG      4560

GAACTGAGCG AACTCGGCTT CCAGCTAACG CTCGATGATT TCGGGCTGGC GACGCTGCCA      4620

ATCTCGGTTC TGCGCACGAT TTCCTTCACG CAGGCCAAGA TATCACGCAA GCTGGTCAAG      4680

GACATTGAAA CCAGCCCGCA GGCGCGCGGC GTGGTGGCGC ATCTGATTGG TCTGGCACAT      4740

GCGTTCGGGC TGAGCGTGAC CGTGAGCGGC GTGGAAACCA AAGGCCAGAT GGAGGTCCTG      4800

CGCGAGATGG GTGCCGACCG AATTCAGGGT TTTTATATTT CTCCCCCGAT TTCTGCTGCG      4860

AATCTTGTGC TTGCGGAGCA CATCATTGCG CCAGATCATA CCGAGATCAC GTTACAGGCG      4920

TCATGACACG CCATGCGCCT TACTTTATAC ACCGACTACT CCATTCGAAC CCTTATCTAC      4980

CTTGGGCAGA ACCCGGGTAG ACGGGTTGCG ATCCAGGAGA TTGCTGCGAC GCACCGCATT      5040

TCCCAGAATC ATCTGGTCAA GGTGGTGAAC CGTCTGTCCA GCAACGGTGT CATTCTGGCG      5100

CGGCGCGGGC GCAGTGGCGG CCTGGAACTT GCCGGTGCGC CGCACCAGAT CATTATTGGC      5160

GATATCATCC GCCTTATGGA GGCGGATATG GGCAAAATTG TGTCCTGTAA TCCTGAAAAC      5220

GGGCAGGCGT GCGTATTGGC TGATGCATGT CGCCTGCAAG GACTGTTTGC CAAATCGGTC      5280

AATGCCTTCA TGTCGGTACT CGATCGCATT ACGTTGCATG ATATCCTGCA TGAGCCTAAG      5340

AAACTGTAAA ATCAGGCTCA TGCAGGCAGG CTGAAGGCAT GTGACCCGCT GTGCATGCGA      5400

TGCGCATGGG ATTGAAAAAT CGCGCGTATC GGAATGCTCA GTGTCATCCA ATGATAAGCC      5460

TGACTTATGA TGAGATAATA TTTATCTATA AGTCAGGAAG GCTACATTTT CTGGTTGCAA      5520

TAAGGACGGC ATAGGTCTTT TTTGGTGTGG CATGAGGAAT TTGGCTCACA CAGTGTAATA      5580

ACAGGAACAC CATGCCCGC ACGCCGTTGC CTTGGCCTAC CGTCTGCTCC TGCATCATGC       5640

AGGCGGCCTT TAAAAGACAG GGAGCCAGAG CCGAGATACT ATGCGCCTGA CCCTTCATAC      5700

CGACTATGCC ATTCGTGTTC TGGTTTATCT GGGGCAAAAC CCTGGTCGAC GCGTTTCAGT      5760

GCATGAAATT TCGGAAAATC ATGGCATTTC CCATAATCAC TCGTCAGGTG GGGTCAAATC      5820

GGCTCTCTAC CACGGGTTTG GTCGGATACC CGTCGGGGGG GGGCAGGGGG GTTTGGAACT      5880

GCCGCGCATG CCGCATGAAA TCGG                                            5904
```

( 2 ) INFORMATION FOR SEQ ID NO:2:

( i ) SEQUENCE CHARACTERISTICS:
        ( A ) LENGTH: 4558 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Acetobacter xylinum ( x i ) SEQUENCE DESCRIPTION: SEQ ID NO:2:

| | | | | | |
|---|---|---|---|---|---|
| GGCATAAATC | ATAGTATGAT | GCCTCGCCGA | GTGGTCCCGA | TGCCTGTTTC | CGCATGGCCA | 60
| TGATCGAATC | TGACCGCTTG | ATGACGCCGC | CAGGCGGATG | CCTGCCCAGG | TCAGGAAAAT | 120
| GATCTTACAT | GGCGCGGTTG | GGCGTGCCGA | TGTTCTGGAG | TTTACGGTGG | ATCAGCCGAA | 180
| GATTAGCGCC | GATGTCCTGC | TTTCTGCTAT | GGAGCAGGCC | ATTGATCCCA | TGGTCGTGAT | 240
| TGATGAGCAT | AACCTCATCA | TCTTCTTCAA | CGCGGCGGCC | GAGAAGATAT | GGGGCTGCTC | 300
| GCGCGAAGAG | GTCATGGGTC | GCAATGGAGC | TGCCTGGTGC | CCGAACCCGA | GCGCGATCGC | 360
| CATGATGACT | ACATCAACCG | CAATCGCGAG | ACCGGGGTCG | GCCGGATTGT | CGGCACCTCG | 420
| CGCGAGGTCG | AATTCCGTCG | CGCCAATGGC | GAGTATGTCT | GTGGCGAGCT | GTCCATCTCG | 480
| CGCGTGCAGG | TGAATGATTG | CGGCAAGATC | TACTACATCG | CGGTCATGAA | GGACGTGACC | 540
| GAGCAAAGCC | GCCAGCGCAA | GATACTGGTG | CTGCAAAATG | ATGTGCTCCA | GGCCCTCGCA | 600
| TCCGACATGA | GCATACAGGA | AGTGGGCGAC | CTGCTGTGCC | GCCGGGCGGA | CAGTTTCGTG | 660
| CCCGGCGCGG | TTGGCGCGCT | GATGCTGATC | GACCCGTCGC | GCAGGCTTTC | GGTCAGTGCC | 720
| TCGCCCTCCT | AGCCCAAGGC | TACCGCGCGG | CACTCGACAG | CATGCAGCTT | ACCCCCGAGC | 780
| AGCTTGAAAT | CGTGCGCGCC | AACCCCGCCG | GCAGCAACAC | CGTGGTGTGG | GATGCTACGC | 840
| CTCGCTGGCC | CGCTCGCTGG | GGTTGGAGCG | GTGCTGTTCG | TCCACCATCA | TCTCGCGCAC | 900
| GGGGCAGGGT | CATGGGCGCT | GTTCGCGCTG | TACCTGCGTG | GCGACGAGGC | CGATCTGGCC | 960
| TGGGCGCAGC | GCGTGGTCTC | GACCAGCATG | CCGTTCTGCG | CGCTGGCCAT | CGAGCAGAGC | 1020
| GAGACGCGCC | AACATATCGC | CCAGCTTTCC | AATTTCGACA | GCCTGACCGG | GCTGCTCAAC | 1080
| CGCACGTCGC | TGCACAATAT | CATCGAGCGC | CTGATCATGC | GCGGCGGCGA | CAGCCAGTTC | 1140
| TCGCTGTTCA | TGGTTGATAT | CGACCGCTTC | CGCGATATCA | ACGACGCGCT | TGGCCATGTG | 1200
| AATGCCGACC | GCTTCCTCAT | AGAGATCGGT | CGCCGCATCC | GCCATCTGGT | CAAGGATGAA | 1260
| TACATTGTCA | GCCGCTCCGG | CGGTGATGAG | TTCATCATCG | TCGTGCCTGA | ATGCTCGCAT | 1320
| GAACGCGCCG | AGAAATTTGC | CGAGAACCTG | ATCAACGCCA | TCGCCAGGCC | GCTGCAGGTG | 1380
| GGCGAGAACA | CGCTCAGCAT | CTCGTGCTGC | GTTGGCATCA | GCACCTTCCC | CGCCAACGGG | 1440
| CCGGACAGCG | AATCCCTGCT | CAGCCATGCC | GATGCCGCGA | CCCGCCAGGC | CAAGGAGGAC | 1500
| GGGCGTGGCC | TGTTCCGCTT | TGCCGGCCAG | GAAAAGAACC | AAGTGGCGCA | GGACCGGCTG | 1560
| GTGCTGGGCT | CGGCGCTGCG | CGATTCGCTC | TCCAAGGGCA | TGCTCAACCT | GAACTACCAG | 1620
| CCGCAGGTCG | AGACCATGAC | CGGCGGCCTT | TACGGGGTGG | AGGCGCTCTC | GCGCTGGCAT | 1680
| CACCCCACGC | TGGGCAACAT | CTATCCCTCC | CGCTTCATTC | CGTGGCGGAG | GAGACGGGCC | 1740
| AGATCGAGGC | CATTGGCCGC | TGGTCGCTTG | AGGAAGCGTG | CAGCCAGATG | GTGAAGTGGG | 1800
| ACCGCGACGG | CGTGCGGGTG | CCGACCGTGG | CGGTCAACCT | CTCCGCCGTG | CATTTCCGCA | 1860
| ACCGCGGGCT | GCCCGAGCAC | ATTGCCAACC | TGCTCAAGCA | CCATGGCCTG | CGCCGGACC | 1920
| GCCTGACGGT | GGAAATAACC | GAGAGCGTGA | TGATGGACAG | CAGCAGCGAG | ACCGAGGAGG | 1980
| TGCTGCATGC | CATCCGCAGG | CTTGATGTCG | GGCTGTCGAT | GGATGATTTC | GGCACGGGGT | 2040
| ATTCATCGCT | CTCGCGGCTG | ACCCGCCTGC | CGCTGACCGA | GATCAAGATC | GACCGCAGCT | 2100
| TCATCAACGA | CTTCGAGCAT | GACACCAACG | CCCAGGCCGT | GACCATGGCA | GTGATCGGCA | 2160
| TCGGCTCGCG | GCTGGGCATG | ACGGTGGTGA | CCGAAGGCGT | GGAAACCGAG | CAGCAGTGGC | 2220
| GCCTTCTGGA | GGAATTGCAT | TGCGATGTGA | TGCAGGGCTA | TCTTTTCTCG | AAGCCACTAC | 2280

-continued

```
CGCCAGCGGA ACTGGAAAAA TGGTTCCGCG AGCGGCAGGA GCGTGGCTCC TTCCTTATTC    2340
CAACGACGGC ATAGAGCATG TGGTGCCCCG CACTGGCACC GGTGTTTCAG GGGCATGCGG    2400
GGGCCGGTTT GAGTTCATGA CGCATAACAG TTTGTTTTTC ATTACGGATT CCAGGCGGGA    2460
ACATGGCATT GCAACACGAT GATCGGCTGC GGGCCCTGAC GCACCAGGAT GCGGATTTCT    2520
GGGCTGATCT GGTTGATAAT GTCCTCATTG TCGCGATTAC GGATAGCGAG GGGGTCATCA    2580
CCTACGTGAA TGACCGCTTT TGCGAGATAA GCCAGTACTC GCGCGAGGAA CTGGTGGGAT    2640
CGACGCACCG GATCGTCAAT TCCGGCTACC ATGATGCCGA TTTTTTCCGG GATCTGTACC    2700
GCACCATCAA GGCGGGGCAA CTGTGGCGGG GCAATATCTG CAACCGCGCC AAGGATGGGT    2760
CGCTGTACTG GGTGGCCACC ACCATCATTC CAAGATCGA CCGGCAGGGC ACGATTACGG    2820
GGTATGTGGC CAGCCGGTTC GAGATTACCG AACTCATGAA CACGCGCGAC CGGCTGTGTG    2880
AACTGGCCGA GACCGATACC CTGACCGGCC TGCTCAACCG CGGCGGCTTC AACACGGCGC    2940
TGGCCGATGA GATCGCGCGC TGCCGCGAGC CGGGCATGAC CGCCCACCCG GCACTTGCCA    3000
TGTTCGACCT CGATGGCTTC AAGCAGATCA ATGACGTGCA TGGCCACCAT GCGGGTGACA    3060
TCGTGCTGCG TGCCATTGCC TCGCGGCTGA TCGAGCTTAC CCACCCCGAT GATCCGGTCA    3120
GCCGGCTGGG TGGCGATGAG TTTGCCGTCA TCCTGCACCG CACGCTCGAG GATGTATCGC    3180
TTGAGCGGTA CATGGACCGC CTGCAGGCCA TCCTTGAACG CCCCATCGAT ATCGAGACGG    3240
TAACGGTGAG CGTTGCGGGC AGTATTGGCG CGGTGCTGCT CGATGGCACC GACACGATGG    3300
AAGACGTGCA GAAAAACGCC GACATGGCGA TGTACGCTGC CAAGCGCGCG GCGGCAAGC    3360
AGTCGCAGAT GTTCACCAGG AACCTGCGCG AGCGCGCACA GGCGCGTGTC TCGATCCTGA    3420
GCGAGGCGCG GTGCGGGGTC GAGCGCAACC AGTTCGAGGT CTATTACCAG CCGATCGTGA    3480
ACTGCAACAC GATGGAGGTG GACCAGATCG AGGCGCTGCT GCGCTGGCAG CACCCCGAGC    3540
GCGGGCTGCT CGCGGCGGAA GACTTCTCCG ACGTGTTTAC CGATGCGGGC CTCGCCCAGG    3600
CGATGGGGCC GCGCATGATC GAGGCCTTCC GGCGCGATGT GTGCATGTGG AACGAGAAAG    3660
GCCAGCCGCC GCGCCAGCTT GCCATCAACC TCTCGCGCAT GGACCTGATC CGCGATGACT    3720
ACCAGCGCGA GCTTGAGGAA TCGCTGCGGC GCTTCAACAT GTCGCCCGAC AGCTTTGTGC    3780
TGGAAGTGAC GGAAGCCATG CTGCATGGCC GCCGGGCCGA GCAGGGCATC CGCAACCTGC    3840
GTGAACTGGC GCGGGCGGGT TTCCGGATCG CGCTTGATAA TTTCGGCAAG GGCATCACGG    3900
TGCTGAACCA CCTGCGCGAA CTGCCGTTCT CGCAGGTCAA GATCGACCAG AGCATGGTGA    3960
CTAACATCGT GGGCAACCCC GATGCCTGCA TGGTCCTGTC CAGCCTGATC GACATGGGGC    4020
AGGGCTTCAA CATGGAAGTC ACGGTCGAGG GTGTTGAAAA CCGCGAGCAG TTTGAACTCG    4080
TCAAGGCGCT CAGGCCCGAG CGCATCCAGG GTTTCTTTGT CTCGTCTGCA CTGTCTTCCC    4140
AGGATATTCT CAAGCTGCCC GCGCGTTTTG AAGGGGTGAC GCTGTGAGCG ATGATGCGCC    4200
CCGCATGGTG GCCGCGCGCA TTGGCGATGA CCTGCCGCGC GTGGACGTGA TTGAGCTGGC    4260
CAATACGCGG CGCATCATGC ATGCGGAGCG GCATAATGAT GGCTCGCGCA TGCCCATGTT    4320
CATTCCCGCC GCCTCATGGG CGCGGTTGCT GGAACTGCAT TGCACGGGGG AGGGCGACCG    4380
GCCCCGCCTC GCGCCCTCGC GTGTCATGGA CGGGCTCGAG CGCGCCCTTG GCCGTATCAT    4440
GACCGAGGTG GTGCGCCATG ATGCGGCGCA GGACGCGCCC TTGCGCCCGG TCTATGATGT    4500
CACATCCGAC CTGTTCGGGG CGGAGGAAGG GCCGGTCGAG ATCCGCATGC TTGTTGAC    4558
```

( 2 ) INFORMATION FOR SEQ ID NO:3:

( i ) SEQUENCE CHARACTERISTICS:
    ( A ) LENGTH: 4131 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Acetobacter xylinum ( x i ) SEQUENCE DESCRIPTION: SEQ ID NO:3:

```
GAAACCCCCC CCCCCCCAAG GGGGGGATGT GGCGGCCTGG TTCGGGCTTG CGCGGGCAAG        60
GGATTGCGGC CCCCCAAAAC CTTGACATAT GTGGAATATG CAATTTTGCG TGCGGGATGT       120
GATGGATCAA CCGCCTGCGA ATGCTATATG GACGCATCCA TTCCAGACGG AAATTATTAA       180
AGACGACCTT AATTCATATC AATGTGGTAT AATGATTATC TTGAATAATA TGTAATATGC       240
TTATCATCAT CCTATGATAT TCCTGCGGCC GCCATGCACT GTGCCCGCCC GGGTGATGGC       300
GCGCCCTGCA TTTCCGGTCG CCTTATATAC CCCTGCTGCA GCCGCCTGCC GGTGGCTGCC       360
CCTTGTCCCT TTTGCGAGGT AACTCAATGT CAAAGCCTAA CCTGAGCGCT GAAGTCCTGA       420
TTTCGGCACT GGAGCAGGCC ATAGACGCAA CCGTGATTAT TGATGACAAG AACGAAGTCA       480
TCTTCTTCAA TCAGGCGGGA TCGAACCTGT GGGGCCTCGA CAAGAAAGAT GTGCTGGGCA       540
AGAACGTGAA CGTGCTGGTG CCCACGCTGC ATCAGGCCGG GCACGACGCC TTTGTCGAGC       600
GCAGCCGGGG CAGCTCGCAT AACCGCATTG TCGGCACCTC GCGCGAGGTG GAGTTCACCC       660
GCTCGGATGG GGAATATATC TGCGGCGAGC TGTCGCTGTC CAAGGTCGTG AACGATGACA       720
AGCGCATCTT TTTCATGGGC GTATGAAGAA TGTCACCAAC GAAAGCCAGC AGCGCAAGAT       780
CCTGATCCTG CAGAACGACG TGCTGCAGGC ACTCGCCAGC GACATGATGA TCCAGGACGT       840
GGCCGACCTT CTGTGCCGCC GGGTGGAAAG CTTCGTGCCC GGCACGGTGG CCGTGCTCAT       900
GCTGATTACG CCAGACGGGC AGTTGCGCGT TCTGTCCAGC CCCACACTGC CAAGCGCTA       960
CCGCGCCTCG CTCGAGAGCC TGTATGTCTC GTCATCCGAA CTCGAGAAGC TGCGCGTCGA      1020
TCCCAAGCAC GCCACCCGCA TGGTGTGGGA CAGCTACCGC TCGCTCGGCA TCTCGCTTGG      1080
CCTGCAGCAG TGCTTCTGCA CGCCCGTCAG CACGCGTTCA GGGCAGGTGA AGGGCATTTT      1140
CGCCCTCTAT TCGCGTGAAG ACCAGGGCCG CAACACGTGG CCGCAGCGCA TTGTTGATTC      1200
GTGCATTCCC TTCTGCGCGC TGGCCTTTGA ACAGAATGCA ACGCAGGAGC ATATCTCCCA      1260
CCTTGCCAAT TTTGACAGCC TGACCGGGCT GCTCAACCGC TCCTCGGTGC ACAAGGTGAT      1320
CGAGGGCATG ATCAGCAAGC AGGATGGCAA CCGGCAGTTT GCCATCTTCA TGCTCGATAT      1380
CGACCGTTTC CGCGATATCA ACGATGCGCT CGGCCATGTC TATGCCGACC AGTTCCTTAT      1440
CGAGATCGCA GCCCGCATCC GTTCCATCGC CAAGGAGGAT TACGTGCTCA GCCGCTCCGG      1500
CGGCGACGAA TTCGTGGTGG TGGTGCCCGA CTGCCCGCAC AAGGAAGCCA CAGACTTTGC      1560
CGAGCATCTG CTCGCTTCCA TGACCATGCC CATGCAGATT GGCCAGAACA CGCTGACCAT      1620
TTCATGCTCC ATTGGCATCA GCACCTACCC CGATAACGGG CCGGACAGCG AATCCCTGCT      1680
CAGCACCGCC GATGTGGCGC TGCGCCAGGC CAAGGAAGAC GGGCGCGGCG TCTTCCGCTT      1740
CGCCAATCTC GAGAAAAACC AGGTGGCGCA AGACCGGCTG GTGCTCGGCT CGGCGCTGCG      1800
TGATTCGCTG GCCAAGGGCA TGCTCAACCT GCACTACCAG CCGCAGGTGC GCACCCACAC      1860
GCTCGAACTC AGCGGCGTCG AGGCGCTGTC GCGCTGGCAT CATCCGCATC TTGGCAACAT      1920
```

-continued

```
CTTCCCCTCG CGCTTCATCG CCGTGGCGGA AGAGACCGGC CAGATCGAGG CCATTGGCCG   1980
CTGGTCGCTG CTCGAGGCCT GCCGCCAGAT CGTGAAGTGG GACCGCGACG GCATCCATGT   2040
GCCCACCGTG GCCGTGAACC TGTCTGCCGT GCATTCCGC AACCGCGCGC TGCCCGAGCA    2100
CATCGCGGCG CTGCTCAAGG ACCATAACCT CAAGCCTTCG CGCCTGACGG TGGAAATTAC   2160
CGAGAGCGTG ATGATGGATA ACAGCCGCGA CACCGAGGAA GTGCTCCAGT CGATCCGCAA   2220
TATCGGCTGT GGCCTGTCGA TGGATGATTT CGGCACCGGG TATTCATCGC TCTCGCGGCT   2280
CACGCGCCTG CCGCTGACCG AGATCAAGAT CGACCGCAGC TTCATCAACG ATTTCGAGCA   2340
TGACACCAAT GCCCAGGCCG TGACCATGGC GGTGATCGGC ATCGGCTCGC GGCTGGGCAT   2400
GACGGTGGTG ACCGAAGGCG TGGAAACCGA GCAGCAGCGC GACCTGCTGG AAAAACTCAA   2460
CTGCGACGTG ATGCAGGGCT ACCTGTTCGC CAAGCCGCTC GCACCCGATG ATTTCGAGAA   2520
GGGATGCGCC ACCACCAGAC GATCCGGCAA ATGCTGCCGC CGCGCCGGCT GCCAAAAATG   2580
TTTCGTCAAA AAAGAAAACA TCCTAAATTA CCAATAGGTC AATTAAGGTT TTTCGATCCG   2640
TATCCGAGGT AACAGAATGT CCGCACCGCA TGATAACAGG CTCCGCGCCC TTACACATGA   2700
AGATGCCGAC TTCTGGGCGG ACGTGGTGGA TAATGTCCTT ATTGTTGCGG TCACCGACCG   2760
CAAGGGCATC ATTACCTACG TCAATGATAA ATTCTGCGAG ATCAGCCAGT ATTCCCGTGA   2820
GGAACTGCTG GGCCATACCC ATCGCATCCT GAACTCGGGC GAGCACGGGA AGGCCTTCTT   2880
CCGCGAGATG TACCAGACCC TGTTCTCGGG CCGGACCTGG TATGGCAATT TGTGCAACCG   2940
CGCCAAGGAT GGCAGCCACT ACTGGGTGGC CACCACCATC ATGCCGCACC GCAATGCCAA   3000
GGGCGAGATT ACCGGTTTCG TGGCCAGCCG GTTGAAATC ACGGAACTGA TGAACACCAA    3060
GGTCCGGCTC AAGAAACAGG CCGCGACCGA CGTGCTGACC GGGCTGCTCA ACCGTGGCGG   3120
CTTCAATGCC AGCCTTGTCA CCGCACTCGA GAACGCCAAG CGACCGCACC CCGAGCCGCA   3180
GGCGCTGGTC ATGTTCGACC TTGACGGGTT CAAGCCGGTT AATGACATCC ATGGCCACCA   3240
TGCGGGCGAT GAGGTGCTCA AGGTAATCGG GCAGCGCCTG ATCGAGCTGA TCGGCCCCGA   3300
TGATGCGATC AGTCGGCTGG GTGGCGATGA GTTCGCCATC ATCCTGCGCC GCAGCCTCAA   3360
GCTCATGCCG CTCGAGACCA TCCTGACCAA GGTGCAGAAC CTGCTTGAAG AGCCGATCAT   3420
GCTGGACAGT GCCACGGTGC GCATATCGGG CAGCATCGGG GCCACGCCGA TCACGGGGGC   3480
CGACACGCTT GAGGGCCTGC AGAAAAACGC GGATGTGGCG GTCTACGCCG CCAAGCAGTC   3540
GGGCGGCAAA CAGGCGCGCA TGTTCACGCC GAGCCTGCAC AAGACCACGA TGGAGCGGGC   3600
CAAGATCCTG ACCGAGGCCC GCAAGGGCGT GGAGCTCAGG CAGTTCGAGG TTTACTACCA   3660
GCCCATACTG AACGCGCGCA CGGGCCGCAT CGAGCAGGCG GAAGCGCTGA TGCGCTGGCA   3720
CCACCCCGAT CGGGGCCTGC TCTCCGCTGG CGCATTTACC GATGTCTTTG CCGACTCGGC   3780
TCTGGCCCAG ATCATGGAGA CGCATCTTGT GCAGTCCTTC CATGACGATA TCCAGAAATG   3840
GAAGGAAGGG GGGCTGCCGA GCCTGCGGCT GGCGGTCAAC CTGTCGCATC TGGACCTGCT   3900
AAACCTTGAG CAGCAGATCG ACCTGTTCAG CGAGATCCGT GAACTCAACC TTGAACCCTC   3960
ACCATTCTGG AAGTAACCGA GCAGATTCTT CAGGGGCGGC GGGCGGAAAA AAACCGCCTT   4020
CGCCTGCGTT CGCTTTCGGG AAACGGGTTT GGCCTGGCCA TGGACAAATT TGGTTACGGC   4080
ACAGTGCGCC TTTCCACCCT GGGGGAACTG CCGTTCCAGT CGCTCAAGCT T            4131
```

( 2 ) INFORMATION FOR SEQ ID NO:4:

( i ) SEQUENCE CHARACTERISTICS:
        ( A ) LENGTH: 208 amino acids ( B ) TYPE: amino acid
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( A ) ORGANISM: Acetobacter xylinum ( x i ) SEQUENCE DESCRIPTION: SEQ ID NO:4:

| Met | Ser | Leu | Val | Gln | Pro | Ser | Leu | Ser | Ser | Asp | Gly | Thr | Lys | Arg | Thr |
|---|---|---|---|---|---|---|---|---|---|---|---|---|---|---|---|
| 1 | | | | 5 | | | | | 10 | | | | | 15 | |

| Phe | Ser | Glu | Arg | Gln | Glu | Phe | Met | Thr | Ala | Asp | Met | Pro | Ala | Ser | Met |
|---|---|---|---|---|---|---|---|---|---|---|---|---|---|---|---|
| | | | 20 | | | | 25 | | | | | 30 | | | |

| His | Phe | His | Val | Val | Ser | Gly | Gly | Ala | Arg | Leu | Phe | Lys | Ser | Leu | Pro |
|---|---|---|---|---|---|---|---|---|---|---|---|---|---|---|---|
| | | 35 | | | | | 40 | | | | | 45 | | | |

| Asp | Gly | Arg | Pro | Gln | Ile | Ile | Gly | Phe | Ala | His | Lys | Gly | Asp | Val | Leu |
|---|---|---|---|---|---|---|---|---|---|---|---|---|---|---|---|
| | 50 | | | | | 55 | | | | | 60 | | | | |

| Pro | Ala | Tyr | Pro | Cys | Thr | Arg | Tyr | His | Tyr | Ser | Ala | Glu | Ala | Met | Arg |
|---|---|---|---|---|---|---|---|---|---|---|---|---|---|---|---|
| 65 | | | | 70 | | | | | 75 | | | | | 80 | |

| Ser | Leu | Gln | Val | Val | Cys | Val | Pro | Ala | Pro | Tyr | Leu | Ser | His | Leu | His |
|---|---|---|---|---|---|---|---|---|---|---|---|---|---|---|---|
| | | | | 85 | | | | | 90 | | | | | 95 | |

| Glu | Thr | Ser | Pro | Gly | Ala | Cys | Ala | Ala | Ser | Leu | Asn | Ser | Ala | Arg | Gln |
|---|---|---|---|---|---|---|---|---|---|---|---|---|---|---|---|
| | | | 100 | | | | | 105 | | | | | 110 | | |

| Leu | Leu | Val | Ser | Leu | His | Ala | Arg | Leu | Leu | Met | Leu | Gly | Arg | Gln | Thr |
|---|---|---|---|---|---|---|---|---|---|---|---|---|---|---|---|
| | | | 115 | | | | | 120 | | | | | 125 | | |

| Ala | Arg | Glu | Arg | Leu | Ala | Thr | Phe | Leu | Leu | Gly | Gln | Gly | Thr | Arg | Met |
|---|---|---|---|---|---|---|---|---|---|---|---|---|---|---|---|
| | 130 | | | | | 135 | | | | | 140 | | | | |

| Gly | Pro | Gly | Glu | Leu | Trp | Pro | Val | Asp | Pro | Ser | Ile | Ser | Arg | Ala | Asp |
|---|---|---|---|---|---|---|---|---|---|---|---|---|---|---|---|
| 145 | | | | | 150 | | | | | 155 | | | | | 160 |

| Met | Ala | Asp | Phe | Leu | Gly | Leu | Thr | Thr | Glu | Thr | Val | Ser | Arg | Leu | Leu |
|---|---|---|---|---|---|---|---|---|---|---|---|---|---|---|---|
| | | | | 165 | | | | | 170 | | | | | 175 | |

| Ser | Ala | Phe | His | Arg | Glu | Gln | Leu | Ile | Cys | Arg | Glu | Arg | Arg | Ala | Ile |
|---|---|---|---|---|---|---|---|---|---|---|---|---|---|---|---|
| | | | 180 | | | | | 185 | | | | | 190 | | |

| His | Ile | Leu | Asp | Pro | Asp | Arg | Leu | Arg | Ala | Ile | Val | Ala | His | Pro | Glu |
|---|---|---|---|---|---|---|---|---|---|---|---|---|---|---|---|
| | | 195 | | | | | 200 | | | | | 205 | | | |

( 2 ) INFORMATION FOR SEQ ID NO:5:

( i ) SEQUENCE CHARACTERISTICS:
( A ) LENGTH: 765 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( A ) ORGANISM: Acetobater xylinum ( x i ) SEQUENCE DESCRIPTION: SEQ ID NO:5:

| Met | Pro | Asp | Ile | Thr | Ala | Leu | Thr | Thr | Glu | Ile | Leu | Leu | Pro | Ala | Leu |
|---|---|---|---|---|---|---|---|---|---|---|---|---|---|---|---|
| 1 | | | | 5 | | | | | 10 | | | | | 15 | |

| Glu | Gln | Ala | Ile | Asp | Ala | Thr | Val | Ile | Ile | Gly | Gln | Glu | Asn | Glu | Ile |
|---|---|---|---|---|---|---|---|---|---|---|---|---|---|---|---|
| | | | 20 | | | | | 25 | | | | | 30 | | |

| Ile | Phe | Tyr | Asn | Gln | Ala | Ala | Glu | Ser | Leu | Trp | Gly | Ile | Pro | Arg | Ala |
|---|---|---|---|---|---|---|---|---|---|---|---|---|---|---|---|
| | | 35 | | | | | 40 | | | | | 45 | | | |

```
Asp Val Ile Gly Arg Asn Val Asp Cys Leu Val Pro Thr Arg Leu Arg
    50              55                  60
His Glu His Asp Arg Tyr Ile Asp Arg Asn Glu Thr Gly His Asn
65          70                  75                      80
Arg Ile Val Gly Thr Ser Arg Glu Val Glu Phe Thr Arg Ala Asp Gly
                85                  90                  95
Glu Tyr Ile Cys Gly Glu Leu Ser Leu Ser Lys Val Gln Ile Gly Gln
            100                 105                 110
Gly Asp Lys Arg Leu Thr Tyr Tyr Met Gly Val Met Lys Asn Val Thr
        115                 120             125
Glu Glu Ser Gln Arg Arg Lys Ile Leu Ile Leu Gln Asn Asp Val Leu
130                     135                 140
Gln Ala Leu Ala Ser Asp Met Leu Ile Gln Asp Ile Gly Glu Leu Ile
145             150                 155                     160
Cys Arg Lys Val Glu Ala Phe Val Pro Asn Ser Val Ala Ala Leu Leu
                165             170             175
Val Leu Asp Asp Ala Gln Pro Trp Arg Val Ile Cys Thr Ser Ala Leu
            180             185                 190
Pro Pro Arg Ile Arg Asn Ala Leu Glu Thr Thr Val Pro Ser Pro Ser
        195             200                 205
Asp Val Glu Lys Leu Lys Ala Asn Ala Ser Tyr Thr Gly His Leu Val
210             215                 220
Trp Asn Asn Tyr Gln Ser Met Cys Arg Ser Leu Gly Leu Gln Ser Cys
225             230                 235                     240
Tyr Ala Ala Pro Val Met Ala Gly Asp Gly Arg Val Thr Gly Ile Phe
                245                 250                 255
Ala Leu Tyr Leu Arg Glu Pro Asn Gln Leu Gly Ala Trp Pro Gln Arg
            260             265                 270
Leu Val Gly Ala Cys Leu Pro Phe Cys Ala Leu Ala Leu Glu Gln His
        275             280                 285
Ala Thr Lys Thr His Leu Thr Gln Leu Ala Arg Tyr Asp Ser Leu Thr
290                 295                 300
Gly Leu Leu Asn Arg Gly Ala Leu His Arg Val Met Glu Asp Ile Ile
305             310                 315                     320
Ala Gln Pro Gly Asn Arg Thr Leu Ala Ile Phe Met Leu Asp Ile Asp
                325                 330                 335
Arg Phe Arg Asp Ile Asn Asp Ala Leu Gly His Val Tyr Ala Asp Gln
            340             345                 350
Phe Leu Val Glu Ile Ala Gly Arg Ile Arg Ser Ile Ala Lys Asp Asp
        355             360             365
Tyr Val Leu Ser Arg Ser Gly Gly Asp Glu Phe Val Val Val Pro
370                 375                 380
Asp Cys Glu Gly Lys Gln Ile Glu Glu Ile Ala His Lys Leu Leu Glu
385             390                 395                     400
Thr Ile Gly Arg Pro Leu Gln Ile Gly Gln Asn Thr Leu Ser Ile Ser
                405                 410                 415
Cys Ser Ile Gly Ile Ser Thr Phe Pro Ala Asn Gly Pro Asp Ser Glu
            420             425                 430
Ser Leu Leu Ser His Ala Asp Thr Ala Met Arg Gln Ala Lys Glu Asp
        435                 440                 445
Gly Arg Gly Ile Phe Arg Phe Ala Asn Leu Glu Lys Asn Gln Val Ala
    450                 455                 460
Gln Asp Arg Leu Val Leu Gly Ser Ala Leu Arg Asp Ser Leu Ala Gln
```

|       |       |       | 465   |       |       |       | 470   |       |       |       | 475   |       |       |       | 480   |
|-------|-------|-------|-------|-------|-------|-------|-------|-------|-------|-------|-------|-------|-------|-------|-------|
| Gly   | Met   | Leu   | Gln   | Leu   | His   | Tyr   | Gln   | Pro   | Gln   | Val   | Arg   | Thr   | His   | Thr   | Leu   |
|       |       |       |       | 485   |       |       |       |       | 490   |       |       |       |       | 495   |       |
| Glu   | Leu   | Ser   | Gly   | Val   | Glu   | Ala   | Leu   | Ser   | Arg   | Trp   | His   | His   | Pro   | His   | Leu   |
|       |       |       | 500   |       |       |       |       | 505   |       |       |       |       | 510   |       |       |
| Gly   | Asn   | Ile   | Phe   | Pro   | Ser   | Arg   | Phe   | Ile   | Ala   | Val   | Ala   | Glu   | Glu   | Thr   | Gly   |
|       |       |       | 515   |       |       |       |       | 520   |       |       |       |       | 525   |       |       |
| Gln   | Ile   | Glu   | Ala   | Ile   | Gly   | Arg   | Trp   | Ser   | Leu   | Leu   | Glu   | Ala   | Cys   | Arg   | Gln   |
|       |       |       | 530   |       |       |       |       | 535   |       |       |       |       | 540   |       |       |
| Ile   | Val   | Lys   | Trp   | Asp   | Arg   | Asp   | Gly   | Ile   | His   | Val   | Pro   | Thr   | Val   | Ala   | Val   |
| 545   |       |       |       |       |       | 550   |       |       |       |       | 555   |       |       |       | 560   |
| Asn   | Leu   | Ser   | Ala   | Val   | His   | Phe   | Arg   | Asn   | Arg   | Ala   | Leu   | Pro   | Glu   | His   | Ile   |
|       |       |       |       | 565   |       |       |       |       | 570   |       |       |       |       | 575   |       |
| Ala   | Ala   | Leu   | Leu   | Lys   | Asp   | His   | Asn   | Leu   | Lys   | Pro   | Ser   | Arg   | Leu   | Thr   | Val   |
|       |       |       | 580   |       |       |       |       | 585   |       |       |       |       | 590   |       |       |
| Glu   | Ile   | Thr   | Glu   | Ser   | Val   | Met   | Met   | Asp   | Asn   | Ser   | Arg   | Asp   | Thr   | Glu   | Glu   |
|       |       |       | 595   |       |       |       |       | 600   |       |       |       |       | 605   |       |       |
| Val   | Leu   | Gln   | Ser   | Ile   | Arg   | Asn   | Ile   | Gly   | Cys   | Gly   | Leu   | Ser   | Met   | Asp   | Asp   |
|       |       |       | 610   |       |       |       |       | 615   |       |       |       |       | 620   |       |       |
| Phe   | Gly   | Thr   | Gly   | Tyr   | Ser   | Ser   | Leu   | Ser   | Arg   | Leu   | Thr   | Arg   | Leu   | Pro   | Leu   |
| 625   |       |       |       |       |       | 630   |       |       |       |       | 635   |       |       |       | 640   |
| Thr   | Glu   | Ile   | Lys   | Ile   | Asp   | Arg   | Ser   | Phe   | Ile   | Asn   | Asp   | Phe   | Glu   | Tyr   | Asp   |
|       |       |       |       | 645   |       |       |       |       | 650   |       |       |       |       | 655   |       |
| Thr   | Asn   | Ala   | Gln   | Ala   | Val   | Thr   | Met   | Ala   | Val   | Ile   | Gly   | Ile   | Gly   | Ser   | Arg   |
|       |       |       | 660   |       |       |       |       | 665   |       |       |       |       | 670   |       |       |
| Leu   | Gly   | Met   | Thr   | Val   | Val   | Thr   | Glu   | Gly   | Val   | Glu   | Thr   | Glu   | Gln   | Gln   | Arg   |
|       |       |       | 675   |       |       |       |       | 680   |       |       |       |       | 685   |       |       |
| Asp   | Leu   | Leu   | Glu   | Lys   | Leu   | Asn   | Cys   | Asp   | Val   | Met   | Gln   | Gly   | Leu   | Tyr   | Phe   |
|       |       |       | 690   |       |       |       |       | 695   |       |       |       |       | 700   |       |       |
| Ala   | Lys   | Pro   | Leu   | Ala   | Pro   | Gln   | Asp   | Leu   | Glu   | Ser   | Trp   | Val   | Arg   | Arg   | Gly   |
| 705   |       |       |       |       |       | 710   |       |       |       |       | 715   |       |       |       | 720   |
| Gly   | Ala   | Pro   | Ala   | Val   | Ile   | Arg   | Glu   | Ile   | Glu   | Ala   | Ala   | Arg   | Ala   | Lys   | Lys   |
|       |       |       |       | 725   |       |       |       |       | 730   |       |       |       |       | 735   |       |
| Gly   | Gly   | Lys   | Pro   | Glu   | Ser   | Ser   | Gly   | Lys   | Lys   | Asp   | Gly   | Ala   | Pro   | Ala   | Ala   |
|       |       |       | 740   |       |       |       |       | 745   |       |       |       |       | 750   |       |       |
| Lys   | Pro   | Ala   | Ala   | Ala   | Ser   | Pro   | Ala   | Thr   | Pro   | Glu   | Lys   | Ser   |       |       |       |
|       |       |       | 755   |       |       |       |       | 760   |       |       |       |       | 765   |       |       |

( 2 ) INFORMATION FOR SEQ ID NO:6:

( i ) SEQUENCE CHARACTERISTICS:
        ( A ) LENGTH: 580 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Acteobater xylinum ( x i ) SEQUENCE DESCRIPTION: SEQ ID NO:6:

|  Met  |  Ser  |  Leu  |  Lys  |  His  |  Asp  |  Asp  |  Arg  |  Leu  |  Arg  |  Ala  |  Leu  |  Thr  |  His  |  Gln  |  Asp  |
|-------|-------|-------|-------|-------|-------|-------|-------|-------|-------|-------|-------|-------|-------|-------|-------|
|  1    |       |       |       |  5    |       |       |       |       |  10   |       |       |       |       |  15   |       |
|  Ser  |  Asp  |  Phe  |  Trp  |  Ala  |  Asp  |  Val  |  Val  |  Asp  |  Asn  |  Val  |  Leu  |  Ile  |  Val  |  Ala  |  Ile  |
|       |       |       |  20   |       |       |       |       |  25   |       |       |       |       |  30   |       |       |

```
Thr  Asp  Val  Arg  Gly  Val  Ile  Thr  Tyr  Val  Asn  Asp  Arg  Phe  Cys  Glu
          35                       40                 45
Ile  Ser  Arg  Tyr  Pro  Arg  Glu  Glu  Leu  Leu  Gly  Ala  Thr  His  Arg  Ile
     50                       55                      60
Val  Asn  Ser  Gly  Tyr  His  Asp  Ala  Ser  Phe  Phe  Arg  Gln  Met  Tyr  Arg
65                       70                  75                            80
Thr  Ile  Arg  Gly  Gly  Glu  Ile  Trp  Arg  Gly  Asn  Ile  Cys  Asn  Arg  Ala
               85                      90                       95
Lys  Asp  Gly  Thr  Leu  Tyr  Trp  Val  Ala  Thr  Thr  Ile  Met  Pro  Lys  His
               100                      105                 110
Asn  Ser  Leu  Gly  Ala  Val  Glu  Gly  Tyr  Val  Ala  Thr  Arg  Phe  Glu  Ile
          115                      120                      125
Thr  Glu  Leu  Met  Asn  Thr  Arg  Asp  Arg  Leu  Lys  Ser  Leu  Ala  Ala  Thr
     130                      135                 140
Asp  Pro  Leu  Thr  Gly  Leu  Phe  Asn  Arg  Gly  Gly  Phe  Asn  Asn  Val  Leu
145                      150                 155                           160
Gln  Thr  Ala  Val  Glu  Asp  Lys  Ser  Gln  Asn  Ile  Thr  Arg  Asp  Ile  Met
               165                      170                           175
Leu  Val  Met  Phe  Asp  Leu  Asp  Gly  Phe  Lys  Gln  Ile  Asn  Asp  Ile  His
               180                      185                 190
Gly  His  His  Ala  Gly  Asp  Val  Val  Leu  Lys  Val  Ile  Ser  Asn  Arg  Leu
          195                      200                 205
Leu  Ala  Leu  Val  His  Pro  Glu  Asp  Ala  Val  Cys  Arg  Leu  Gly  Gly  Asp
     210                      215                 220
Glu  Phe  Ala  Leu  Ile  Leu  Asn  His  Thr  Leu  His  Lys  Phe  Ala  Leu  Ser
225                      230                 235                           240
Leu  Met  Leu  Glu  Lys  Leu  Leu  Ala  Glu  Leu  Glu  Ala  Pro  Ile  Glu  Val
               245                      250                      255
Gly  Asn  Thr  Met  Val  Asn  Val  Ser  Gly  Ser  Ile  Gly  Val  Thr  Pro  Ile
               260                      265                 270
Ala  Ser  Gln  Glu  Ser  Ala  Glu  Ser  Leu  Gln  Lys  Asn  Ala  Asp  Ile  Ala
          275                      280                 285
Leu  Tyr  Ala  Ala  Lys  Arg  Ala  Gly  Gly  His  Gln  Ala  Arg  Met  Phe  Asp
     290                      295                 300
Met  Thr  Leu  His  Gln  His  Ala  Leu  Glu  Arg  Ala  Gln  Ile  Leu  Asn  Asp
305                      310                 315                           320
Ala  Arg  Glu  Gly  Val  Met  Lys  Asp  Gln  Phe  Glu  Leu  Tyr  Tyr  Gln  Pro
               325                      330                      335
Ile  Met  Asn  Phe  Ser  Thr  Gly  Lys  Cys  Asp  Gln  Ile  Glu  Ala  Leu  Leu
               340                      345                 350
Pro  Trp  His  His  Pro  Gln  Arg  Gly  Leu  Leu  Ala  Ala  Glu  Ser  Phe  Arg
          355                      360                 365
Asp  Val  Phe  Leu  Asp  Ala  Ala  Leu  Ala  Gln  Val  Met  Ser  Pro  Arg  Leu
     370                      375                 380
Val  Lys  Ser  Phe  Gln  Asn  Asp  Met  Arg  Met  Trp  Asn  Thr  Ser  Leu  Asp
385                      390                 395                           400
Ala  Tyr  Pro  Asn  Leu  Thr  Ile  Asn  Leu  Ser  Arg  Leu  Gly  Leu  Leu  Asn
               405                      410                      415
Ile  Gly  Phe  Gln  Asn  Asp  Leu  Glu  Ala  Ile  Lys  Arg  Gln  Gly  Gly
               420                      425                 430
Lys  Ala  Ala  Asp  Tyr  Val  Leu  Glu  Ile  Ser  Glu  Ser  Val  Leu  Ala  Gly
          435                      440                 445
Arg  Arg  Ser  Asp  Arg  Val  Leu  Gln  Arg  Leu  Gln  Glu  Leu  Ser  Glu  Leu
```

|   |   |   |   |   |   |   |   |   |   |   |   |   |   |   |
|---|---|---|---|---|---|---|---|---|---|---|---|---|---|---|
|   |   |   |   | 450 |   |   |   |   | 455 |   |   |   | 460 |   |

| Gly | Phe | Gln | Leu | Thr | Leu | Asp | Asp | Phe | Gly | Leu | Ala | Thr | Leu | Pro | Ile |
| 465 |     |     |     |     | 470 |     |     |     | 475 |     |     |     |     |     | 480 |
| Ser | Val | Leu | Arg | Thr | Ile | Ser | Phe | Thr | Gln | Ala | Lys | Ile | Ser | Arg | Lys |
|     |     |     |     | 485 |     |     |     |     | 490 |     |     |     |     | 495 |     |
| Leu | Val | Lys | Asp | Ile | Glu | Thr | Ser | Pro | Gln | Ala | Arg | Gly | Val | Val | Ala |
|     |     |     | 500 |     |     |     |     | 505 |     |     |     |     | 510 |     |     |
| His | Leu | Ile | Gly | Leu | Ala | His | Ala | Phe | Gly | Leu | Ser | Val | Thr | Val | Ser |
|     |     |     | 515 |     |     |     | 520 |     |     |     |     | 525 |     |     |     |
| Gly | Val | Glu | Thr | Lys | Gly | Gln | Met | Glu | Val | Leu | Arg | Glu | Met | Gly | Ala |
|     |     | 530 |     |     |     | 535 |     |     |     |     | 540 |     |     |     |     |
| Asp | Arg | Ile | Gln | Gly | Phe | Tyr | Ile | Ser | Pro | Pro | Ile | Ser | Ala | Ala | Asn |
| 545 |     |     |     |     | 550 |     |     |     |     | 555 |     |     |     |     | 560 |
| Leu | Val | Leu | Ala | Glu | His | Ile | Ile | Ala | Pro | Asp | His | Thr | Glu | Ile | Thr |
|     |     |     |     | 565 |     |     |     |     | 570 |     |     |     |     | 575 |     |
| Leu | Gln | Ala | Ser |     |     |     |     |     |     |     |     |     |     |     |     |
|     |     |     | 580 |     |     |     |     |     |     |     |     |     |     |     |     |

( 2 ) INFORMATION FOR SEQ ID NO:7:

( i ) SEQUENCE CHARACTERISTICS:
        ( A ) LENGTH: 138 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Acetobacter xylinum ( x i ) SEQUENCE DESCRIPTION: SEQ ID NO:7:

| Met | Arg | Leu | Thr | Leu | Tyr | Thr | Asp | Tyr | Ser | Ile | Arg | Thr | Leu | Ile | Tyr |
| 1   |     |     |     | 5   |     |     |     |     | 10  |     |     |     |     | 15  |     |
| Leu | Gly | Gln | Asn | Pro | Gly | Arg | Arg | Val | Ala | Ile | Gln | Glu | Ile | Ala | Ala |
|     |     |     | 20  |     |     |     |     | 25  |     |     |     |     | 30  |     |     |
| Thr | His | Arg | Ile | Ser | Gln | Asn | His | Leu | Val | Lys | Val | Val | Asn | Arg | Leu |
|     |     | 35  |     |     |     |     | 40  |     |     |     |     | 45  |     |     |     |
| Ser | Ser | Asn | Gly | Val | Ile | Leu | Ala | Arg | Arg | Gly | Arg | Ser | Gly | Gly | Leu |
|     | 50  |     |     |     |     | 55  |     |     |     |     | 60  |     |     |     |     |
| Glu | Leu | Ala | Gly | Ala | Pro | His | Gln | Ile | Ile | Ile | Gly | Asp | Ile | Ile | His |
| 65  |     |     |     |     | 70  |     |     |     |     | 75  |     |     |     |     | 80  |
| Leu | Met | Glu | Ala | Asp | Met | Gly | Lys | Ile | Val | Ser | Cys | Asn | Pro | Glu | Asn |
|     |     |     |     | 85  |     |     |     |     | 90  |     |     |     |     | 95  |     |
| Gly | Gln | Ala | Cys | Val | Leu | Ala | Asp | Ala | Cys | Arg | Leu | Gln | Gly | Leu | Phe |
|     |     |     | 100 |     |     |     |     | 105 |     |     |     |     | 110 |     |     |
| Ala | Lys | Ser | Val | Asn | Ala | Phe | Met | Ser | Val | Leu | Asp | Arg | Ile | Thr | Leu |
|     |     | 115 |     |     |     |     | 120 |     |     |     |     | 125 |     |     |     |
| His | Asp | Ile | Leu | His | Glu | Pro | Lys | Lys | Leu |     |     |     |     |     |     |
|     | 130 |     |     |     |     | 135 |     |     |     |     |     |     |     |     |     |

( 2 ) INFORMATION FOR SEQ ID NO:8:

( i ) SEQUENCE CHARACTERISTICS:
        ( A ) LENGTH: 752 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) ORIGINAL SOURCE:
   ( A ) ORGANISM: Acetobater xylinum ( x i ) SEQUENCE DESCRIPTION: SEQ ID NO:8:

| Met | Pro | Ala | Gln | Val | Arg | Lys | Met | Ile | Leu | His | Gly | Ala | Val | Gly | Arg |
|---|---|---|---|---|---|---|---|---|---|---|---|---|---|---|---|
| 1 | | | | 5 | | | | | 10 | | | | | 15 | |
| Ala | Asp | Val | Leu | Glu | Phe | Thr | Val | Asp | Gln | Pro | Lys | Ile | Ser | Ala | Asp |
| | | | 20 | | | | 25 | | | | | 30 | | | |
| Val | Leu | Leu | Ser | Ala | Met | Glu | Gln | Ala | Ile | Asp | Pro | Met | Val | Val | Ile |
| | | 35 | | | | 40 | | | | | 45 | | | | |
| Asp | Glu | His | Asn | Leu | Ile | Ile | Phe | Phe | Asn | Ala | Ala | Ala | Glu | Lys | Ile |
| | 50 | | | | | 55 | | | | | 60 | | | | |
| Trp | Gly | Cys | Ser | Arg | Glu | Glu | Val | Met | Gly | Arg | Asn | Val | Ser | Cys | Leu |
| 65 | | | | | 70 | | | | | 75 | | | | | 80 |
| Val | Pro | Glu | Pro | Glu | Arg | Asp | Arg | His | Asp | Asp | Tyr | Ile | Asn | Arg | Asn |
| | | | | 85 | | | | 90 | | | | | | 95 | |
| Arg | Glu | Thr | Gly | Val | Gly | Arg | Ile | Val | Gly | Thr | Ser | Arg | Glu | Val | Glu |
| | | | 100 | | | | | 105 | | | | | 110 | | |
| Phe | Arg | Arg | Ala | Asn | Gly | Glu | Tyr | Val | Cys | Gly | Glu | Leu | Ser | Ile | Ser |
| | | 115 | | | | | 120 | | | | | 125 | | | |
| Arg | Val | Gln | Val | Asn | Asp | Cys | Gly | Lys | Ile | Tyr | Tyr | Ile | Ala | Val | Met |
| | 130 | | | | | 135 | | | | | 140 | | | | |
| Lys | Asp | Val | Thr | Glu | Gln | Ser | Arg | Gln | Arg | Lys | Ile | Leu | Val | Leu | Gln |
| 145 | | | | | 150 | | | | | 155 | | | | | 160 |
| Asn | Asp | Val | Leu | Gln | Ala | Leu | Ala | Ser | Asp | Met | Ser | Ile | Gln | Glu | Val |
| | | | | 165 | | | | | 170 | | | | | 175 | |
| Gly | Asp | Leu | Leu | Cys | Arg | Arg | Ala | Asp | Ser | Phe | Val | Pro | Gly | Ala | Val |
| | | | 180 | | | | | 185 | | | | | 190 | | |
| Gly | Ala | Leu | Met | Leu | Ile | Asp | Arg | Ser | Arg | Arg | Leu | Ser | Val | Ser | Ala |
| | | 195 | | | | | 200 | | | | | 205 | | | |
| Ser | Pro | Ser | Met | Pro | Lys | Arg | Tyr | Arg | Ala | Ala | Leu | Asp | Ser | Met | Gln |
| | 210 | | | | | 215 | | | | | 220 | | | | |
| Leu | Thr | Pro | Glu | Gln | Leu | Glu | Met | Leu | Arg | Ala | Asn | Pro | Ala | Gly | Ser |
| 225 | | | | | 230 | | | | | 235 | | | | | 240 |
| Asn | Thr | Val | Val | Trp | Asp | Gly | Tyr | Ala | Ser | Leu | Ala | Arg | Ser | Leu | Gly |
| | | | | 245 | | | | | 250 | | | | | 255 | |
| Leu | Glu | Arg | Cys | Cys | Ser | Ser | Thr | Ile | Ile | Ser | Arg | Thr | Gly | Gln | Val |
| | | | 260 | | | | | 265 | | | | | 270 | | |
| Met | Gly | Val | Phe | Ala | Leu | Tyr | Leu | Arg | Gly | Asp | Glu | Ala | Asp | Leu | Ala |
| | | 275 | | | | | 280 | | | | | 285 | | | |
| Trp | Ala | Gln | Arg | Val | Val | Ser | Thr | Ser | Met | Pro | Phe | Cys | Ala | Leu | Ala |
| | 290 | | | | | 295 | | | | | 300 | | | | |
| Ile | Glu | Gln | Ser | Glu | Thr | Arg | Gln | His | Ile | Ala | Gln | Leu | Ser | Asn | Phe |
| 305 | | | | | 310 | | | | | 315 | | | | | 320 |
| Asp | Ser | Leu | Thr | Gly | Leu | Leu | Asn | Arg | Thr | Ser | Leu | His | Asn | Ile | Ile |
| | | | | 325 | | | | | 330 | | | | | 335 | |
| Glu | Arg | Leu | Ile | Met | Arg | Gly | Gly | Asp | Ser | Gln | Phe | Ser | Leu | Phe | Met |
| | | | 340 | | | | | 345 | | | | | 350 | | |
| Val | Asp | Ile | Asp | Arg | Phe | Arg | Asp | Ile | Asn | Asp | Ala | Leu | Gly | His | Val |
| | | 355 | | | | | 360 | | | | | 365 | | | |

-continued

```
Asn  Ala  Asp  Arg  Phe  Leu  Ile  Glu  Ile  Gly  Arg  Arg  Ile  Arg  His  Leu
     370                 375                     380

Val  Lys  Asp  Asp  Tyr  Ile  Val  Ser  Arg  Ser  Gly  Gly  Asp  Glu  Phe  Ile
385                      390                     395                         400

Ile  Val  Val  Pro  Glu  Cys  Ser  His  Glu  Arg  Ala  Glu  Lys  Phe  Ala  Glu
               405                      410                     415

Asn  Leu  Ile  Asn  Ala  Ile  Ala  Arg  Pro  Leu  Gln  Val  Gly  Glu  Asn  Thr
          420                      425                     430

Leu  Ser  Ile  Ser  Cys  Cys  Val  Gly  Ile  Ser  Thr  Phe  Pro  Ala  Asn  Gly
          435                 440                          445

Pro  Asp  Ser  Glu  Ser  Leu  Leu  Ser  His  Ala  Asp  Ala  Ala  Thr  Arg  Gln
     450                      455                     460

Ala  Lys  Glu  Asp  Gly  Arg  Gly  Leu  Phe  Arg  Phe  Ala  Gly  Gln  Glu  Lys
465                      470                     475                         480

Asn  Gln  Val  Ala  Gln  Asp  Arg  Leu  Val  Leu  Gly  Ser  Ala  Leu  Arg  Asp
               485                      490                     495

Ser  Leu  Ser  Lys  Gly  Met  Leu  Asn  Leu  Asn  Tyr  Gln  Pro  Gln  Val  Glu
          500                      505                     510

Thr  Met  Thr  Gly  Gly  Leu  Tyr  Gly  Val  Glu  Ala  Leu  Ser  Arg  Trp  His
          515                      520                     525

His  Pro  Thr  Leu  Gly  Asn  Ile  Tyr  Pro  Ser  Arg  Phe  Ile  Ala  Val  Ala
     530                      535                     540

Glu  Glu  Thr  Gly  Gln  Ile  Glu  Ala  Ile  Gly  Arg  Trp  Ser  Leu  Glu  Glu
545                      550                     555                         560

Ala  Cys  Ser  Gln  Met  Val  Lys  Trp  Asp  Arg  Asp  Gly  Val  Arg  Val  Pro
               565                      570                     575

Thr  Val  Ala  Val  Asn  Leu  Ser  Ala  Val  His  Phe  Arg  Asn  Arg  Gly  Leu
               580                      585                     590

Pro  Glu  His  Ile  Ala  Asn  Leu  Leu  Lys  His  His  Gly  Leu  Thr  Pro  Asp
          595                      600                     605

Arg  Leu  Thr  Val  Glu  Ile  Thr  Glu  Ser  Val  Met  Met  Asp  Ser  Ser  Ser
     610                      615                     620

Glu  Thr  Glu  Glu  Val  Leu  His  Ala  Ile  Arg  Arg  Leu  Asp  Val  Gly  Leu
625                      630                     635                         640

Ser  Met  Asp  Asp  Phe  Gly  Thr  Gly  Tyr  Ser  Ser  Leu  Ser  Arg  Leu  Thr
               645                      650                     655

Arg  Leu  Pro  Leu  Thr  Glu  Ile  Lys  Ile  Asp  Arg  Ser  Phe  Ile  Asn  Asp
               660                      665                     670

Phe  Glu  His  Asp  Thr  Asn  Ala  Gln  Ala  Val  Thr  Met  Ala  Val  Ile  Gly
          675                      680                     685

Ile  Gly  Ser  Arg  Leu  Gly  Met  Thr  Val  Val  Thr  Glu  Gly  Val  Glu  Thr
     690                      695                     700

Glu  Gln  Gln  Trp  Arg  Leu  Leu  Glu  Glu  Leu  His  Cys  Asp  Val  Met  Gln
705                      710                     715                         720

Gly  Tyr  Leu  Phe  Ser  Lys  Pro  Leu  Pro  Pro  Ala  Glu  Leu  Glu  Lys  Trp
               725                      730                     735

Phe  Arg  Glu  Arg  Gln  Glu  Arg  Gly  Ser  Phe  Leu  Ile  Pro  Thr  Thr  Ala
               740                      745                     750
```

( 2 ) INFORMATION FOR SEQ ID NO:9:

( i ) SEQUENCE CHARACTERISTICS:
( A ) LENGTH: 574 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Acetobacter xylinum ( x i ) SEQUENCE DESCRIPTION: SEQ ID NO:9:

```
Met Ala Leu Gln His Asp Asp Arg Leu Arg Ala Leu Thr His Gln Asp
 1               5                  10                  15

Ala Asp Phe Trp Ala Asp Leu Val Asp Asn Val Leu Ile Val Ala Ile
            20                  25                  30

Thr Asp Ser Glu Gly Val Ile Thr Tyr Val Asn Asp Arg Phe Cys Glu
        35                  40                  45

Ile Ser Gln Tyr Ser Arg Glu Leu Val Gly Ser Thr His Arg Ile
    50                  55                  60

Val Asn Ser Gly Tyr His Asp Ala Asp Phe Phe Arg Asp Leu Tyr Arg
65                  70                  75                  80

Thr Ile Lys Ala Gly Gln Leu Trp Arg Gly Asn Ile Cys Asn Arg Ala
                85                  90                  95

Lys Asp Gly Ser Leu Tyr Trp Val Ala Thr Thr Ile Ile Pro Lys Ile
            100                 105                 110

Asp Arg Gln Gly Thr Ile Thr Gly Tyr Val Ala Ser Arg Phe Glu Leu
        115                 120                 125

Thr Glu Leu Met Asn Thr Arg Asp Arg Leu Cys Glu Leu Ala Glu Thr
    130                 135                 140

Asp Thr Leu Thr Gly Leu Leu Asn Arg Gly Gly Phe Asn Thr Ala Leu
145                 150                 155                 160

Ala Asp Glu Ile Ala Arg Cys Arg Glu Pro Gly Met Thr Ala His Pro
                165                 170                 175

Ala Leu Ala Met Phe Asp Leu Asp Gly Phe Lys Gln Ile Asn Asp Val
            180                 185                 190

His Gly His His Ala Gly Asp Ile Val Leu Arg Ala Ile Ala Ser Arg
        195                 200                 205

Leu Ile Glu Leu Thr His Pro Asp Asp Pro Val Ser Arg Leu Gly Gly
    210                 215                 220

Asp Glu Phe Ala Val Ile Leu His Arg Thr Leu Glu Asp Val Ser Leu
225                 230                 235                 240

Glu Arg Tyr Met Asp Arg Leu Gln Ala Ile Leu Glu Arg Pro Ile Asp
                245                 250                 255

Ile Glu Thr Val Thr Val Ser Val Ala Gly Ser Ile Gly Ala Val Leu
            260                 265                 270

Leu Asp Gly Thr Asp Thr Met Glu Asp Val Gln Lys Asn Ala Asp Met
        275                 280                 285

Ala Met Tyr Ala Ala Lys Ala Gly Gly Lys Gln Ser Gln Met Phe
    290                 295                 300

Thr Arg Asn Leu Arg Glu Arg Ala Gln Ala Arg Val Ser Ile Leu Ser
305                 310                 315                 320

Glu Ala Arg Cys Gly Val Glu Arg Asn Gln Phe Glu Val Tyr Tyr Gln
                325                 330                 335

Pro Ile Val Asn Cys Asn Thr Met Glu Val Asp Gln Ile Glu Ala Leu
            340                 345                 350

Leu Arg Trp Gln His Pro Glu Arg Gly Leu Leu Ala Ala Glu Asp Phe
        355                 360                 365
```

```
Ser  Asp  Val  Phe  Thr  Asp  Ala  Gly  Leu  Ala  Gln  Ala  Met  Gly  Pro  Arg
     370                 375                      380

Met  Ile  Glu  Ala  Phe  Arg  Arg  Asp  Val  Cys  Met  Trp  Asn  Glu  Lys  Gly
385                      390                      395                      400

Gln  Pro  Pro  Arg  Gln  Leu  Ala  Ile  Asn  Leu  Ser  Arg  Met  Asp  Leu  Ile
                    405                 410                      415

Arg  Asp  Asp  Tyr  Gln  Arg  Glu  Leu  Glu  Ser  Leu  Arg  Arg  Phe  Asn
               420                 425                      430

Met  Ser  Pro  Asp  Ser  Phe  Val  Leu  Glu  Val  Thr  Glu  Ala  Met  Leu  His
          435                      440                      445

Gly  Arg  Arg  Glu  Glu  Gln  Gly  Ile  Arg  Asn  Leu  Arg  Glu  Leu  Ala  Arg
     450                      455                      460

Ala  Gly  Phe  Arg  Ile  Ala  Leu  Asp  Asn  Phe  Gly  Lys  Gly  Ile  Thr  Val
465                      470                      475                      480

Leu  Asn  His  Leu  Arg  Glu  Leu  Pro  Phe  Ser  Gln  Val  Lys  Ile  Asp  Gln
               485                      490                      495

Ser  Met  Val  Thr  Asn  Ile  Val  Gly  Asn  Pro  Asp  Ala  Cys  Met  Val  Leu
               500                 505                      510

Ser  Ser  Leu  Ile  Asp  Met  Gly  Gln  Gly  Phe  Asn  Met  Glu  Val  Thr  Val
          515                      520                      525

Glu  Gly  Val  Glu  Asn  Arg  Glu  Gln  Phe  Glu  Leu  Val  Lys  Ala  Leu  Arg
     530                      535                      540

Pro  Glu  Arg  Ile  Gln  Gly  Phe  Phe  Val  Ser  Ser  Ala  Leu  Ser  Ser  Gln
545                      550                      555                      560

Asp  Ile  Leu  Lys  Leu  Pro  Ala  Arg  Phe  Glu  Gly  Val  Thr  Leu
                    565                      570
```

(2) INFORMATION FOR SEQ ID NO:10:

(i) SEQUENCE CHARACTERISTICS:
        (A) LENGTH: 740 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Acetobacter xylinum (xi) SEQUENCE DESCRIPTION: SEQ ID NO:10:

```
Met  Ser  Lys  Pro  Asn  Leu  Ser  Ala  Glu  Val  Leu  Ile  Ser  Ala  Leu  Glu
1                   5                   10                      15

Gln  Ala  Ile  Asp  Ala  Thr  Val  Ile  Ile  Asp  Asp  Lys  Asn  Glu  Val  Ile
               20                       25                      30

Phe  Phe  Asn  Gln  Ala  Gly  Ser  Asn  Leu  Trp  Gly  Leu  Asp  Lys  Lys  Asp
          35                       40                      45

Val  Leu  Gly  Lys  Asn  Val  Asn  Val  Leu  Val  Pro  Thr  Leu  His  Gln  Ala
     50                       55                      60

Gly  His  Asp  Ala  Phe  Val  Glu  Arg  Ser  Arg  Gly  Ser  Ser  His  Asn  Arg
65                       70                      75                      80

Ile  Val  Gly  Thr  Ser  Arg  Glu  Val  Glu  Phe  Thr  Arg  Ser  Asp  Gly  Glu
                    85                      90                      95

Tyr  Ile  Cys  Gly  Glu  Leu  Ser  Leu  Ser  Lys  Val  Val  Asn  Asp  Asp  Lys
               100                      105                     110

Arg  Ile  Phe  Phe  Met  Gly  Val  Met  Lys  Asn  Val  Thr  Asn  Glu  Ser  Gln
```

|  |  |  | 115 |  |  |  | 120 |  |  |  | 125 |  |  |
|---|---|---|---|---|---|---|---|---|---|---|---|---|---|
| Gln | Arg | Lys | Ile | Leu | Ile | Leu | Gln | Asn | Asp | Val | Leu | Gln | Ala | Leu | Ala |
| 130 | | | | | 135 | | | | | 140 | | | |
| Ser | Asp | Met | Met | Ile | Gln | Asp | Val | Ala | Asp | Leu | Leu | Cys | Arg | Arg | Val |
| 145 | | | | | 150 | | | | | 155 | | | | | 160 |
| Glu | Ser | Phe | Val | Pro | Gly | Thr | Val | Ala | Val | Leu | Met | Leu | Ile | Thr | Pro |
| | | | | 165 | | | | | 170 | | | | | 175 | |
| Asp | Gly | Gln | Leu | Arg | Val | Leu | Ser | Ser | Pro | Thr | Leu | Pro | Lys | Arg | Tyr |
| | | | 180 | | | | | 185 | | | | | 190 | |
| Arg | Ala | Ser | Leu | Glu | Ser | Leu | Tyr | Val | Ser | Ser | Glu | Leu | Glu | Lys |
| | | 195 | | | | | 200 | | | | | 205 | | |
| Leu | Arg | Val | Asp | Pro | Lys | His | Ala | Thr | Arg | Met | Val | Trp | Asp | Ser | Tyr |
| | 210 | | | | | 215 | | | | | 220 | | | | |
| Arg | Ser | Leu | Gly | Ile | Ser | Leu | Gly | Leu | Gln | Gln | Cys | Phe | Cys | Thr | Pro |
| 225 | | | | | 230 | | | | | 235 | | | | | 240 |
| Val | Ser | Thr | Arg | Ser | Gly | Gln | Val | Lys | Gly | Ile | Phe | Ala | Leu | Tyr | Ser |
| | | | | 245 | | | | | 250 | | | | | 255 | |
| Arg | Glu | Asp | Gln | Gly | Arg | Asn | Thr | Gln | Pro | Gln | Arg | Ile | Val | Asp | Ser |
| | | | 260 | | | | | 265 | | | | | 270 | | |
| Cys | Ile | Pro | Phe | Cys | Ala | Leu | Ala | Phe | Glu | Gln | Asn | Ala | Thr | Gln | Glu |
| | | 275 | | | | | 280 | | | | | 285 | | | |
| His | Ile | Ser | His | Leu | Ala | Asn | Phe | Asp | Ser | Leu | Thr | Gly | Leu | Leu | Asn |
| | 290 | | | | | 295 | | | | | 300 | | | | |
| Arg | Ser | Ser | Val | His | Lys | Val | Ile | Glu | Gly | Met | Ile | Ser | Lys | Gln | Asp |
| 305 | | | | | 310 | | | | | 315 | | | | | 320 |
| Gly | Asn | Arg | Gln | Phe | Ala | Ile | Phe | Met | Leu | Asp | Ile | Asp | Arg | Phe | Arg |
| | | | | 325 | | | | | 330 | | | | | 335 | |
| Asp | Ile | Asn | Asp | Ala | Leu | Gly | His | Val | Tyr | Ala | Asp | Gln | Phe | Leu | Ile |
| | | | 340 | | | | | 345 | | | | | 350 | | |
| Glu | Ile | Ala | Ala | Arg | Ile | Arg | Ser | Ile | Ala | Lys | Glu | Asp | Tyr | Val | Leu |
| | | | 355 | | | | | 360 | | | | | 365 | | |
| Ser | Arg | Ser | Gly | Gly | Asp | Glu | Phe | Val | Val | Val | Val | Pro | Asp | Cys | Pro |
| | 370 | | | | | 375 | | | | | 380 | | | | |
| His | Lys | Glu | Ala | Thr | Asp | Phe | Ala | Glu | His | Leu | Leu | Ala | Ser | Met | Thr |
| 385 | | | | | 390 | | | | | 395 | | | | | 400 |
| Met | Pro | Met | Gln | Ile | Gly | Gln | Asn | Thr | Leu | Thr | Ile | Ser | Cys | Ser | Ile |
| | | | | 405 | | | | | 410 | | | | | 415 | |
| Gly | Ile | Ser | Thr | Tyr | Pro | Asp | Asn | Gly | Pro | Asp | Ser | Glu | Ser | Leu | Leu |
| | | | 420 | | | | | 425 | | | | | 430 | | |
| Ser | Thr | Ala | Asp | Val | Ala | Leu | Arg | Gln | Ala | Lys | Glu | Asp | Gly | Arg | Gly |
| | | 435 | | | | | 440 | | | | | 445 | | | |
| Val | Phe | Arg | Phe | Ala | Asn | Leu | Glu | Lys | Asn | Gln | Val | Ala | Gln | Asp | Arg |
| | 450 | | | | | 455 | | | | | 460 | | | | |
| Leu | Val | Leu | Gly | Ser | Ala | Leu | Arg | Asp | Ser | Leu | Ala | Lys | Gly | Met | Leu |
| 465 | | | | | 470 | | | | | 475 | | | | | 480 |
| Asn | Leu | His | Tyr | Gln | Pro | Gln | Val | Arg | Thr | His | Thr | Leu | Glu | Leu | Ser |
| | | | | 485 | | | | | 490 | | | | | 495 | |
| Gly | Val | Glu | Ala | Leu | Ser | Arg | Trp | His | His | Pro | His | Leu | Gly | Asn | Ile |
| | | | 500 | | | | | 505 | | | | | 510 | | |
| Phe | Pro | Ser | Arg | Phe | Ile | Ala | Val | Ala | Glu | Glu | Thr | Gly | Gln | Ile | Glu |
| | | 515 | | | | | 520 | | | | | 525 | | | |
| Ala | Ile | Gly | Arg | Trp | Ser | Leu | Leu | Glu | Ala | Cys | Arg | Gln | Ile | Val | Lys |
| | | 530 | | | | | 535 | | | | | 540 | | | |

| Trp | Asp | Arg | Asp | Gly | Ile | His | Val | Pro | Thr | Val | Ala | Val | Asn | Leu | Ser |
| 545 | | | | | 550 | | | | | 555 | | | | | 560 |

| Ala | Val | His | Phe | Arg | Asn | Arg | Ala | Leu | Pro | Glu | His | Ile | Ala | Ala | Leu |
| | | | | 565 | | | | | 570 | | | | | 575 | |

| Leu | Lys | Asp | His | Asn | Leu | Lys | Pro | Ser | Arg | Leu | Thr | Val | Glu | Ile | Thr |
| | | | 580 | | | | | 585 | | | | | 590 | | |

| Glu | Ser | Val | Met | Met | Asp | Asn | Ser | Arg | Asp | Thr | Glu | Glu | Val | Leu | Gln |
| | | 595 | | | | | 600 | | | | | 605 | | | |

| Ser | Ile | Arg | Asn | Ile | Gly | Cys | Gly | Leu | Ser | Met | Asp | Asp | Phe | Gly | Thr |
| | 610 | | | | | 615 | | | | | 620 | | | | |

| Gly | Tyr | Ser | Ser | Leu | Ser | Arg | Leu | Thr | Arg | Leu | Pro | Leu | Thr | Glu | Ile |
| 625 | | | | | 630 | | | | | 635 | | | | | 640 |

| Lys | Ile | Asp | Arg | Ser | Phe | Ile | Asn | Asp | Phe | Glu | His | Asp | Thr | Asn | Ala |
| | | | | 645 | | | | | 650 | | | | | 655 | |

| Gln | Ala | Val | Thr | Met | Ala | Val | Ile | Gly | Ile | Gly | Ser | Arg | Leu | Gly | Met |
| | | | 660 | | | | | 665 | | | | | 670 | | |

| Thr | Val | Val | Thr | Glu | Gly | Val | Glu | Thr | Glu | Gln | Gln | Arg | Asp | Leu | Leu |
| | | 675 | | | | | 680 | | | | | 685 | | | |

| Glu | Lys | Leu | Asn | Cys | Asp | Val | Met | Gln | Gly | Tyr | Leu | Phe | Ala | Lys | Pro |
| | 690 | | | | | 695 | | | | | 700 | | | | |

| Leu | Ala | Pro | Asp | Asp | Phe | Glu | Lys | Trp | Met | Arg | His | His | Gln | Thr | Ile |
| 705 | | | | | 710 | | | | | 715 | | | | | 720 |

| Arg | Gln | Met | Leu | Pro | Ala | Ala | Pro | Ala | Ala | Lys | Asn | Val | Ser | Ser | Lys |
| | | | | 725 | | | | | 730 | | | | | 735 | |

| Lys | Lys | Thr | Ser |
| | | | 740 |

( 2 ) INFORMATION FOR SEQ ID NO:11:

( i ) SEQUENCE CHARACTERISTICS:
        ( A ) LENGTH: 493 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Acetobacter xylinum ( x i ) SEQUENCE DESCRIPTION: SEQ ID NO:11:

| Met | Ser | Ala | Pro | His | Asp | Asn | Arg | Leu | Arg | Ala | Leu | Thr | His | Glu | Asp |
| 1 | | | | 5 | | | | | 10 | | | | | 15 | |

| Ala | Asp | Phe | Trp | Ala | Asp | Val | Val | Asp | Asn | Val | Leu | Ile | Val | Ala | Val |
| | | | 20 | | | | | 25 | | | | | 30 | | |

| Thr | Asp | Arg | Lys | Gly | Ile | Ile | Thr | Tyr | Val | Asn | Asp | Lys | Phe | Cys | Glu |
| | | 35 | | | | | 40 | | | | | 45 | | | |

| Ile | Ser | Gln | Tyr | Ser | Arg | Glu | Glu | Leu | Leu | Gly | His | Thr | His | Arg | Ile |
| | 50 | | | | | 55 | | | | | 60 | | | | |

| Leu | Asn | Ser | Gly | Glu | His | Gly | Lys | Ala | Phe | Phe | Arg | Glu | Met | Tyr | Gln |
| 65 | | | | | 70 | | | | | 75 | | | | | 80 |

| Thr | Leu | Phe | Ser | Gly | Arg | Thr | Trp | Tyr | Gly | Asn | Leu | Cys | Asn | Arg | Ala |
| | | | | 85 | | | | | 90 | | | | | 95 | |

| Lys | Asp | Gly | Ser | His | Tyr | Trp | Val | Ala | Thr | Thr | Ile | Met | Pro | His | Arg |
| | | | 100 | | | | | 105 | | | | | 110 | | |

| Asn | Ala | Lys | Gly | Glu | Ile | Thr | Gly | Phe | Val | Ala | Ser | Arg | Phe | Glu | Ile |

|     |     |     |     | 115 |     |     |     |     | 120 |     |     |     |     | 125 |     |
| --- | --- | --- | --- | --- | --- | --- | --- | --- | --- | --- | --- | --- | --- | --- | --- |
| Thr | Glu | Leu | Met | Asn | Thr | Lys | Val | Arg | Leu | Lys | Lys | Gln | Ala | Ala | Thr |
|     |     |     |     |     |     |     |     |     |     |     |     |     |     |     |     |
| 130 |     |     |     |     | 135 |     |     |     |     | 140 |     |     |     |     |     |
| Asp | Val | Leu | Thr | Gly | Leu | Leu | Asn | Arg | Gly | Gly | Phe | Asn | Ala | Ser | Leu |
| 145 |     |     |     |     | 150 |     |     |     |     | 155 |     |     |     |     | 160 |
| Val | Thr | Ala | Leu | Glu | Asn | Ala | Lys | Arg | Pro | His | Pro | Glu | Pro | Gln | Ala |
|     |     |     |     | 165 |     |     |     |     | 170 |     |     |     |     | 175 |     |
| Leu | Val | Met | Phe | Asp | Leu | Asp | Gly | Phe | Lys | Pro | Val | Asn | Asp | Ile | His |
|     |     |     | 180 |     |     |     |     | 185 |     |     |     |     | 190 |     |     |
| Gly | His | His | Ala | Gly | Asp | Glu | Val | Leu | Lys | Val | Ile | Gly | Gln | Arg | Leu |
|     |     | 195 |     |     |     |     | 200 |     |     |     |     | 205 |     |     |     |
| Ile | Glu | Leu | Ile | Gly | Pro | Asp | Asp | Ala | Ile | Ser | Arg | Leu | Gly | Gly | Asp |
|     | 210 |     |     |     |     | 215 |     |     |     |     | 220 |     |     |     |     |
| Glu | Phe | Ala | Ile | Ile | Leu | Arg | Arg | Ser | Leu | Lys | Leu | Met | Pro | Leu | Glu |
| 225 |     |     |     |     | 230 |     |     |     |     | 235 |     |     |     |     | 240 |
| Thr | Ile | Leu | Thr | Lys | Val | Gln | Asn | Leu | Leu | Glu | Glu | Pro | Ile | Met | Leu |
|     |     |     |     | 245 |     |     |     |     | 250 |     |     |     |     | 255 |     |
| Asp | Ser | Ala | Thr | Val | Arg | Ile | Ser | Gly | Ser | Ile | Gly | Ala | Thr | Pro | Ile |
|     |     |     | 260 |     |     |     |     | 265 |     |     |     |     | 270 |     |     |
| Thr | Gly | Ala | Asp | Thr | Leu | Glu | Gly | Leu | Gln | Lys | Asn | Ala | Asp | Val | Ala |
|     |     | 275 |     |     |     |     | 280 |     |     |     |     | 285 |     |     |     |
| Val | Tyr | Ala | Ala | Lys | Gln | Ser | Gly | Gly | Lys | Gln | Ala | Arg | Met | Phe | Thr |
|     | 290 |     |     |     |     | 295 |     |     |     |     | 300 |     |     |     |     |
| Pro | Ser | Leu | His | Lys | Thr | Thr | Met | Glu | Arg | Ala | Lys | Ile | Leu | Thr | Glu |
| 305 |     |     |     |     | 310 |     |     |     |     | 315 |     |     |     |     | 320 |
| Ala | Arg | Lys | Gly | Val | Glu | Leu | Arg | Gln | Phe | Glu | Val | Tyr | Tyr | Gln | Pro |
|     |     |     |     | 325 |     |     |     |     | 330 |     |     |     |     | 335 |     |
| Ile | Leu | Asn | Ala | Arg | Thr | Gly | Arg | Ile | Glu | Gln | Ala | Glu | Ala | Leu | Met |
|     |     |     | 340 |     |     |     |     | 345 |     |     |     |     | 350 |     |     |
| Arg | Trp | His | His | Pro | Asp | Arg | Gly | Leu | Leu | Ser | Ala | Gly | Ala | Phe | Thr |
|     |     | 355 |     |     |     |     | 360 |     |     |     |     | 365 |     |     |     |
| Asp | Val | Phe | Ala | Asp | Ser | Ala | Leu | Ala | Gln | Ile | Met | Glu | Thr | His | Leu |
|     | 370 |     |     |     |     | 375 |     |     |     |     | 380 |     |     |     |     |
| Val | Gln | Ser | Phe | His | Asp | Asp | Ile | Gln | Lys | Trp | Lys | Glu | Ala | Gly | Leu |
| 385 |     |     |     |     | 390 |     |     |     |     | 395 |     |     |     |     | 400 |
| Pro | Ser | Leu | Arg | Leu | Ala | Val | Asn | Leu | Ser | His | Leu | Asp | Leu | Leu | Asn |
|     |     |     |     | 405 |     |     |     |     | 410 |     |     |     |     | 415 |     |
| Leu | Glu | Gln | Gln | Ile | Asp | Leu | Phe | Ser | Glu | Ile | Arg | Glu | Leu | Asn | Leu |
|     |     |     | 420 |     |     |     |     | 425 |     |     |     |     | 430 |     |     |
| Glu | Pro | Ser | Thr | Phe | Ile | Leu | Glu | Val | Thr | Glu | Gln | Ile | Leu | Gln | Gly |
|     |     | 435 |     |     |     |     | 440 |     |     |     |     | 445 |     |     |     |
| Arg | Arg | Ala | Glu | Lys | Asn | Arg | Leu | Arg | Leu | Arg | Ser | Leu | Ser | Gly | Asn |
|     | 450 |     |     |     |     | 455 |     |     |     |     | 460 |     |     |     |     |
| Gly | Phe | Gly | Leu | Ala | Met | Asp | Lys | Phe | Gly | Tyr | Gly | Thr | Val | Arg | Leu |
| 465 |     |     |     |     | 470 |     |     |     |     | 475 |     |     |     |     | 480 |
| Ser | Thr | Leu | Gly | Glu | Leu | Pro | Phe | Gln | Ser | Leu | Lys | Leu |     |     |     |
|     |     |     |     | 485 |     |     |     |     | 490 |     |     |     |     |     |     |

( 2 ) INFORMATION FOR SEQ ID NO:12:

( i ) SEQUENCE CHARACTERISTICS:
      ( A ) LENGTH: 33 amino acids
      ( B ) TYPE: amino acid
      ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Acetobacter xylinum ( x i ) SEQUENCE DESCRIPTION: SEQ ID NO:12:

```
Xaa Leu Ser Glu Leu Ala Glu Thr Asp Thr Leu Thr Ala Leu Leu Asn
1               5                   10                  15
Arg Gly Gly Phe Asn Thr Ala Leu Ser Ala Ala Leu Gly Xaa Xaa Xaa
            20                  25                  30
Lys
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Acetobacter xylinum ( x i ) SEQUENCE DESCRIPTION: SEQ ID NO:13:

```
Gly Gly Phe Asn Thr Ala
1               5
```

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:14:

GGNGGNTTYA AYACNGC                                                  17

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:15:

GGMGGMTTYA AYACMGC                                                  17

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:16:

GGKGGMTTYA AYACMGC 17

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:17:

GGMGGKTTYA AYACKGC 17

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:18:

GGMGGMTTYA AYACK 15

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:19:

GGKGGKTTYA AYACMGC 17

( 2 ) INFORMATION FOR SEQ ID NO:20:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:20:

GGKGGMTTYA AYACKGC 17

( 2 ) INFORMATION FOR SEQ ID NO:21:

( i ) SEQUENCE CHARACTERISTICS:
        ( A ) LENGTH: 17 base pairs ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:21:

GGMGGKTTYA A YACKGC                                                            17

( 2 ) INFORMATION FOR SEQ ID NO:22:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:22:

GGKGGKTTYA AYACKGC                                                             17

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Acetobacter xylinum ( x i ) SEQUENCE DESCRIPTION: SEQ ID NO:23:

Ala Glu Thr Asp Thr
    1               5

( 2 ) INFORMATION FOR SEQ ID NO:24:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:24:

GCNGARACNG AYAC                                                                14

( 2 ) INFORMATION FOR SEQ ID NO:25:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:25:

GCNGARACTG AYAC                                                                14

( 2 ) INFORMATION FOR SEQ ID NO:26:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:26:

GCNGARACCG AYAC     14

( 2 ) INFORMATION FOR SEQ ID NO:27:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:27:

GCNGARACAG AYAC     14

( 2 ) INFORMATION FOR SEQ ID NO:28:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:28:

GCNGARACGG AYAC     14

( 2 ) INFORMATION FOR SEQ ID NO:29:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:29:

CCSGATATHA CNGC     14

( 2 ) INFORMATION FOR SEQ ID NO:30:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:30:

CCWGACATHA CNGC 14

( 2 ) INFORMATION FOR SEQ ID NO:31:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:31:

CCSGACATHA CNGC 14

( 2 ) INFORMATION FOR SEQ ID NO:32:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:32:

CCWGACATHA CNGC 14

( 2 ) INFORMATION FOR SEQ ID NO:33:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:33:

CCCGACATWA CSGC 14

( 2 ) INFORMATION FOR SEQ ID NO:34:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:34:

CCWGATATWA CWGC 14

( 2 ) INFORMATION FOR SEQ ID NO:35:

( i ) SEQUENCE CHARACTERISTICS:
                ( A ) LENGTH: 14 base pairs
                ( B ) TYPE: nucleic acid ( C ) STRANDEDNESS: single
( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:35:

CCCGACATHA CNGC 14

( 2 ) INFORMATION FOR SEQ ID NO:36:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:36:

CCCGAAATHA CNGC 14

( 2 ) INFORMATION FOR SEQ ID NO:37:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:37:

CCCGATATHA CNGC 14

( 2 ) INFORMATION FOR SEQ ID NO:38:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:38:

CCGGACATHA CNGC 14

( 2 ) INFORMATION FOR SEQ ID NO:39:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:39:

CCGGAAATHA CNGC 14

( 2 ) INFORMATION FOR SEQ ID NO:40:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:40:

CCGGATATHA CNGC      14

( 2 ) INFORMATION FOR SEQ ID NO:41:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:41:

CCCGACATCA CSGC      14

( 2 ) INFORMATION FOR SEQ ID NO:42:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:42:

CCCGACATCA CGGC      14

( 2 ) INFORMATION FOR SEQ ID NO:43:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:43:

CCGGACATCA CCGC      14

( 2 ) INFORMATION FOR SEQ ID NO:44:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:44:

CCGGACATCA CGGC 14

( 2 ) INFORMATION FOR SEQ ID NO:45:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:45:

CCCGACATCA CAGC 14

( 2 ) INFORMATION FOR SEQ ID NO:46:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:46:

CCCGACATCA CTGC 14

( 2 ) INFORMATION FOR SEQ ID NO:47:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:47:

TGATCTGCTA CGGGATAG 18

( 2 ) INFORMATION FOR SEQ ID NO:48:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:48:

GACAGCGAAT CCCTGCTCA 19

( 2 ) INFORMATION FOR SEQ ID NO:49:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:49:

CCGTGCATTT CCGCAAC 17

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:50:

TACTGGGTGG CCACCACC 18

( 2 ) INFORMATION FOR SEQ ID NO:51:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:51:

CATGGCCACC ATGCG 15

( 2 ) INFORMATION FOR SEQ ID NO:52:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Acteobacter xylinum ( x i ) SEQUENCE DESCRIPTION: SEQ ID NO:52:

Pro Asp Ile Thr Ala Leu Thr Thr Glu Ile Leu Leu Pro Ala Leu Glu
1              5                    10                  15

Arg Ala ( 2 ) INFORMATION FOR SEQ ID NO:53:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:53:

```
Asp Ser Leu Thr Gly Leu Leu Asn Arg Gly Ala Leu
1               5                   10
```

( 2 ) INFORMATION FOR SEQ ID NO:54:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:54:

```
Asp Ser Leu Thr Gly Leu Leu Asn Arg Thr Ser Leu
1               5                   10
```

( 2 ) INFORMATION FOR SEQ ID NO:55:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:55:

```
Asp Ser Leu Thr Gly Leu Leu Asn Arg Ser Ser Val
1               5                   10
```

( 2 ) INFORMATION FOR SEQ ID NO:56:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:56:

```
Asp Pro Leu Thr Gly Leu Phe Asn Arg Gly Gly Phe
1               5                   10
```

( 2 ) INFORMATION FOR SEQ ID NO:57:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide (iii) HYPOTHETICAL: NO (v) FRAGMENT TYPE: internal (xi) SEQUENCE DESCRIPTION: SEQ ID NO:57:

Asp Thr Leu Thr Gly Leu Leu Asn Arg Gly Gly Phe
1               5                       10

(2) INFORMATION FOR SEQ ID NO:58:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (iii) HYPOTHETICAL: YES (v) FRAGMENT TYPE: internal (xi) SEQUENCE DESCRIPTION: SEQ ID NO:58:

Asp Ser Leu Thr Gly Leu Leu Asn Arg Gly Xaa Leu
1               5                       10

(2) INFORMATION FOR SEQ ID NO:59:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:59:

GACAGCCTGA CCGGCCTGCT CAACCGTGGC GCGCTG                                    36

(2) INFORMATION FOR SEQ ID NO:60:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:60:

GACAGCCTGA CCGGGCTGCT CAACCGCACG TCGCTG                                    36

(2) INFORMATION FOR SEQ ID NO:61:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:61:

GACAGCCTGA CCGGGCTGCT CAACCGCTCC TCGGTG                                    36

(2) INFORMATION FOR SEQ ID NO:62:

(i) SEQUENCE CHARACTERISTICS:
    (A) LENGTH: 36 base pairs
    (B) TYPE: nucleic acid

```
        ( C ) STRANDEDNESS: single
        ( D ) TOPOLOGY: linear ( i i ) MOLECULE TYPE: DNA ( x i ) SEQUENCE DESCRIPTION: SEQ ID NO:62:

GACCCGCTGA  CGGGGCTGTT  CAACCGTGGT  GGCTTC                              36

( 2 ) INFORMATION FOR SEQ ID NO:63:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:63:

GATACCCTGA  CCGGCCTGCT  CAACCGCGGC  GGCTTC                              36
```